US012616747B2

(12) United States Patent
McLellan et al.

(10) Patent No.: US 12,616,747 B2
(45) Date of Patent: May 5, 2026

(54) STABILIZED BETA-CORONAVIRUS ANTIGENS

(71) Applicant: Board of Regents, The University of Texas System, Austin, TX (US)

(72) Inventors: Jason McLellan, Austin, TX (US);
Ching-Lin Hsieh, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 555 days.

(21) Appl. No.: 18/061,256

(22) Filed: Dec. 2, 2022

(65) Prior Publication Data

US 2023/0277653 A1    Sep. 7, 2023

Related U.S. Application Data

(60) Provisional application No. 63/285,548, filed on Dec. 3, 2021.

(51) Int. Cl.
*A61K 39/215*    (2006.01)
*A61P 37/04*    (2006.01)
*A61K 39/00*    (2006.01)

(52) U.S. Cl.
CPC ............ *A61K 39/215* (2013.01); *A61P 37/04* (2018.01); *A61K 2039/505* (2013.01); *A61K 2039/53* (2013.01)

(58) Field of Classification Search
None
See application file for complete search history.

(56) References Cited

U.S. PATENT DOCUMENTS

| | | | |
|---|---|---|---|
| 9,738,689 B2 | 8/2017 | Kwong et al. | |
| 10,960,070 B2 | 3/2021 | Graham et al. | |
| 11,684,669 B2 * | 6/2023 | Meinke ................... | A61P 31/14 |
| | | | 424/186.1 |
| 11,964,010 B2 | 4/2024 | Graham et al. | |
| 2017/0182151 A1 | 6/2017 | Che et al. | |
| 2021/0388032 A1 | 12/2021 | Langedijk et al. | |
| 2023/0226171 A1 | 7/2023 | Lozano-Dubernard et al. | |
| 2023/0242594 A1 | 8/2023 | McLellan et al. | |
| 2023/0310583 A1 | 10/2023 | Sun et al. | |
| 2024/0210415 A1 | 6/2024 | Krammer et al. | |

FOREIGN PATENT DOCUMENTS

| | | |
|---|---|---|
| CN | 111088283 A | 5/2020 |
| EP | 2970398 | 1/2016 |
| EP | 3532095 | 9/2019 |
| WO | WO 2014/160463 | 10/2014 |
| WO | WO 2016/037154 | 3/2016 |
| WO | WO 2017/037196 | 3/2017 |
| WO | WO 2018/081318 | 5/2018 |
| WO | WO 2020/028902 | 2/2020 |
| WO | WO 2021/163365 | 8/2021 |
| WO | WO 2021/194826 | 9/2021 |
| WO | WO 2021/226348 | 11/2021 |
| WO | WO 2021/229270 | 11/2021 |
| WO | WO 2021/229311 | 11/2021 |
| WO | WO 2021/243122 | 12/2021 |
| WO | WO 2022/241229 | 11/2022 |

OTHER PUBLICATIONS

Hsieh et al. (Nature Communications, 2024, p. 1-14).*
Baden, Lindsey R., et al. "Efficacy and safety of the mRNA-1273 SARS-CoV-2 vaccine." *New England journal of medicine* 384.5 (2021): 403-416.
Battles, M. B. et al. Structure and immunogenicity of pre-fusion-stabilized human metapneumovirus F glycoprotein. *Nat. Commun.* 8, 1528 (2017).
Bosch, Berend Jan, et al. "The coronavirus spike protein is a class I virus fusion protein: structural and functional characterization of the fusion core complex." *Journal of virology* 77.16 (2003): 8801-8811.
Boyoglu-Barnum, Seyhan, et al. "Glycan repositioning of influenza hemagglutinin stem facilitates the elicitation of protective cross-group antibody responses." *Nature communications* 11.1 (2020): 791.
Buchholz, U. J. et al. Contributions of the structural proteins of severe respiratory syndrome coronavirus to protective immunity. *Proc. Natl. Acad. Sci. U. S. A.* 101, 9804-9809 (2004).
Chan, Woan-Eng, et al. "Functional characterization of heptad repeat 1 and 2 mutants of the spike protein of severe acute respiratory syndrome coronavirus." *Journal of virology* 80.7 (2006): 3225-3237.
Chen, Yu, Qianyun Liu, and Deyin Guo. "Emerging coronaviruses: genome structure, replication, and pathogenesis." *Journal of medical virology* 92.4 (2020): 418-423.
Chi, Xiangyang, et al. "A neutralizing human antibody binds to the N-terminal domain of the Spike protein of SARS-CoV-2." *Science* 369.6504 (2020): 650-655.
Choi, Bina, et al. "Persistence and evolution of SARS-CoV-2 in an immunocompromised host." *New England Journal of Medicine* 383.23 (2020): 2291-2293.
Cockrell, Adam S., et al. "A mouse model for MERS coronavirus-induced acute respiratory distress syndrome." *Nature microbiology* 2.2 (2016): 1-11.

(Continued)

*Primary Examiner* — Agnieszka Boesen

(74) *Attorney, Agent, or Firm* — pH IP Law

(57) ABSTRACT

Provided herein are engineered protein comprising stabilized coronavirus S protein ectodomains, such as stabilized SARS-CoV-2 S protein ectodomains. In some aspects, the engineered S protein ectodomains exhibit enhanced antigenicity. Methods are also provided for use of the engineered S protein ectodomains as diagnostics, in screening platforms, and/or in vaccine compositions.

20 Claims, 29 Drawing Sheets
(28 of 29 Drawing Sheet(s) Filed in Color)
Specification includes a Sequence Listing.

(56)                    References Cited

OTHER PUBLICATIONS

Corbett, Kizzmekia S., et al. "Design of nanoparticulate group 2 influenza virus hemagglutinin stem antigens that activate unmutated ancestor B cell receptors of broadly neutralizing antibody lineages." *MBio* 10.1 (2019): 10-1128.

Corbett, Kizzmekia S., et al. "Evaluation of the mRNA-1273 vaccine against SARS-CoV-2 in nonhuman primates." *New England Journal of Medicine* 383.16 (2020): 1544-1555.

Corbett, Kizzmekia S., et al. "SARS-CoV-2 mRNA vaccine design enabled by prototype pathogen preparedness." *Nature* 586.7830 (2020): 567-571.

De la Pena, Alba Torrents, et al. "Improving the immunogenicity of native-like HIV-1 envelope trimers by hyperstabilization." *Cell reports* 20.8 (2017): 1805-1817.

Douglas, Madeline G., et al. "Adaptive evolution influences the infectious dose of MERS-CoV necessary to achieve severe respiratory disease." *Virology* 517 (2018): 98-107.

Escriou, Nicolas, et al. "Protection from SARS coronavirus conferred by live measles vaccine expressing the spike glycoprotein." *Virology* 452 (2014): 32-41.

Feige, Matthias J., ed. *Oxidative folding of proteins: Basic principles, cellular regulation and engineering.* vol. 9. Royal Society of Chemistry, 2018, Chapter 1.1: Disulfide Bonds in Protein Folding and Stability, pp. 1-33.

Gu, Hongjing, et al. "Adaptation of SARS-CoV-2 in BALB/c mice for testing vaccine efficacy." *Science* 369.6511 (2020): 1603-1607.

Henderson, Rory, et al. "Controlling the SARS-CoV-2 spike glycoprotein conformation." *Nature structural & molecular biology* 27.10 (2020): 925-933.

Hofmann, H. et al. S Protein of Severe Acute Respiratory Syndrome-Associated Coronavirus Mediates Entry into Hepatoma Cell Lines and Is Targeted by Neutralizing Antibodies in Infected Patients. *J. Virol.* 78, 6134-6142 (2004).

Hsieh, Ching-Lin, et al. "Structure-based design of prefusion-stabilized SARS-CoV-2 spikes." *Science* 369.6510 (2020): 1501-1505.

Huang, Yimin, et al. "Identification of a conserved neutralizing epitope present on spike proteins from all highly pathogenic coronaviruses." *BioRxiv* (2021): Jan. 2021.

Impagliazzo, Antonietta, et al. "A stable trimeric influenza hemagglutinin stem as a broadly protective immunogen." *Science* 349.6254 (2015): 1301-1306.

Jackson, Lisa A., et al. "An mRNA vaccine against SARS-CoV-2-preliminary report." *New England journal of medicine* 383.20 (2020): 1920-1931.

Joyce, M. G. et al. Iterative structure-based improvement of a fusion-glycoprotein vaccine against RSV. *Nat. Struct. Mol. Biol.* 23, 811-820 (2016).

Ke, Zunlong, et al. "Structures and distributions of SARS-CoV-2 spike proteins on intact virions." *Nature* 588.7838 (2020): 498-502.

Kirchdoerfer, Robert N., et al. "Pre-fusion structure of a human coronavirus spike protein." *Nature* 531.7592 (2016): 118-121.

Kirchdoerfer, Robert N., et al. "Stabilized coronavirus spikes are resistant to conformational changes induced by receptor recognition or proteolysis." *Scientific reports* 8.1 (2018): 15701.

Krarup, Anders, et al. "A highly stable prefusion RSV F vaccine derived from structural analysis of the fusion mechanism." *Nature communications* 6.1 (2015): 8143.

Ku, Zhiqiang, et al. "Molecular determinants and mechanism for antibody cocktail preventing SARS-CoV-2 escape." *Nature communications* 12.1 (2021): 469.

Kupferschmidt, Kai. "Fast-spreading UK virus variant raises alarms." (2021): 9-10.

Li, Fang. "Structure, function, and evolution of coronavirus spike proteins." *Annual review of virology* 3.1 (2016): 237-261.

Li, Z. et al. The human coronavirus HCoV-229E S-protein structure and receptor binding. *Elife* 8, 1-22 (2019).

Liu, Lihong, et al. "Potent neutralizing antibodies against multiple epitopes on SARS-CoV-2 spike." *Nature* 584.7821 (2020): 450-456.

Lucchese, Guglielmo, Animesh Amart Sinha, and Darja Kanduc. "How a single amino acid change may alter the immunological information of a peptide." *Frontiers in Bioscience—Elite* 4.5 (2012): 1843-1852.

Ma, Cuiqing, et al. "Searching for an ideal vaccine candidate among different MERS coronavirus receptor-binding fragments—the importance of immunofocusing in subunit vaccine design." *Vaccine* 32.46 (2014): 6170-6176.

MacGowan, Stuart A., and Geoffrey J. Barton. "Missense variants in ACE2 are predicted to encourage and inhibit interaction with SARS-CoV-2 Spike and contribute to genetic risk in COVID-19." *BioRxiv* (2020): May 2020.

McLellan, J. S. et al. Structure-Based Design of a Fusion Glycoprotein Vaccine for Respiratory Syncytial Virus. *Science* (80-. ). 342, 592-598 (2013).

Menachery, Vineet D., et al. "SARS-like WIV1-CoV poised for human emergence." *Proceedings of the National Academy of Sciences* 113.11 (2016): 3048-3053.

Ng, Kevin W., et al. "Preexisting and de novo humoral immunity to SARS-CoV-2 in humans." *Science* 370.6522 (2020): 1339-1343.

Pallesen, J. et al. Immunogenicity and structures of a rationally designed prefusion MERS-CoV spike antigen. *Proc. Natl. Acad. Sci. U. S. A.* 114, E7348-E7357 (2017).

Park, Y. J. et al. Structures of MERS-CoV spike glycoprotein in complex with sialoside attachment receptors. *Nat. Struct. Mol. Biol.* 26, 1151-1157 (2019).

Polack, Fernando P., et al. "Safety and efficacy of the BNT162b2 mRNA Covid-19 vaccine." *New England journal of medicine* 383.27 (2020): 2603-2615.

Qian, Zhaohui, et al. "Identification of the receptor-binding domain of the spike glycoprotein of human betacoronavirus HKU1." *Journal of Virology* 89.17 (2015): 8816-8827.

Qiao, Hui, et al. "Specific single or double proline substitutions in the "spring-loaded" coiled-coil region of the influenza hemagglutinin impair or abolish membrane fusion activity." *The Journal of cell biology* 141.6 (1998): 1335-1347.

Rutten, L. et al. A Universal Approach to Optimize the Folding and Stability of Prefusion-Closed HIV-1 Envelope Trimers. *Cell Rep.* 23, 584-595 (2018).

Rutten, L. et al. Structure-Based Design of Prefusion-Stabilized Filovirus Glycoprotein Trimers. *Cell Rep.* 30, 4540-4550.e3 (2020).

Sanders, R. W. et al. A next-generation cleaved, soluble HIV-1 Env trimer, BG505 SOSIP.664 gp140, expresses multiple epitopes for broadly neutralizing but not non-neutralizing antibodies. *PLoS Pathog.* 9, e1003618 (2013).

Sanders, Rogier W., et al. "Stabilization of the soluble, cleaved, trimeric form of the envelope glycoprotein complex of human immunodeficiency virus type 1." *Journal of virology* 76.17 (2002): 8875-8889.

Starr, Tyler N., et al. "Deep mutational scanning of SARS-CoV-2 receptor binding domain reveals constraints on folding and ACE2 binding." *cell* 182.5 (2020): 1295-1310.

Stewart-Jones, Guillaume BE, et al. "Structure-based design of a quadrivalent fusion glycoprotein vaccine for human parainfluenza virus types 1-4." *Proceedings of the National Academy of Sciences* 115.48 (2018): 12265-12270.

Tang, Julian W., et al. "Introduction of the South African SARS-CoV-2 variant 501Y. V2 into the UK." *The Journal of infection* 82.4 (2021): e8.

Turoňová, Beata, et al. "In situ structural analysis of SARS-COV-2 spike reveals flexibility mediated by three hinges." Science 370. 6513 (2020): 203-208.

UniProtKB Accession No. P0DTC2, "Spike_SARS2", version last modified Jun. 2, 2021.

UniProtKB Accession No. P11225, "Spike_CVMJH", version last modified Jun. 2, 2021.

UniProtKB Accession No. P25192, "Spike_CVBLY", version last modified Jun. 2, 2021.

Walls, A. C. et al. Structure, Function, and Antigenicity of the SARS-CoV-2 Spike Glycoprotein. *Cell* 181, 281-292.e6 (2020).

Walls, A. C. et al. Tectonic conformational changes of a coronavirus spike glycoprotein promote membrane fusion. *Proc. Natl. Acad. Sci. U. S. A.* 114, 11157-11162 (2017).

(56) References Cited

OTHER PUBLICATIONS

Wang, C. et al. A human monoclonal antibody blocking SARS-CoV-2 infection. *Nat. Commun.* 11, 1-6 (2020).

Wang, Lingshu, et al. "Evaluation of candidate vaccine approaches for MERS-CoV." *Nature communications* 6.1 (2015): 7712.

Wang, Lingshu, et al. "Importance of neutralizing monoclonal antibodies targeting multiple antigenic sites on the Middle East respiratory syndrome coronavirus spike glycoprotein to avoid neutralization escape." *Journal of virology* 92.10 (2018): 10-1128.

Wang, N. et al. Structural Definition of a Neutralization-Sensitive Epitope on the MERS-CoV S1-NTD. *Cell Rep.* 28, 3395-3405.e6 (2019).

Wang, Zijun, et al. "mRNA vaccine-elicited antibodies to SARS-CoV-2 and circulating variants." *Nature* 592.7855 (2021): 616-622.

Weisblum, Yiska, et al. "Escape from neutralizing antibodies by SARS-CoV-2 spike protein variants." *elife* 9 (2020): e61312.

Widjaja, Ivy, et al. "Towards a solution to MERS: protective human monoclonal antibodies targeting different domains and functions of the MERS-coronavirus spike glycoprotein." *Emerging microbes & infections* 8.1 (2019): 516-530.

Woo, Patrick CY, et al. "Characterization and complete genome sequence of a novel coronavirus, coronavirus HKU1, from patients with pneumonia." *Journal of virology* 79.2 (2005): 884-895.

Wrapp, D. et al. Cryo-EM structure of the 2019-nCoV spike in the prefusion conformation. *Science* (80-. ). 367, 1260-1263 (2020).

Wu, Kai, et al. "mRNA-1273 vaccine induces neutralizing antibodies against spike mutants from global SARS-CoV-2 variants." *BioRxiv* (2021): Jan. 2021.

Yang, L. et al. Structure-Guided Redesign Improves NFL HIV Env Trimer Integrity and Identifies an Inter-Protomer Disulfide Permitting Post-Expression Cleavage. *Front. Immunol.* 9, 1631 (2018).

Yassine, Hadi M., et al. "Hemagglutinin-stem nanoparticles generate heterosubtypic influenza protection." *Nature medicine* 21.9 (2015): 1065-1070.

Zhang, Jian, et al. "Spike-specific circulating T follicular helper cell and cross-neutralizing antibody responses in COVID-19-convalescent individuals." *Nature microbiology* 6.1 (2021): 51-58.

Zhao, S., et al. "Quantifying the transmission advantage associated wit h N501Y substitution of SARS-CoV-2 in the United Kingdom: An early data-driven analysis." *J. Travel Med* 28.2 (2021).

GenBank Accession No. MN908947, dated Mar. 18, 2020, retrieved from <https://www/ncbi.nlm.nih.gov/nucore/MN908947> on Jun. 2, 2025.

* cited by examiner

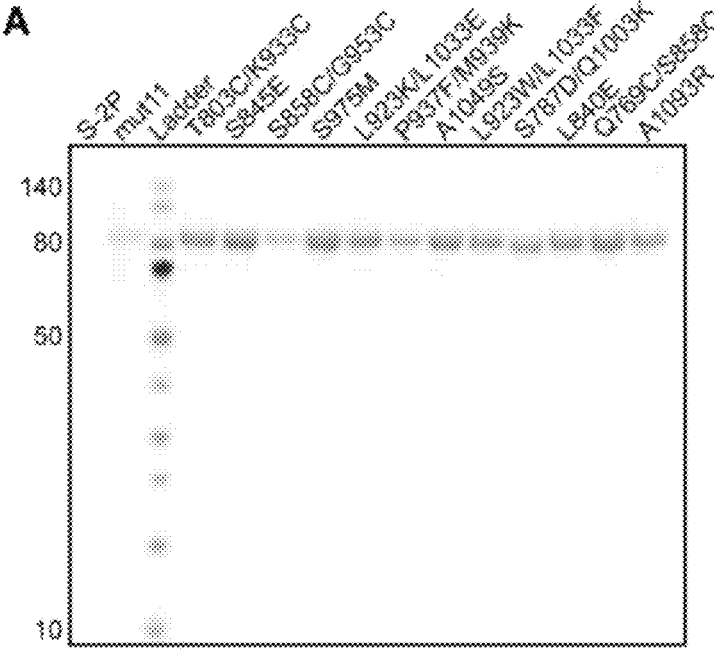
FIG. 2A
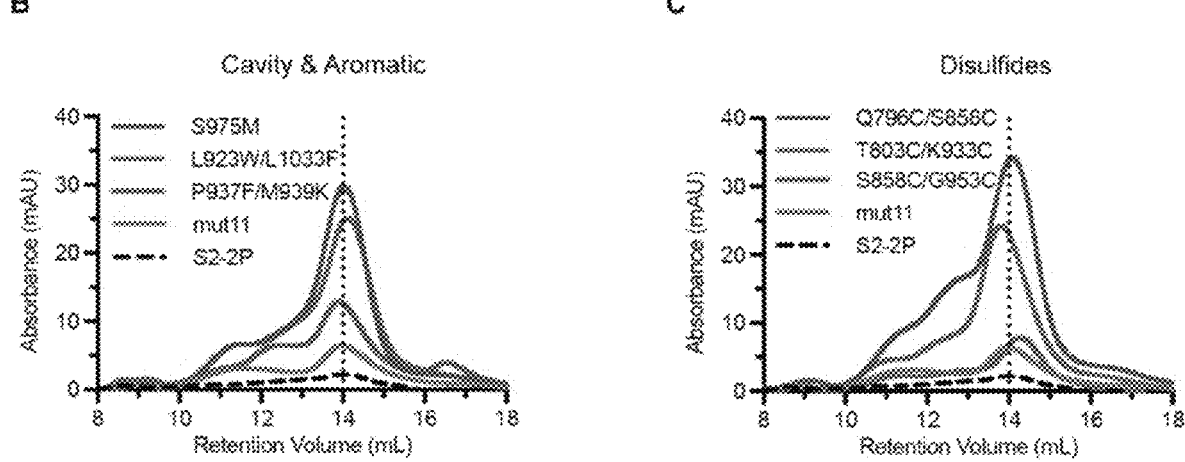
FIGS. 2B-C

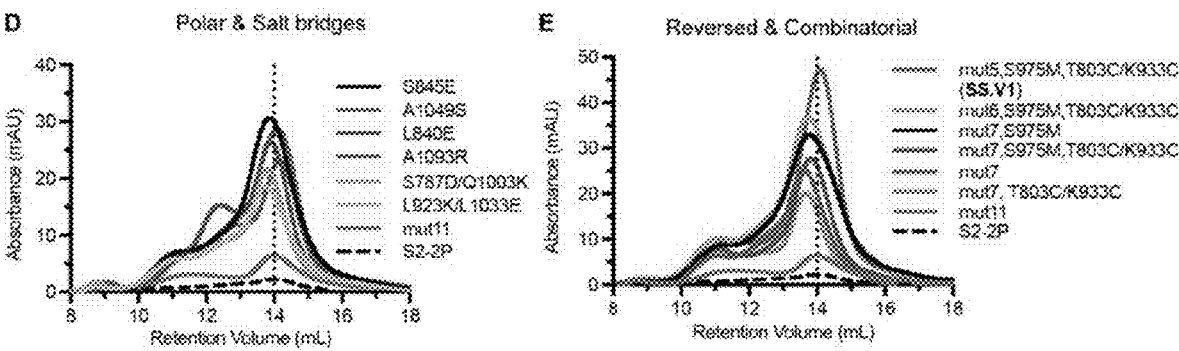
FIGS. 2D-E
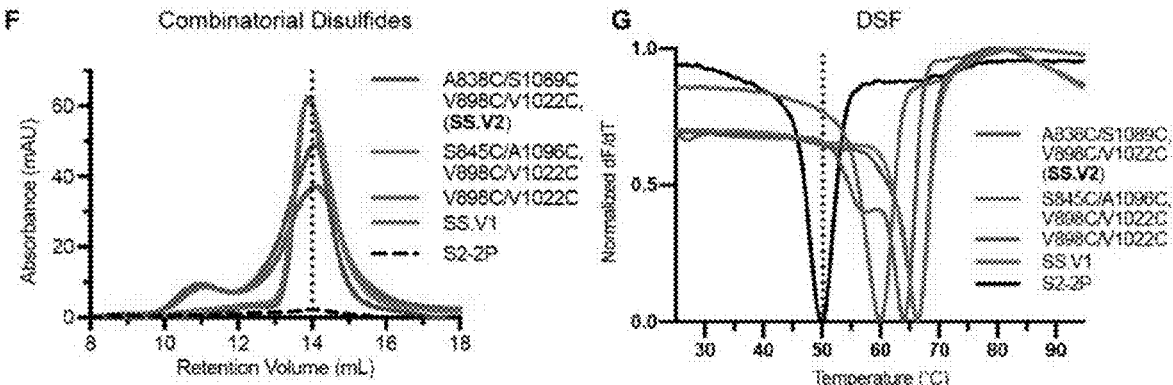
FIGS. 2F-G
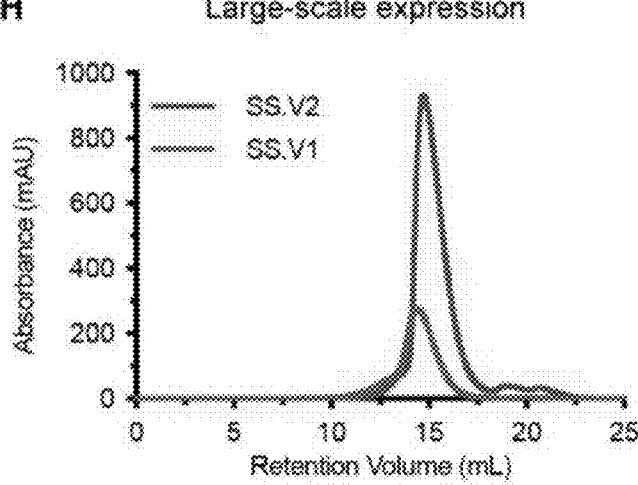
FIG. 2H

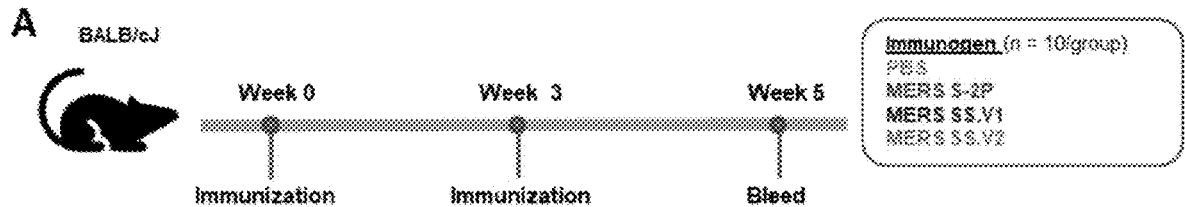
FIG. 3A
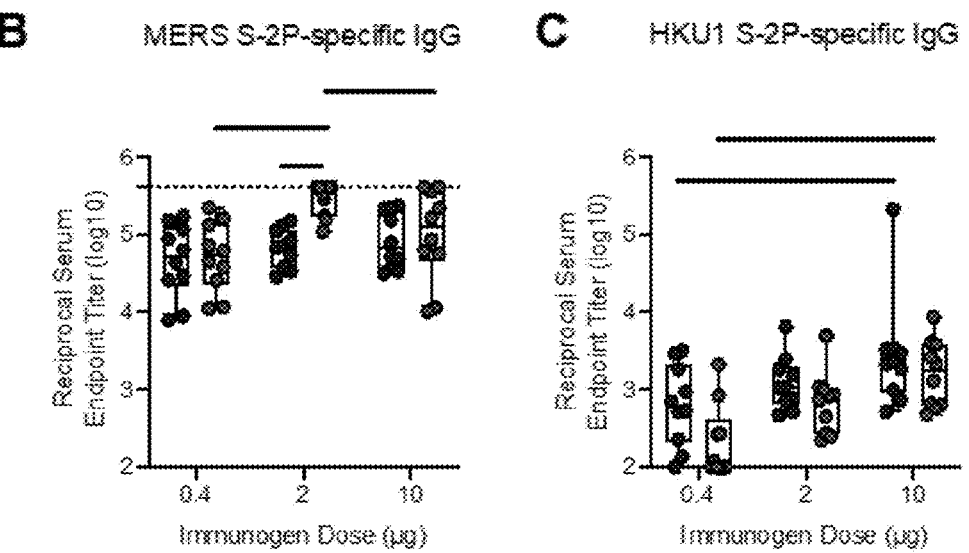
FIGS. 3B-C
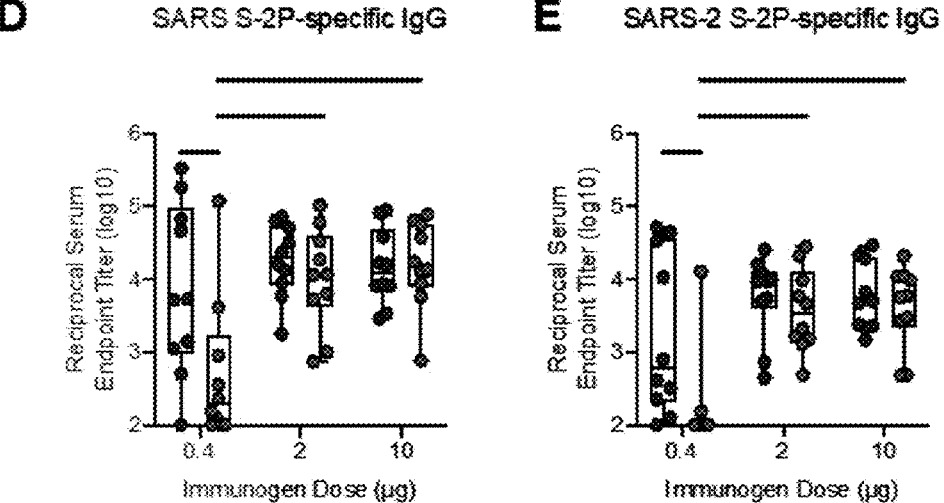
FIGS. 3D-E

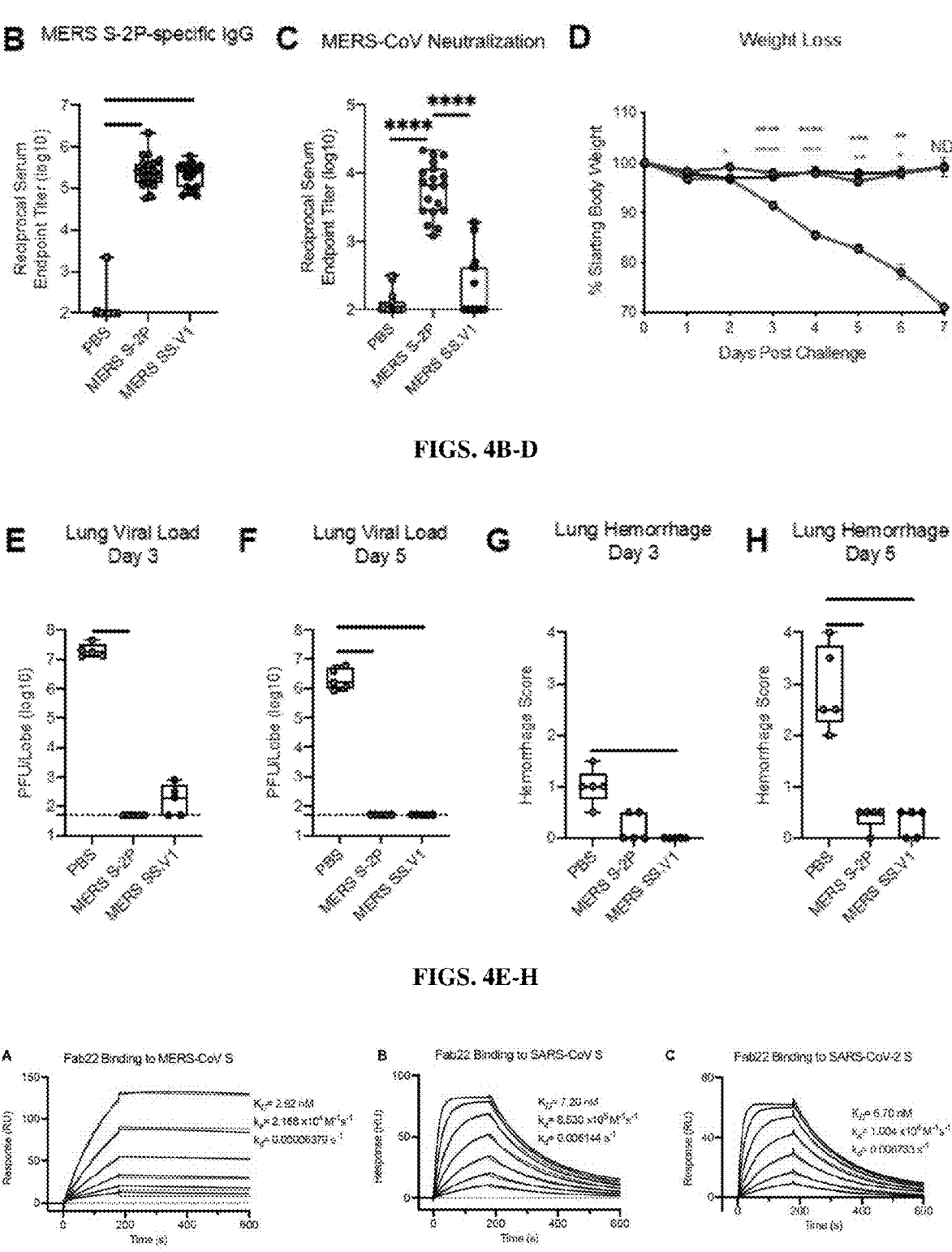
FIGS. 4B-D
FIGS. 4E-H
FIGS. 5A-C

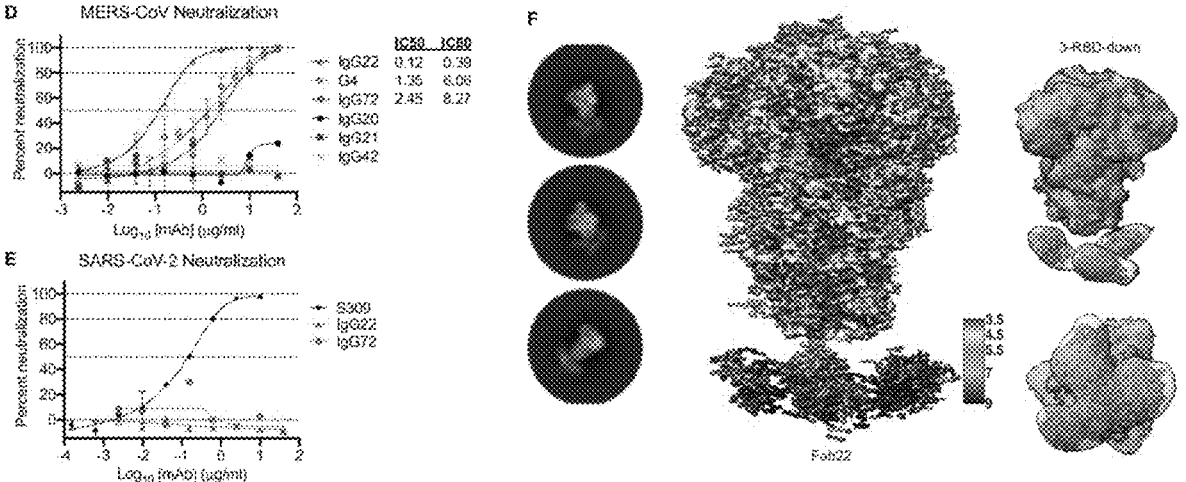
FIGS. 5D-F
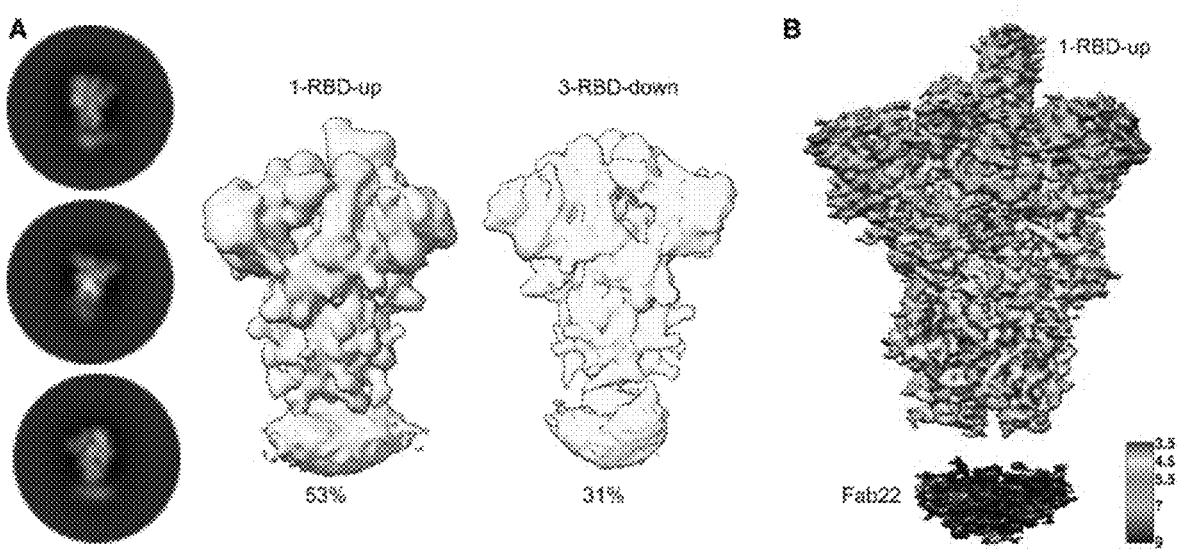
FIGS. 6A-B

C
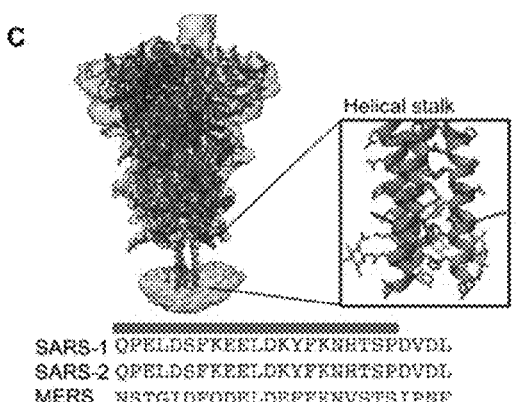
SARS-1 QPELDSFKEELDKYFKNRTSPDVDL
SARS-2 QPELDSFKEELDKYFKNRTSPDVDL
MERS   NSTGIDFQDELDEFFKNVSTSIPNF
HKU1   IPNLSDFKEELSLNFKNRTSIAPNL
D   Fab22 Binding to SARS-CoV-2 S Variants
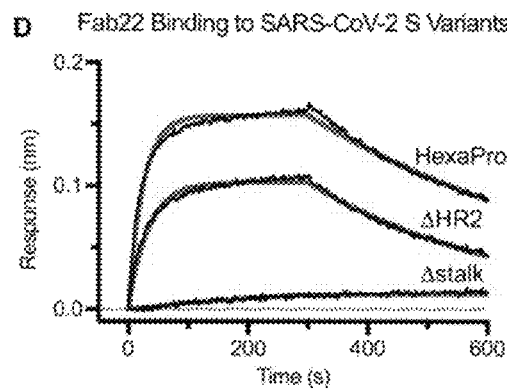
FIGS. 6C-D
A
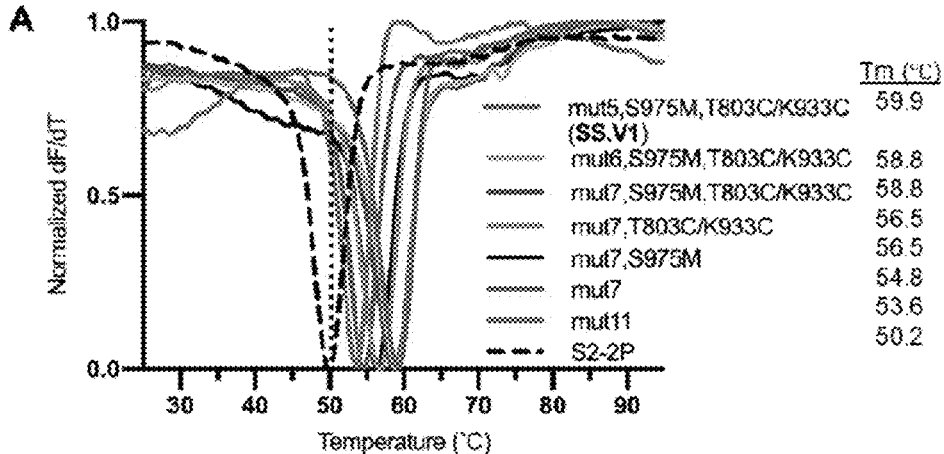
|  | Tm (°C) |
| --- | --- |
| mut5,S975M,T803C/K933C (SS,V1) | 59.9 |
| mut6,S975M,T803C/K933C | 58.8 |
| mut7,S975M,T803C/K933C | 58.8 |
| mut7,T803C/K933C | 56.5 |
| mut7,S975M | 56.5 |
| mut7 | 54.8 |
| mut11 | 53.6 |
| S2-2P | 50.2 |
FIG. 7A

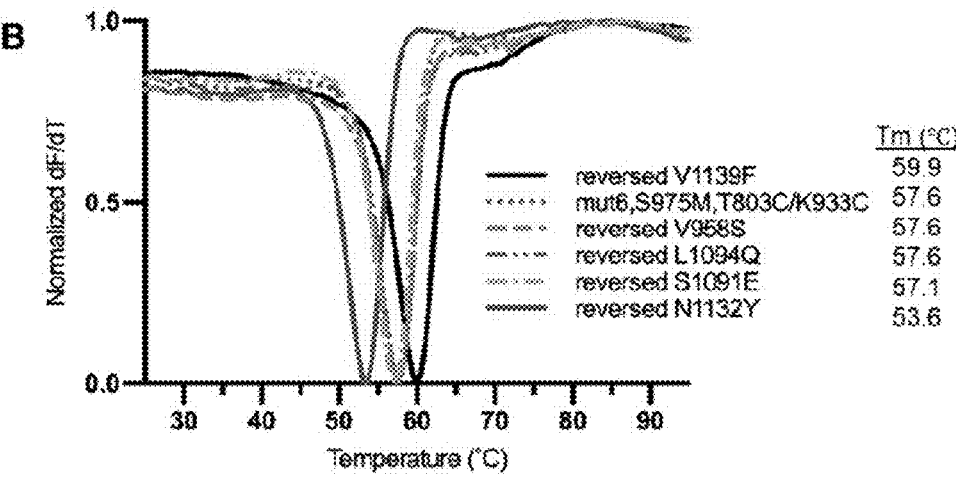
FIG. 7B
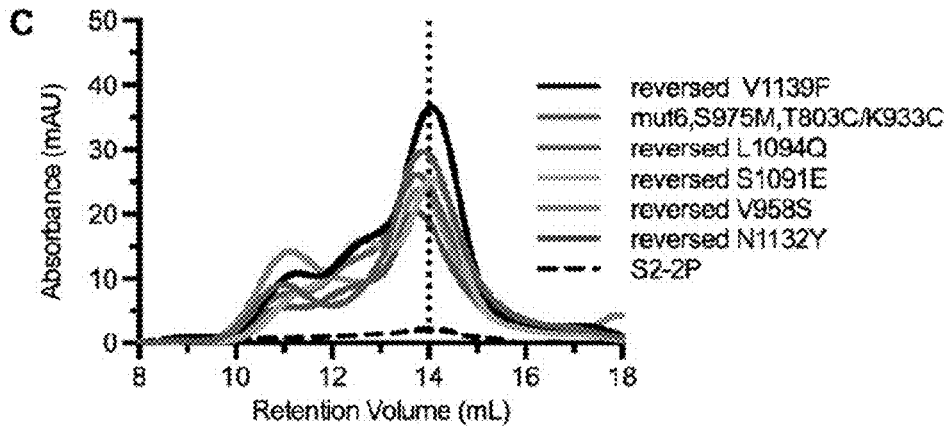
FIG. 7C
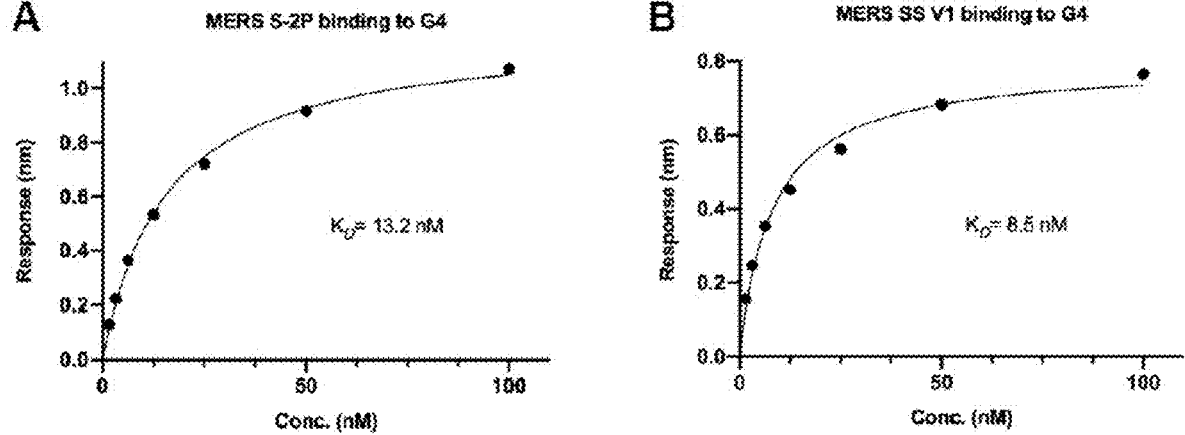
FIGS. 8A-B

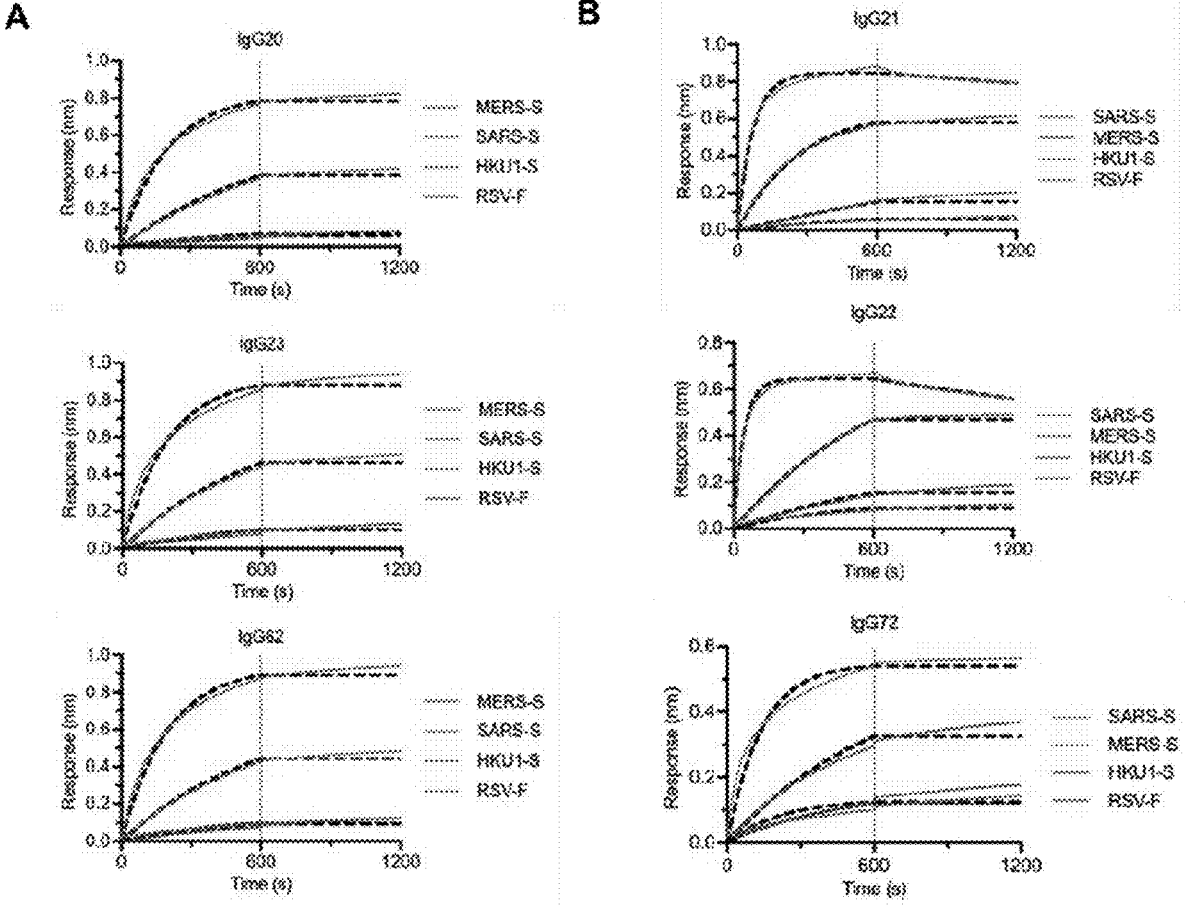
FIGS. 9A-B

A          Fab22 + MERS-CoV S
B          Fab72 + MERS-CoV S
C          Fab22 + SARS-CoV-2 S
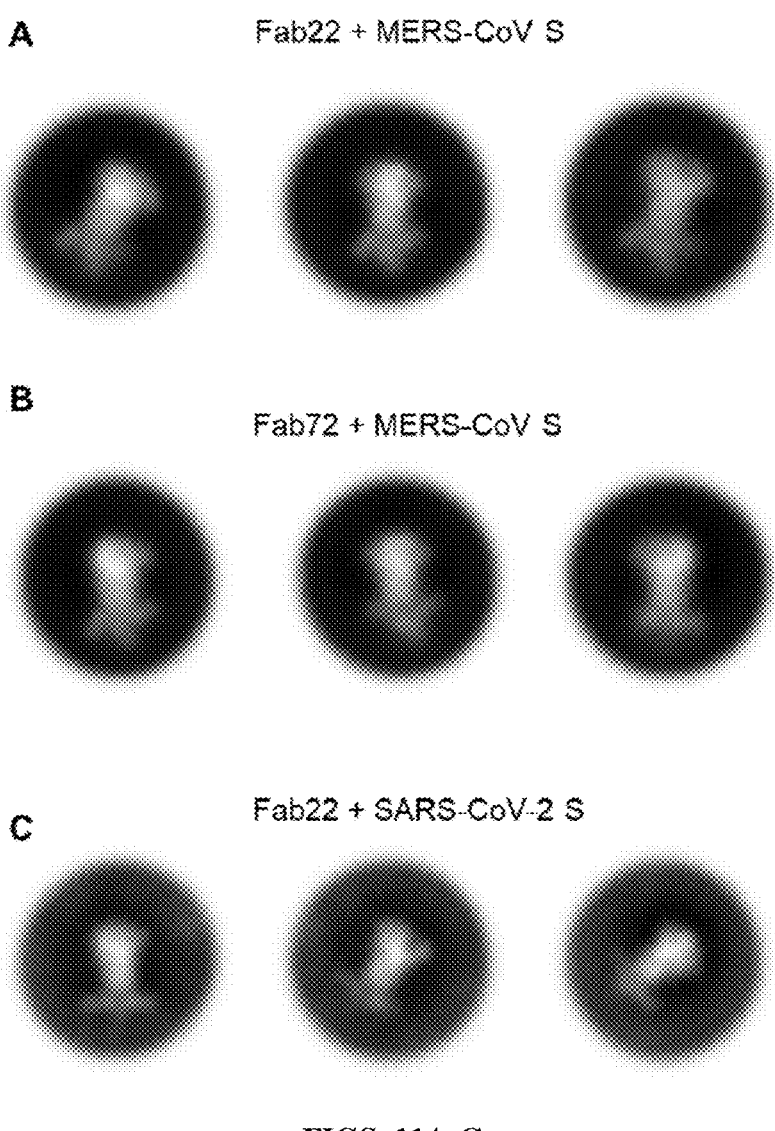
FIGS. 11A-C Reducing                Non-Reducing 1. HP-S2-30
2. HP-S2-30-del-stalk
3. HP-S2-30+60 (Q895P)
4. HP-S2-30+62 (Q957E)
5. HP-S2-30-HS3
6. HP-S2-30-HS5.V1
7. HP-S2-30-HS5.V2
8. HP-S2-30-HS5.V3
9. HP-S2-30-HS5.V4
10. HP-S2 (control)

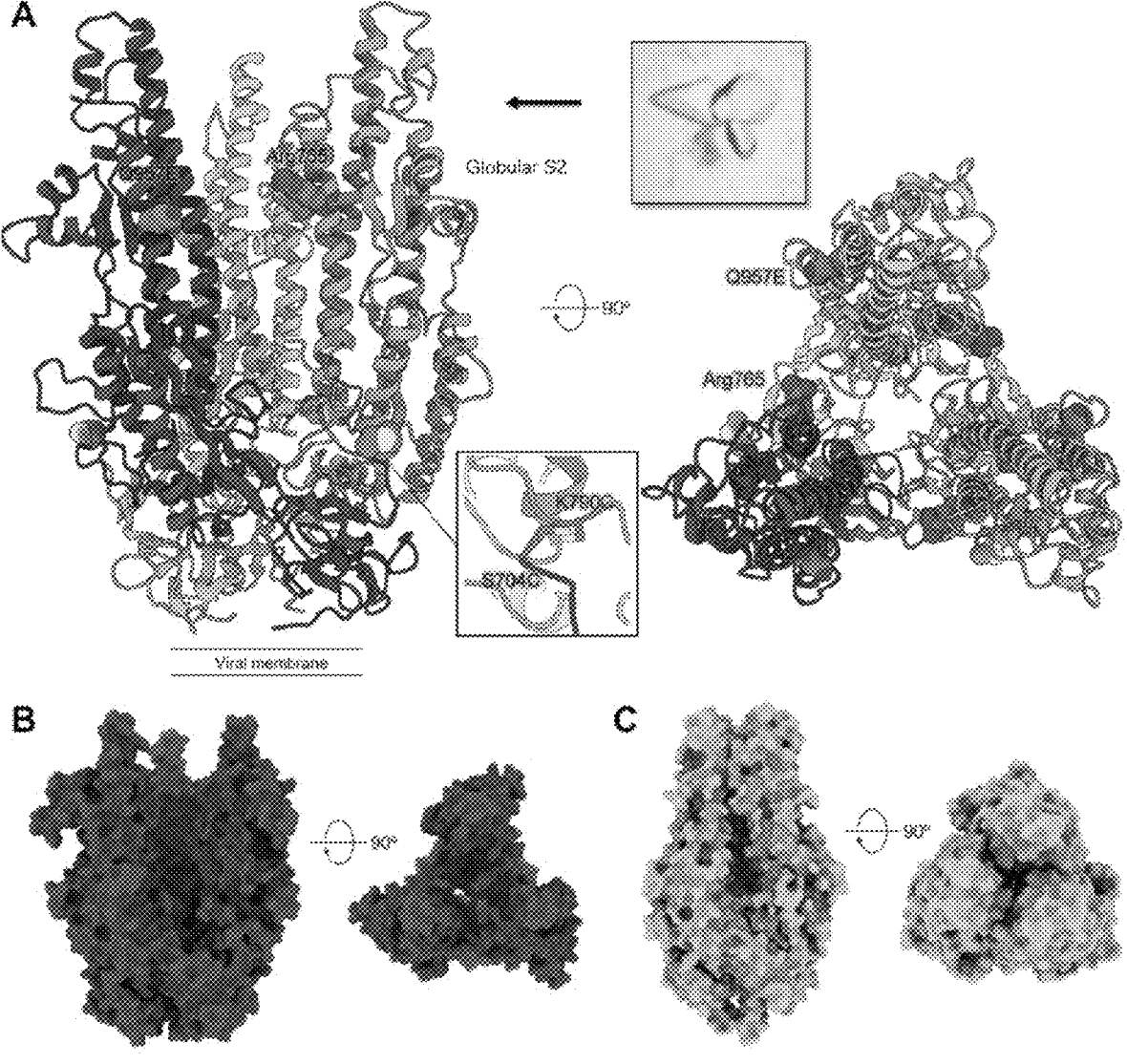
FIGS. 19A-C

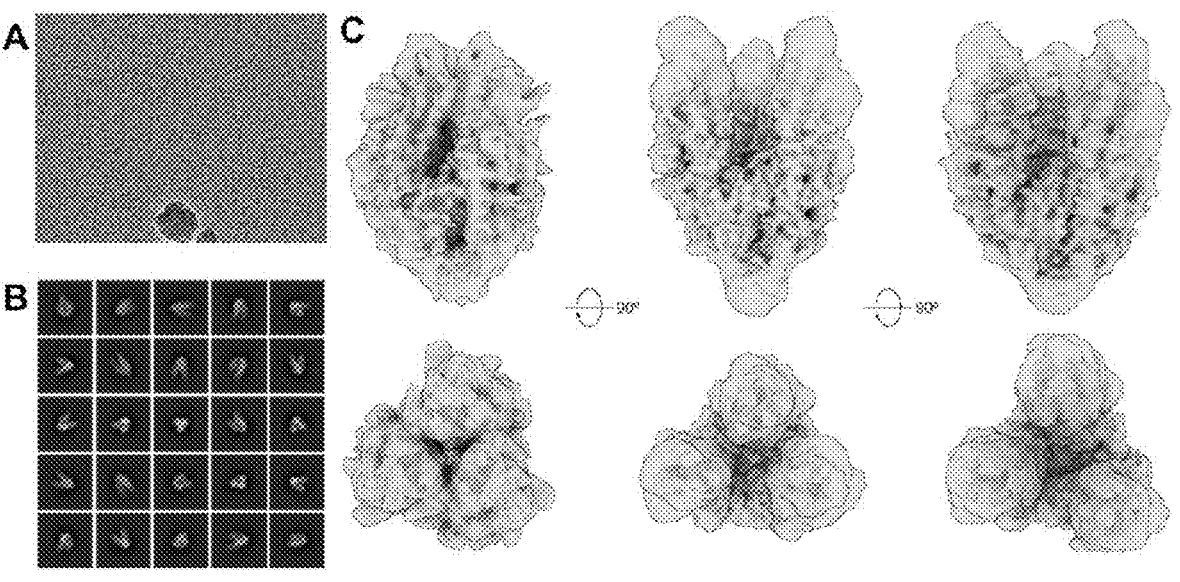
FIGS. 20A-C
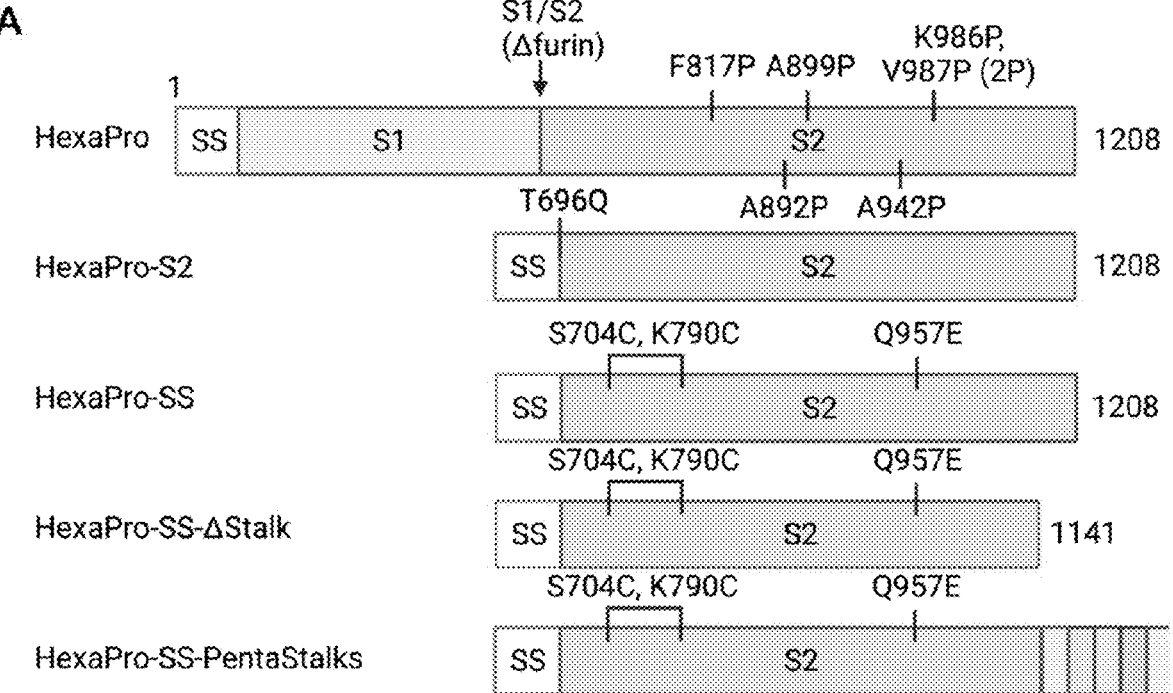
FIG. 21A

SEQUENCE LISTING

```
Sequence total quantity: 11
SEQ ID NO: 1            moltype = AA   length = 1353
FEATURE                 Location/Qualifiers
source                  1..1353
                        mol_type = protein
                        organism = Middle East respiratory syndrome-related
                        coronavirus
REGION                  762..1291
                        note = S2 domain
SEQUENCE: 1
MIHSVFLLMF LLTPTESYVD VGPDSVKSAC IEVDIQQTFF DKTWPRPIDV SKADGIIYPQ  60
GRTYSNITIT YQGLFPYQGD HGDMYVYSAG HATGTTPQKL FVANYSQDVK QFANGFVVRI  120
GAAANSTGTV IISPSTSATI RKIYPAFMLG SSVGNFSDGK MGRFFNHTLV LLPDGCGTLL  180
RAFYCILEPR SGNHCPAGNS YTSFATYHTP ATDCSDGNYN RNASLNSFKE YFNLRNCTFM  240
YTYNITEDEI LEWFGITQTA QGVHLFSSRY VDLYGGNMFQ FATLPVYDTI KYYSIIPHSI  300
RSIQSDRKAW AAFYVYKLQP LTFLLDFSVD GYIRRAIDCG FNDLSQLHCS YESFDVESGV  360
YSVSSFEAKP SGSVVEQAEG VECDFSPLLS GTPPQVYNFK RLVFTNCNYN LTKLLSLFSV  420
NDFTCSQISP AAIASNCYSS LILDYFSYPL SMKSDLSVSS AGPISQFNYK QSFSNPTCLI  480
LATVPHNLTT ITKPLKYSYI NKCSRFLSDD RTEVPQLVNA NQYSPCVSIV PSTVWEDGDY  540
YRKQLSPLEG GGWLVASGST VAMTEQLQMG FGITVQYGTD TNSVCPKLEF ANDTKIASQL  600
GNCVEYSLYG VSGRGVFQNC TAVGVRQQRF VYDAYQNLVG YYSDDGNYYC LRACVSVPVS  660
VIYDKETKTH ATLFGSVACE HISSTMSQYS RSTRSMLKRR DSTYGPLQTP VGCVLGLVNS  720
SLFVEDCKLP LGQSLCALPD TPSTLTPRSV RSVPGEMRLA SIAFNHPIQV DQLNSSYFKL  780
SIPTNFSFGV TQEYIQTTIQ KVTVDCKQYV CNGFQKCEQL LREYGQFCSK INQALHGANL  840
RQDDSVRNLF ASVKSSQSSP IIPGFGGDFN LTLLEPVSIS TGSRSARSAI EDLLFDKVTI  900
ADPGYMQGYD DCMQQGPASA RDLICAQYVA GYKVLPPLMD VNMEAAYTSS LLGSIAGVGW  960
```

```
TAGLSSFAAI PFAQSIFYRL NGVGITQQVL SENQKLIANK FNQALGAMQT GFTTTNEAFH  1020
KVQDAVNNNA QALSKLASEL SNTFGAISAS IGDIIQRLDV LEQDAQIDRL INGRLTTLNA  1080
FVAQQLVRSE SAALSAQLAK DKVNECVKAQ SKRSGFCGQG THIVSFVVNA PNGLYFMHVG  1140
YYPSNHIEVV SAYGLCDAAN PTNCIAPVNG YFIKTNNTRI VDEWSYTGSS FYAPEPITSL  1200
NTKYVAPQVT YQNISTNLPP PLLGNSTGID FQDELDEFFK NVSTSIPNFG SLTQINTTLA  1260
DLTYEMLSLQ QVVKALNESY IDLKELGNYT YYNKWPWYIW LGFIAGLVAL ALCVFFILCC  1320
TGCGTNCMGK LKCNRCCDRY EEYDLEPHKV HVH                                 1353

SEQ ID NO: 2              moltype = AA  length = 1273
FEATURE                   Location/Qualifiers
source                    1..1273
                          mol_type = protein
                          organism = Severe acute respiratory syndrome-related
                           coronavirus 2
REGION                    687..1208
                          note = S2 domain
SEQUENCE: 2
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                      1273

SEQ ID NO: 3              moltype = AA  length = 1255
FEATURE                   Location/Qualifiers
source                    1..1255
                          mol_type = protein
                          organism = Severe acute respiratory syndrome-related
                           coronavirus
REGION                    668..1190
                          note = S2 domain
SEQUENCE: 3
MFIFLLFLTL TSGSDLDRCT TFDDVQAPNY TQHTSSMRGV YYPDEIFRSD TLYLTQDLFL  60
PFYSNVTGFH TINHTFGNPV IPFKDGIYFA ATEKSNVVRG WVFGSTMNNK SQSVIIINNS  120
TNVVIRACNF ELCDNPFFAV SKPMGTQTHT MIFDNAFNCT FEYISDAFSL DVSEKSGNFK  180
HLREFVFKNK DGFLYVYKGY QPIDVVRDLP SGFNTLKPIF KLPLGINITN FRAILTAFSP  240
AQDIWGTSAA AYFVGYLKPT TFMLKYDENG TITDAVDCSQ NPLAELKCSV KSFEIDKGIY  300
QTSNFRVVPS GDVVRFPNIT NLCPFGEVFN ATKFPSVYAW ERKKISNCVA DYSVLYNSTF  360
FSTFKCYGVS ATKLNDLCFS NVYADSFVVK GDDVRQIAPG QTGVIADYNY KLPDDFMGCV  420
LAWNTRNIDA TSTGNYNYKY RYLRHGKLRP FERDISNVPF SPDGKPCTPP ALNCYWPLND  480
YGFYTTTGIG YQPYRVVVLS FELLNAPATV CGPKLSTDLI KNQCVNFNFN GLTGTGVLTP  540
SSKRFQPFQQ FGRDVSDFTD SVRDPKTSEI LDISPCSFGG SSEVAVLYQD VNCTDVSTAI  600
HADQLTPAWR IYSTGNNVFQ TQAGCLIGAE HVDTSYECDI PIGAGICASY HTVSLLRSTS  660
QKSIVAYTMS LGADSSIAYS NNTIAIPTNF SISITTEVMP VSMAKTSVDC NMYICGDSTE  720
CANLLLQYGS FCTQLNRALS GIAAEQDRNT REVFAQVKQM YKTPTLKYFG GFNFSQILPD  780
PLKPTKRSFI EDLLFNKVTL ADAGFMKQYG ECLGDINARD LICAQKFNGL TVLPPLLTDD  840
MIAAYTAALV SGTATAGWTF GAGAALQIPF AMQMAYRFNG IGVTQNVLYE NQKQIANQFN  900
KAISQIQESL TTTSTALGKL QDVVNQNAQA LNTLVKQLSS NFGAISSVLN DILSRLDKVE  960
AEVQIDRLIT GRLQSLQTYV TQQLIRAAEI RASANLAATK MSECVLGQSK RVDFCGKGYH  1020
LMSFPQAAPH GVVFLHVTYV PSQERNFTTA PAICHEGKAY FPREGVFVFN GTSWFITQRN  1080
FFSPQIITTD NTFVSGNCDV VIGIINNTVY DPLQPELDSF KEELDKYFKN HTSPDVDLGD  1140
ISGINASVVN IQKEIDRLNE VAKNLNESLI DLQELGKYEQ YIKWPWYVWL GFIAGLIAIV  1200
MVTILLCCMT SCCSCLKGAC SCGSCCKFDE DDSEPVLKGV KLHYT                    1255

SEQ ID NO: 4              moltype = AA  length = 1208
FEATURE                   Location/Qualifiers
REGION                    1..1208
                          note = SARS-CoV-2 ectodomain consensus sequence for
                           wild-type and variants
UNSURE                    5
                          note = L or F
UNSURE                    18
```

-continued

```
                      note = L or F
UNSURE                19
                      note = T or R
UNSURE                20
                      note = T or N
UNSURE                26
                      note = P or S
UNSURE                67
                      note = A or V
UNSURE                69
                      note = H or absent
UNSURE                70
                      note = V or absent
UNSURE                80
                      note = D or G or A
UNSURE                95
                      note = T or I
UNSURE                138
                      note = D or Y
UNSURE                142
                      note = G or D
UNSURE                143
                      note = V or absent
UNSURE                144
                      note = Y or absent
UNSURE                152
                      note = W or C
UNSURE                154
                      note = E or K
UNSURE                157
                      note = F or S or absent
UNSURE                158
                      note = R or G
UNSURE                190
                      note = R or S
UNSURE                211
                      note = N or absent
UNSURE                212
                      note = L or I
UNSURE                215
                      note = D or G
UNSURE                241
                      note = L or absent
UNSURE                242
                      note = L or absent
UNSURE                243
                      note = A or absent
UNSURE                253
                      note = D or G
UNSURE                339
                      note = G or D
UNSURE                371
                      note = S or L
UNSURE                373
                      note = S or P
UNSURE                375
                      note = S or F
UNSURE                417
                      note = K or N or T
UNSURE                440
                      note = N or K
UNSURE                446
                      note = G or S
UNSURE                452
                      note = L or R
UNSURE                477
                      note = S or N
UNSURE                478
                      note = T or K
UNSURE                484
                      note = E or K or Q or A
UNSURE                493
                      note = Q or R
UNSURE                494
                      note = S or P
UNSURE                496
                      note = G or S
UNSURE                498
                      note = Q or R
```

-continued

```
UNSURE            501
                  note = N or Y
UNSURE            505
                  note = Y or H
UNSURE            547
                  note = T or K
UNSURE            565
                  note = F or L
UNSURE            570
                  note = A or D
UNSURE            614
                  note = D or G
UNSURE            677
                  note = Q or H
UNSURE            679
                  note = N or K
UNSURE            681
                  note = P or H or R
UNSURE            701
                  note = A or V
UNSURE            716
                  note = T or I
UNSURE            764
                  note = N or K
UNSURE            791
                  note = T or I
UNSURE            796
                  note = D or Y
UNSURE            856
                  note = N or K
UNSURE            859
                  note = T or N
UNSURE            888
                  note = F or L
UNSURE            950
                  note = D or H or N
UNSURE            954
                  note = Q or H
UNSURE            969
                  note = N or K
UNSURE            981
                  note = L or F
UNSURE            1027
                  note = T or I
UNSURE            1071
                  note = Q or H
UNSURE            1118
                  note = D or H
UNSURE            1176
                  note = V or F
UNSURE            1191
                  note = K or N
source            1..1208
                  mol_type = protein
                  organism = synthetic construct
UNSURE            13
                  note = S or I
REGION            684..1205
                  note = S2 domain
UNSURE            156
                  note = E or absent
UNSURE            982
                  note = S or A
UNSURE            655
                  note = H or Y
UNSURE            145
                  note = Y or absent
SEQUENCE: 4
MFVFXVLLPL VSXQCVNXXX RTQLPXAYTN SFTRGVYYPD KVFRSSVLHS TQDLFLPFFS    60
NVTWFHXIXX SGTNGTKRFX NPVLPFNDGV YFASXEKSNI IRGWIFGTTL DSKTQSLLIV   120
NNATNVVIKV CEFQFCNXPF LXXXXHKNNK SXMXSXXXVY SSANNCTFEY VSQPFLMDLE   180
GKQGNFKNLX EFVFKNIDGY FKIYSKHTPI XXVRXLPQGF SALEPLVDLP IGINITRFQT   240
XXXLHRSYLT PGXSSSGWTA GAAAYYVGYL QPRTFLLKYN ENGTITDAVD CALDPLSETK   300
CTLKSFTVEK GIYQTSNFRV QPTESIVRFP NITNLCPFXE VFNATRFASV YAWNRKRISN   360
CVADYSVLYN XAXFXTFKCY GVSPTKLNDL CFTNVYADSF VIRGDEVRQI APGQTGXIAD   420
YNYKLPDDFT GCVIAWNSNX LDSKVXGNYN YXYRLFRKSN LKPFERDIST EIYQAGXXPC   480
NGVXGFNCYF PLXXYXFXPT XGVGXQPYRV VVLSFELLHA PATVCGPKKS TNLVKNKCVN   540
FNFNGLXGTG VLTESNKKFL PFQQXGRDIX DTTDAVRDPQ TLEILDITPC SFGGVSITP    600
GTNTSNQVAV LYQXVNCTEV PVAIHADQLT PTWRVYSTGS NVFQTRAGCL IGAEXVNNSY   660
```

```
ECDIPIGAGI CASYQTXTXS XRRARSVASQ SIIAYTMSLG XENSVAYSNN SIAIPXNFTI  720
SVTTEILPVS MTKTSVDCTM YICGDSTECS NLLLQYGSFC TQLXRALTGI AVEQDKNTQE  780
VFAQVKQIYK XPPIKDFGGF NFSQILPDPS KPSKRSFIED LLFNKVTLAD AGFIKQYGDC  840
LGDIAARDLI CAQKFXGLXV LPPLLTDEMI AQYTSALLAG TITSGWTXGA GAALQIPFAM  900
QMAYRFNGIG VTQNVLYENQ KLIANQFNSA IGKIQDSLSS TASALGKLQX VVNXNAQALN  960
TLVKQLSSXF GAISSVLNDI XXRLDKVEAE VQIDRLITGR LQSLQTYVTQ QLIRAAEIRA 1020
SANLAAXKMS ECVLGQSKRV DFCGKGYHLM SFPQSAPHGV VFLHVTYVPA XEKNFTTAPA 1080
ICHDGKAHFP REGVFVSNGT HWFVTQRNFY EPQIITTXNT FVSGNCDVVI GIVNNTVYDP 1140
LQPELDSFKE ELDKYFKNHT SPDVDLGDIS GINASXVNIQ KEIDRLNEVA XNLNESLIDL 1200
QELGKYEQ                                                         1208

SEQ ID NO: 5              moltype = AA  length = 1288
FEATURE                  Location/Qualifiers
REGION                   1..1288
                         note = SARS-Cov-2 ectodomain with trimerization domain and
                          tags at the C-terminus
REGION                   1..1208
                         note = SARS-CoV-2 Ectodomain
REGION                   1209..1288
                         note = Trimerization domain and tags
source                   1..1288
                         mol_type = protein
                         organism = synthetic construct
SEQUENCE: 5
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA 1020
SANLAATKMS ECVLGQSKRV DFCGKGYHLM SFPQSAPHGV VFLHVTYVPA QEKNFTTAPA 1080
ICHDGKAHFP REGVFVSNGT HWFVTQRNFY EPQIITTDNT FVSGNCDVVI GIVNNTVYDP 1140
LQPELDSFKE ELDKYFKNHT SPDVDLGDIS GINASVVNIQ KEIDRLNEVA KNLNESLIDL 1200
QELGKYEQGS GYIPEAPRDG QAYVRKDGEW VLLSTFLGRS LEVLFQGPGH HHHHHHSAW  1260
SHPQFEKGGG SGGGGSGGSA WSHPQFEK                                   1288

SEQ ID NO: 6              moltype = AA  length = 610
FEATURE                  Location/Qualifiers
REGION                   1..610
                         note = MERS-Cov S2 with trimerization domain and tags at
                          the C-terminus
REGION                   1..530
                         note = MERS-CoV S2 domain
REGION                   531..610
                         note = Trimerization domain and tags
source                   1..610
                         mol_type = protein
                         organism = synthetic construct
SEQUENCE: 6
IAFNHPIQVD QLNSSYFKLS IPTNFSFGVT QEYIQTTIQK VTVDCKQYVC NGFQKCEQLL   60
REYGQFCSKI NQALHGANLR QDDSVRNLFA SVKSSQSSPI IPGFGGDFNL TLLEPVSIST  120
GSRSARSAIE DLLFDKVTIA DPGYMQGYDD CMQQGPASAR DLICAQYVAG YKVLPPLMDV  180
NMEAAYTSSL LGSIAGVGWT AGLSSFAAIP FAQSIFYRLN GVGITQQVLS ENQKLIANKF  240
NQALGAMQTG FTTTNEAFHK VQDAVNNNAQ ALSKLASELS NTFGAISASI GDIIQRLDVL  300
EQDAQIDRLI NGRLTTLNAF VAQQLVRSES AALSAQLAKD KVNECVKAQS KRSGFCGQGT  360
HIVSFVVNAP NGLYFMHVGY YPSNHIEVVS AYGLCDAANP TNCIAPVNGY FIKTNNTRIV  420
DEWSYTGSSF YAPEPITSLN TKYVAPQVTY QNISTNLPPP LLGNSTGIDF QDELDEFFKN  480
VSTSIPNFGS LTQINTTLLD LTYEMLSLQQ VVKALNESYI DLKELGNYTY GSGYIPEAPR  540
DGQAYVRKDG EWVLLSTFLG RSLEVLFQGP GHHHHHHHHS AWSHPQFEKG GGSGGGGSGG  600
SAWSHPQFEK                                                        610

SEQ ID NO: 7              moltype = AA  length = 28
FEATURE                  Location/Qualifiers
source                   1..28
                         mol_type = protein
                         organism = synthetic construct
REGION                   1..28
                         note = Stalk HS3
```

-continued

```
SEQUENCE: 7
FQDELDEFFK NVSTFESELS HWFKNQTS                                                28

SEQ ID NO: 8           moltype = AA  length = 56
FEATURE                Location/Qualifiers
source                 1..56
                       mol_type = protein
                       organism = synthetic construct
REGION                 1..56
                       note = Stalk HS5.V1
SEQUENCE: 8
FKEELDQWFK NQTSFESELS HWFKNQTSFQ DELDEFFKNV STFQKEFDKF YKNLST               56

SEQ ID NO: 9           moltype = AA  length = 87
FEATURE                Location/Qualifiers
source                 1..87
                       mol_type = protein
                       organism = synthetic construct
REGION                 1..87
                       note = Stalk HS5.V2
SEQUENCE: 9
FKEELDQWFK NQTSFESELS HWFKNQTSGS GYIPEAPRDG QAYVRKDGEW VLLSTFLGSF          60
QDELDEFFKN VSTFQKEFDK FYKNLST                                               87

SEQ ID NO: 10          moltype = AA  length = 80
FEATURE                Location/Qualifiers
source                 1..80
                       mol_type = protein
                       organism = synthetic construct
REGION                 1..80
                       note = Stalk HS5.V3
SEQUENCE: 10
GGGLPDFKEE LDQWFKNQTS SGSLSDFESE LSHWFKNQTS GSGGIDFQDE LDEFFKNVST          60
GSGDYDFQKE FDKFYKNLST                                                       80

SEQ ID NO: 11          moltype = AA  length = 108
FEATURE                Location/Qualifiers
source                 1..108
                       mol_type = protein
                       organism = synthetic construct
REGION                 1..108
                       note = Stalk HS5.V4
SEQUENCE: 11
GGGLPDFKEE LDQWFKNQTS SGSLSDFESE LSHWFKNQTS GSGYIPEAPR DGQAYVRKDG          60
EWVLLSTFLG SGIDFQDELD EFFKNVSTGS GDYDFQKEFD KFYKNLST                       108
```

STABILIZED BETA-CORONAVIRUS ANTIGENS

REFERENCE TO RELATED APPLICATIONS

The present application claims the priority benefit of U.S. provisional application No. 63/285,548, filed Dec. 3, 2021, the entire contents of which are incorporated herein by reference.

STATEMENT REGARDING FEDERALLY SPONSORED RESEARCH

This invention was made with government support under Grant no. R01 AI127521 awarded by the National Institutes of Health. The government has certain rights in the invention.

REFERENCE TO A SEQUENCE LISTING

This application contains a Sequence Listing XML, which has been submitted electronically and is hereby incorporated by reference in its entirety. Said Sequence Listing XML, created on Nov. 30, 2022, is named UTSBP1294US_ST26.xml and is 50,214 bytes in size.

BACKGROUND

1. Field

The present disclosure relates generally to the fields of medicine, virology, immunology, and protein engineering. More particular, the disclosure relates to engineered protein comprising beta-coronavirus S protein ectodomains and the use thereof in drug design and vaccine formulation.

2. Description of Related Art

An outbreak of COVID-19, the disease caused by infection of the coronavirus SARS-CoV-2, began in December 2019 in China has resulted in millions of infections and more than 100 thousand deaths. Like the virus that caused the SARS outbreak several years prior, SARS-CoV, the SARS-CoV-2 virus use their spike proteins to bind host cellular receptor angiotensin-converting enzyme 2 (ACE2). The interaction between the receptor binding domain (RBD) of the spike glycoprotein and the full-length human ACE2 protein. Although the sequence and structure of the SARS-CoV-2 spike protein is a known (see, e.g., Wrapp et al. 2020) there remains a need for stabilized S proteins that could be used for identifying drug candidates and for stimulating an effective immune response to the S protein.

SUMMARY

In one embodiment, provided herein are engineered proteins comprising an engineered coronavirus S protein ectodomain that comprises a sequence at least 90% identical to: (a) positions 14-1208 of SEQ ID NO: 4; (b) positions 14-1160 of SEQ ID NO: 4; (c) positions 319-1208 of SEQ ID NO: 4; or (d) position 684-1205 of SEQ ID NO: 4, wherein the engineered protein comprises at least one substitution relative to the sequence of SEQ ID NO: 4 or 5, said at least one substitution being: P792C, S704C, K790C, A713C, L894C, Q755C, N969C, G757C, S968C, G891C, P1069C, S1030C, D1041C, G1035C, or V1040C. In some aspects, the engineered protein comprises at least one pair of substitutions, said at least one pair of substitutions being: Y707C/P792C, S704C/K790C, A713C/L894C, Q755C/N969C, G757C/S968C, G891C/P1069C, S1030C/D1041C, or G1035C/V1040C. In some aspects, the engineered protein further comprises a substitution of Y707C and/or T883C. In some aspects, the engineered protein further comprises a pair of substitutions, said at least one pair of substitutions being: Y707C/T883C.

In some aspects, the engineered protein further comprises an additional engineered disulfide bond, a cavity filling substitution, and/or a substitution that provides an electrostatic or polar interaction. In some aspects, the engineered protein further comprises: (i) a substitution at a position corresponding to: T724, T752, T778, T961, I1013, H1058, S735, T859, I770, A1015, L727, S1021, Q901, S875, T912, H1088, L1141, V1040, L966, A766, T778, L938, V963, V911, N1108, V705, A893, N703, A672, A694, A1080, I1132, P862, T859, T547, N978, T961, S758, Q762, D1118, S659, S698, R1039, V722, A930, A903, Q913, S974, D979, P728, V951, V736, L858, S884, A893, P807, S875, T791, A879, G799, A924, V826, A899, Q779, F817, L865, T866, A892, A899, T912, A570, V963; T874, S1055, V729, A1022, L894, A713, L828, H1058, L822, A1056, Q965, S1003, A972, Q992, I980, A1078, V1133, H1088, T1120, I870, S1055, T1117, D1139, T1116, Y1138, I896, G885, Q901, F1103, P1112, G889, L1034, E819, S1055, A972, I980, I1081, N1135, E819, Q1054, Q957, I1130, V1040, H1088, V1104, R1000, A944, T724, A944, S730, S730, G769, A893, Q895, K921, L922, N978, A942, G946, S975, A890, S1003; and/or (ii) a deletion corresponding to positions 829-851, 675-686, 673-684, 1161-1208, or 1142-1208; and/or (iii) a substitution of two amino acids for amino acid positions 673-686.

In some aspects, the engineered protein comprises an engineered disulfide bond comprising paired cysteine substitutions at positions corresponding to: S735C and T859C; I770C and A1015C; L727C and S1021C; V911C and N1108C; A672C and A694C; A1080C and I1132C; S659C and S698C; V722C and A930C; A903C and Q913C; S974C and D979C; P728C and V951C; V736C and L858C; S884C and A893C; P807C and S875C; T791C and A879C; G799C and A924C; A570C and V963C; T874C and S1055C; V729C and A1022C; L822C and A1056C; Q965C and S1003C; A972C and Q992C; I980C and Q992C; A1078C and V1133C; H1088C and T1120C; I870C and S1055C; T1117C and D1139C; T1116C and Y1138C; I896C and Q901C; G885C and Q901C; F1103C and P1112C; G889C and L1034C; E819C and S1055C; A972C and I980C; I1081C and N1135C; or E819C and Q1054C. In some aspects, the engineered protein comprises an engineered disulfide bond comprising paired cysteine substitutions at positions corresponding to: A903C and Q913C; S884C and A893C; T791C and A879C; Q965C and S1003C; or T1117C and D1139C. In some aspects, the engineered protein comprises an engineered disulfide bond comprising paired cysteine substitutions at positions corresponding to S884C and A893C.

In some aspects, the engineered protein further comprises at least one additional engineered disulfide bond. In some aspects, the engineered protein further comprises an engineered disulfide bond comprising paired cysteine substitutions at positions corresponding to T791C and A879C; or G799C and A924C.

In some aspects, the engineered protein comprises an engineered disulfide bond comprising paired cysteine substitutions at positions corresponding to A903C and Q913C. In some aspects, the engineered protein further comprises at least one additional engineered disulfide bond. In some aspects, the engineered protein further comprises an engineered disulfide bond comprising paired cysteine substitutions at positions corresponding to Q965C and S1003C; S884C and A893C; T791C and A879C; or G799C and A924C. In some aspects, the engineered protein further comprises an engineered disulfide bond comprising paired cysteine substitutions at positions corresponding to A903C and Q913C; and/or Q965C and S1003C.

In some aspects, the engineered protein comprises a cavity filling substitution at a position corresponding to: T724, I1013, H1058, Q901, S875, H1088, L1141, V1040, T778, L938, V963, R1039, V826, A899, Q779, L894, V1040, V1104, R1000, A944, S730, A890, D1118, or S1003. In some aspects, the engineered protein comprises a cavity filling substitution at a position corresponding to: T778, L938, V963, or H1088. In some aspects, the engineered protein comprises a cavity filling substitution selected from: T724M, I1013F, H1058W, Q901M, S875F, H1088W, L1141F, V1040F, T778L, L938F, V963L, R1039F, V826L, A899F, Q779M, L894F, H1058F, H1058Y, V1040Y, H1088Y, V1104I, R1000Y, R1000W, A944F, T724I, A944Y, S730L, A890V, D1118F, or S1003V. in some aspects, the cavity filling substitution is selected from: T778L, L938F, V963L, or H1088Y. In some aspects, the cavity filling substitution is at a position corresponding to L938. In some aspects, the engineered protein comprises a L938F substitution. In some aspects, the engineered protein further comprises a cavity filling substitution at a position corresponding to V963. In some aspects, the engineered protein comprises a V963L substitution.

In some aspects, the engineered protein comprises a proline substitution selected from: F817P, L865P, T866P, A892P, A899P, T912P, A893P, Q895P, K921P, L922P, N978P, A942P, G946P, or S975P. In some aspects, the engineered protein comprises a proline substitution selected from: F817P, A892P, A899P, or A942P. In some aspects, the engineered protein comprises the proline substitution F817P. In some aspects, the engineered protein further comprises an engineered disulfide bond. In some aspects, the engineered disulfide bond comprises paired cysteine substitutions at positions corresponding to S884C and A893C; or T791C and A879C. In some aspects, the engineered protein further comprises an engineered disulfide bond comprising paired cysteine substitutions at positions corresponding to S884C and A893C. In some aspects, the engineered protein further comprises an additional proline substitution at V987P and/or K986P. In some aspects, the engineered protein comprises a proline substitution A892P. In some aspects, the engineered protein further comprises an additional proline substitution at A942P; A899P; and/or F817P. In some aspects, the engineered protein further comprises at least two proline substations selected from A892P; A942P; A899P; and/or F817P. In some aspects, the engineered protein further comprises at least three proline substations selected from A892P; A942P; A899P; and/or F817P. In some aspects, the engineered protein comprises proline substations at A892P; A942P; A899P; and F817P. In some aspects, the engineered protein comprises a proline substitution A899P or T912P. In some aspects, the engineered protein comprises a proline substitution A892P and T912P.

In some aspects, the engineered protein comprises a substitution that provides an electrostatic interaction substitution at a position corresponding to T752, T912, L966, L828, S730, T961, A766, P862, T859, Q957, or G769. In some aspects, the engineered protein comprises an electrostatic interaction substitution at a position corresponding to T961, L966, T859, or G769. In some aspects, the engineered protein comprises an electrostatic interaction substitution of T961D or T961E. In some aspects, the engineered protein comprises a substitution of T961D. In some aspects, the engineered protein further comprises an L966E substitution. In some aspects, the engineered protein further comprises an electrostatic interaction substitution selected from: T752K, T912R, L828K, L828R, S730R, T961D, A766E, P862E, T859K, Q957E, or G769E. In some aspects, the engineered protein comprises an electrostatic interaction substitution selected from: T961D, L966D, T859K, or G769K.

In some aspects, the engineered protein comprises a substitution that provides an electrostatic or polar interaction substitution at a position corresponding T778, A713, or I1130. In some aspects, the engineered protein comprises an electrostatic interaction substitution selected from: T778Q, A713S, or I1130Y.

In some aspects, the engineered protein comprises a substitution that provides an electrostatic interaction substitution at a position and a F817P.

In some aspects, the engineered protein further comprises a substitution at a position corresponding to L984, D985, K986, and/or V987. In some aspects, the engineered protein further comprises a substitution at a position corresponding to L984, D985, K986, and/or V987 to glycine or proline.

In some aspects, the engineered protein further comprises the K986P and V987P substitutions.

In some aspects, the engineered protein further comprises a substitution a position corresponding to A570, T572, F855, and/or N856. In some aspects, the engineered protein further comprises a cavity-filling substitution at a position corresponding to A570, T572, F855, and/or N856.

In some aspects, the engineered protein comprises a combination of at least one engineered disulfide bond, at least one cavity filling substitution, at least one proline substitution, and at least one electrostatic interaction substitution.

In some aspects, the engineered protein comprises the following substitutions relative to the sequence of SEQ ID NO: 4 or 5: F817P, A892P, A899P, A942P, K986P, and V987P.

In some aspects, the engineered protein further comprises at least one substitution at a position corresponding to Q957, A895, G769, and/or G946 relative to SEQ ID NO: 4. In some aspects, the engineered protein further comprises at least one substitution selected from Q957E, A895P, G769E, and/or G946P relative to SEQ ID NO: 4. In some aspects, the engineered protein comprises the following substitutions relative to SEQ ID NO: 4: S704C/K790C and Q957E.

In some aspects, the engineered protein further comprises at least one substitution at a position corresponding F817, A892, A899, A942, K986, and/or V987 relative to SEQ ID NO: 4. In some aspects, the engineered protein further comprises at least one substitution selected from F817P, A892P, A899P, A942P, K986P, and/or V987P relative to SEQ ID NO: 4. In some aspects, the engineered protein comprises the following substitutions relative to SEQ ID NO: 4: F817P, A892P, A899P, A942P, K986P, V987P, and S704C/K790C. In some aspects, the engineered protein comprises the following substitutions relative to SEQ ID NO: 4: F817P, A892P, A899P, A942P, K986P, V987P, S704C/K790C, and Q957E.

In some aspects, the engineered coronavirus S protein ectodomain comprises a mutation that eliminates the furin cleavage site. In some aspects, the mutation that eliminates the furin cleavage site comprises a GSAS substitution at positions 682-685.

In some aspects, the engineered protein does not comprise an S1 domain.

In some aspects, the engineered protein comprises a sequence that has at least 95% identity to positions 687-1142 of SEQ ID NO: 4. In some aspects, the engineered protein further comprises a stalk region positioned C-terminally relative to the ectodomain, wherein the stalk region has a sequence comprising or consisting of a sequence at least 95% identical to the sequence of amino acid 1143-1208 of SEQ ID NO: 4. In some aspects, the engineered protein further comprises a stalk region positioned C-terminally relative to the ectodomain, wherein the stalk region has a sequence comprising or consisting of a sequence according to any one of SEQ ID NOs: 7-11.

In some aspects, the engineered protein is fused or conjugated to a trimerization domain. In some aspects, the engineered protein is fused to a trimerization domain. In some aspects, the trimerization domain is positioned C-terminally relative to the ectodomain or to the stalk region. In some aspects, the trimerization domain comprises a T4 fibritin trimerization domain.

In some aspects, the engineered protein is fused or conjugated to a transmembrane domain. In some aspects, the transmembrane domain comprises a beta-coronavirus spike protein transmembrane domain. In some aspects, the transmembrane domain comprises a homologous beta-coronavirus spike protein transmembrane domain. In some aspects, the transmembrane domain comprises a SARS-CoV-2 transmembrane domain.

In one embodiment, provided herein are engineered coronavirus trimers comprising at least one subunit according to any one of the present embodiments. In some aspects, the trimer is stabilized in a prefusion conformation relative to a trimer of wildtype S protein subunits. IN some aspects, the trimer is soluble. In some aspects, the trimer comprises at least one engineered disulfide bond between subunits. In some aspects, the at least one engineered disulfide bond between subunits is selected from: Y707C and P792C; Y707C and T883C; S704C and K790C; A713C and L394C; Q755C and N969C; G757C and S968C; G891C and P1069C; S1030C and D1041C; and G1035C and V1040C. In some aspects, the at least one engineered disulfide bond between subunits is selected: V705C and A983C; T547C and N968C; T961C and S758C; and/or T961C and Q762C.

In one embodiment, provided herein are pharmaceutical compositions comprising a pharmaceutically acceptable carrier; and (i) an engineered protein or (ii) an engineered trimer of any one of the present embodiments. In some aspects, the compositions further comprise an adjuvant.

In one embodiment, provided herein are nucleic acid molecules comprising a nucleotide sequence that encodes an amino acid sequence of an engineered protein of any one of the present embodiments. In some aspects, the nucleic acid comprises a DNA expression vector. In some aspects, the nucleic acid comprises a mRNA.

In one embodiment, provided herein are methods of preventing coronavirus infection or a disease associate with coronavirus infection in a subject, comprising administering to the subject an effective amount of the pharmaceutical composition or a nucleic acid molecule according to any one of the present embodiments. In some aspects, the method elicits a beta-coronavirus cross-reactive immune response. In some aspects, the method elicits the production of pan-coronavirus antibodies in the subject.

In one embodiment, provided herein are compositions comprising an engineered protein of any one of the present embodiments bound to an antibody.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIGS. 2A-H. Characterization of MERS stem stabilized spike variants. (FIG. 2A) SDS-PAGE of MERS-CoV S2-2P and single-substitution spike variants on mut11 backbone. Molecular weight standards are indicated at the left in kDa. (FIGS. 2B-D) Size-exclusion chromatography traces of purified spike variants, grouped by type (FIG. 2B, cavity and aromatic pi; FIG. 2C, disulfide; FIG. 2D polar and salt bridge). A vertical dotted line indicates the peak retention volume for S2-2P. (FIG. 2E) SEC traces for reversed and combinational-substitution spike variants. Mut5, mut6 and mut7 have six, five and four residues of mut11 reversed to the wild-type, respectively. S975M and T803C/K933C are additional mutations combined with mut5, mut6 and mut7. (FIG. 2F) SEC traces for combinatorial disulfide-substituted spike variants. Additional one or two disulfide substitutions are introduced on MERS SS.V1 backbone. (FIG. 2G) Differential scanning fluorimetry analysis of spike variant thermostability. The vertical dotted line indicates the apparent melting temperature for S2-2P. (FIG. 2H) SEC traces of MERS SS.V1 and MERS SS.V2 purified from a 1 L culture of FreeStyle 293F cells.

FIGS. 3A-F. Immunogenicity of MERS SS immunogens in mice. To assess immunogenicity of MERS SS immunogens, (FIG. 3A) BALB/cJ mice (n=10/group) were inoculated with PBS (gray), 1 μg of MERS S-2P (red), or 0.4, 2, or 10 μg of MERS SS.V1 (blue) or SS.V2 (green) adjuvanted with Sigma Adjuvant System (SAS). Mice were immunized at weeks 0 and 3 and bled two weeks post-boost for serological analyses including ELISAs to assess binding to (FIG. 3B) MERS-CoV, (FIG. 3C) HCoV-HKU1, (FIG. 3D) SARS-CoV and (FIG. 3E) SARS-CoV-2 S-2P-specific binding IgG and (FIG. 3F) MERS-CoV pseudovirus neutralization assay. Each circle represents an individual mouse. Dotted lines represent upper and lower limits of detection where applicable. (FIGS. 3B-F) Min to max box plots, with the box from 25-75% and the median value denoted by the line. (FIGS. 3B-E) Experimental groups were compared by two-way ANOVA with multiple comparisons post-test and (FIG. 3F) one-way ANOVA with groups Kruskal-Wallis multiple comparisons test. *=p-value <0.05, =p-value <0.01, *=p-value <0.001, ****=p-value <0.0001.

FIGS. 4A-D. Efficacy of SS.V1 against lethal MERS-CoV challenge in mice. (FIG. 4A) hDPP4 (288/330+/+) mice (n=20/group) were immunized at weeks 0, 3, and 9 with PBS (gray) or 10 μg of MERS-CoV S-2P (red) or SS.V1 (blue) adjuvanted with SAS. Two weeks post-boost, mice were bled for analysis of (FIG. 4B) MERS-CoV S-2P-specific IgG and (FIG. 4C) pseudovirus neutralizing antibodies. Four weeks post-boost, mice were challenged with a lethal dose of mouse-adapted MERS-CoV (MA35c5). (FIG. 4D) Following challenge, mice were monitored for weight loss. (FIGS. 4E-H) At days 3 and 5 post-challenge, a subset of mouse lungs (N=5/timepoint) was harvested for analysis of (FIGS. 4E-F) viral titers and (FIGS. 4G-H) hemorrhage (0=no hemorrhage, 4=severe hemorrhage in all lobes). (FIGS. 4B-C, E-H) Each circle represents an individual mouse. Min to max box plots, with the box from 25-75% and the median value denoted by the line. Dotted lines represent lower limits of detection where applicable. Experimental groups were compared by one-way ANOVA with Kruskal-Wallis post-test. (FIG. 4D) For weight loss, the mean of each group is represented by a circle, error bars represent SEM, and experimental groups was compared to the PBS-immunized group on each day post-challenge. *=p-value <0.05, =p-value <0.01, *=p-value <0.001, ****=p-value <0.0001.

FIGS. 5A-F. MERS stem-targeted mAbs neutralize authentic MERS-CoV. Binding of Fab22 to (FIG. 5A) MERS-CoV S, (FIG. 5B) SARS-CoV S, and (FIG. 5C) SARS-CoV-2 S assessed by surface plasmon resonance. Binding data are shown as black lines and the best fit to a 1:1 binding model is shown as red lines. (FIG. 5D) IgG22 and IgG72 demonstrated concentration-dependent neutralization of MERS-CoV infectivity. Other SS.V1 elicited mAbs shown lacked detectable neutralizing activity against MERS-CoV. mAbs IgG20, IgG22 and IgG72 were tested in duplicate, and remaining mAbs were tested once. Neutralizing mAb G4 was included as a positive control and tested in triplicate. (FIG. 5E) Neither IgG22 or IgG72 exhibited detectable neutralization of SARS-CoV-2. mAb S309, which neutralizes SARS-CoV-2, was included as a positive control. IgG22 and IgG72 were tested once, and S309 was tested in duplicate. (FIG. 5F) Representative 2D class averages and cryo-EM density map of Fab22 bound to MERS S-2P. The local resolution is depicted by a spectrum of rainbow color as a scale bar. The side view and top-down view of the smoothened maps indicate three distinct Fab density.

FIGS. 6A-D. Stem-targeted mAb 22 binds to helical stalk region of SARS-CoV-2 spike. (FIG. 6A) Representative 2D class averages and 3D reconstructions of Fab22 bound SARS-CoV-2 S. (FIG. 6B) Side view of cryo-EM density of Fab22 bound to SARS-CoV-2 S. The local resolution is depicted by a spectrum of rainbow color as a scale bar. Fab22 binds to the base of the spike. (FIG. 6C) Model of full-length wildtype SARS-CoV-2 spike (PDB: 6XR8) docked into EM map of Fab22 bound SARS-CoV-2 S. The spike is colored green, and the helical stalk is colored blue. Zoomed view of the helical stalk has side chains shown in blue and N-linked glycan shown in pink. Sequence alignments of the helical stalk region of four β-CoVs show high sequence similarity. (FIG. 6D) Binding of Fab22 to three spike variants captured by RBD-directed IgG is assessed by BLI. Binding data are shown as black lines and the best fit to a 1:1 binding model is shown as red lines.

FIGS. 7A-C. Characterization of MERS stem stabilized spike variants. (FIGS. 7A and B) DSF analysis for spike variant thermostability. (FIG. 7A) For reversed spike variants (the first and the second iterations), mut5, mut6 and mut7 have six, five and four residues of mut11 reverted to the wild-type, respectively. S975M and T803C/K933C are additional mutations combined with mut5, mut6 and mut7. The dotted line indicates the melting curve for S2-2P. (FIG. 7B) DSF analysis for reversed spike variants (the third iterations). The variants having the same Tm are indicated by a dot line, dash line, dash-single dotted line or dash-double dotted line for clarity. (FIG. 7C) SEC traces for reversed spike variants (the third iterations). A vertical dotted line indicates the peak retention volume for S2-2P. (FIGS. 7B-C) Each substitution in mut6,S975M,T803C/K933C backbone was respectively reversed to the wild-type residue.

FIGS. 8A-B. MERS S-2P and MERS SS.V1 exhibit nanomolar binding affinity to mAb G4. Binding of (FIG. 8A) MERS S-2P or (FIG. 8B) MERS SS.V1 to mAb G4 assessed by biolayer interferometry (BLI). AHC sensor tips were used to capture mAb G4 and then dipped into a well containing MERS S-2P or MERS SS in BLI buffer. The end-point binding responses were plotted against concentrations of the spikes, and the best fit by steady state analysis is shown as a nonlinear line.

FIGS. 9A-C. MERS SS.V1 elicited mAbs exhibit a spectrum of the binding specificities to betacoronavirus spikes. Binding of MERS SS.V1 elicited mAbs to MERS-CoV S, SARS-CoV S, HCoV-HKU1 S assessed by biolayer interferometry (BLI). RSV-F containing a consensus trimerization motif (foldon) is also included as a negative control. Binding data are shown as red lines (MERS-S), blue lines (SARS-S), green lines (HKU1-S), purple lines (RSV-F), and the best fit to a 1:1 binding model is shown as dash lines. A vertical dotted line indicates the end of the binding event. The selected mAbs are grouped by their binding kinetics: (FIG. 9A) bi-specificity, faster on rates to MERS-S than SARS-S (FIG. 9B) bi-specificity, faster on rates to SARS-S than MERS-S (FIG. 9C) only binding to MERS-S or only binding to foldon.

(FIG. 10A) Illustration of the scheme of experimental design for G4 competition assay by BLI. AHC biosensors were used to capture selected mAb and then dipped into G4 Fab pre-saturated MERS-S or apo MERS-S. Binding data are shown as pink lines (G4 Fab pre-saturated MERS-S) and blue lines (apo MERS-S) and the best fit to a 1:1 binding model is shown as dash lines. A vertical dotted line indicates the end of the binding event when the responses are used for end-point binding analysis. (FIG. 10B) End-point binding responses of mAbs to G4 Fab pre-saturated MERS-S versus MERS-S are calculated and shown as percentage. mAb G4 is also included as a control (white bar). Non-G4 competing mAbs having higher responses to G4 Fab pre-saturated MERS-S than MERS-S are depicted as green bars. G4 competing mAbs having higher responses to MERS-S than G4 Fab pre-saturated MERS-S are depicted as black bars.

FIGS. 11A-C. Fab22 and Fab72 bind to a helical stalk region of the spikes. (FIG. 11A) Representative 2D class averages of Fab22 complexed with MERS-CoV S by negative stain electron microscopy (nsEM). (FIG. 11B) Representative 2D class averages of Fab72 complexed with MERS-CoV S by nsEM. (FIG. 11C) Representative 2D class averages of Fab22 complexed with HexaPro, a prefusion stabilized SARS-CoV-2 S, by nsEM.

(FIG. 14A) SDS-PAGE of SARS-CoV-2 S2 designs with inter-protomer disulfide bonds. Molecular weight standards are indicated in kDa at the left. The arrow in the top gel (reducing) indicates the position of monomer. The upper and lower arrows in the bottom gel (non-reducing) indicate the position of trimer and monomer, respectively. (FIG. 14B) SEC traces for SARS-CoV-2 S2 designs with inter-protomer disulfide bonds. A vertical dotted line indicates the peak retention volume for HP. Y-axis is Absorbance (mAU); X-axis is Retention Volume (mL). (FIG. 14C) DSF analysis for SARS-CoV-2 S2 designs with inter-protomer disulfide bonds.

(FIG. 15A) SDS-PAGE of SARS-CoV-2 S2 designs with combinatorial inter-protomer disulfide bonds. Molecular weight standards are indicated in kDa at the left. The upper and lower arrows in the gel indicate the position of trimer and monomer, respectively. Reducing and non-reducing protein samples are loaded on the left side and the right side of the gel, respectively. Half amount of S2-30 sample is loaded on the left side and highlighted as an asterisk. (FIG. 15B) SEC traces for SARS-CoV-2 S2 designs with combinatorial inter-protomer disulfide bonds. A vertical dotted line indicates the peak retention volume for HP. Y-axis is Absorbance (mAU); X-axis is Retention Volume (mL). (FIG. 15C) DSF analysis for SARS-CoV-2 S2 designs with combinatorial inter-protomer disulfide bonds. X-axis is dF/dT; Y-axis is temperature in Celsius.

(FIG. 16A) Binding of Fab3A3 to S2-30 assessed by surface plasmon resonance. (FIG. 16B) Negative-stain EM images of S2-30 particles. (FIG. 16C) S2 trimer shown as a ribbon diagram.

(FIG. 17A) SEC traces for SARS-CoV-2 S2 designs with inter-protomer disulfide bonds and interprotomer salt bridges. (FIG. 17B) Ribbon diagram of S2-30+62. (FIG. 17C) SDS-PAGE of S2-30 with additional substitutions or modified stalks. Molecular weight standards are indicated at the left in kDa. (FIG. 17D) SEC traces for S2-30 with interpromoter salt bridges or modified stalks.

(FIG. 18A) Large scale expression of HexaPro, HP-S2 and S2-37. (FIG. 18B) Large scale expression of S2-37 delta stalk. (FIG. 18C) Large scale expression of S2-37 HS5.V1.

FIGS. 19A-C. Disulfide-stabilized S2 crystallized in an open prefusion conformation. (FIG. 19A) HexaPro-SS-Δstalk (S704C, K790C, Q957E with the stalk deleted) crystallized in space group R3 and a dataset was collected to a resolution of 3.2 A. The side (left) and top (right) view of the S2 trimer model are shown in ribbons. The cysteine substitutions (inset) from symmetry mates are in proximity to each other to form disulfide bonds, but Glu957 could not form a salt bridge with Arg765 from the neighboring protomer. (FIG. 19B) The side and top view of HexaPro-SS-Δstalk presents a prefusion conformation with trimer apex splayed open. (FIG. 19C) The surface representation of HexaPro (PDBID: 6XKL) with S1 subunit removed, exhibiting a closed prefusion conformation.

FIGS. 20A-C. CryoEM structure of disulfide-stabilized S2 reveals a range of flexibility at the trimer apex. (FIG. 20A) A representative micrograph and (FIG. 20B) 2D class averages of HexaPro-SS-Δstalk. (FIG. 20C) 3D heterogenous reconstructions of HexaPro-SS-Δstalk demonstrate three distinct conformations with the trimer apex closed (left), semiopen (middle) and fully open (right).

FIGS. 21A-B. Schemes of immunogenicity study. (FIG. 21A) The primary sequence of the immunogens with substitutions highlighted. (FIG. 21B) BALB/cAnNHsd mice were primed and boosted with 10 μg of respective immunogens. Serum was collected before prime, boost and challenge for assessing neutralization titers. Two-to-seven days after challenges, mouse body weight, nasal and lung viral titers and congestion scores were measured.

DETAILED DESCRIPTION

Figure 1:
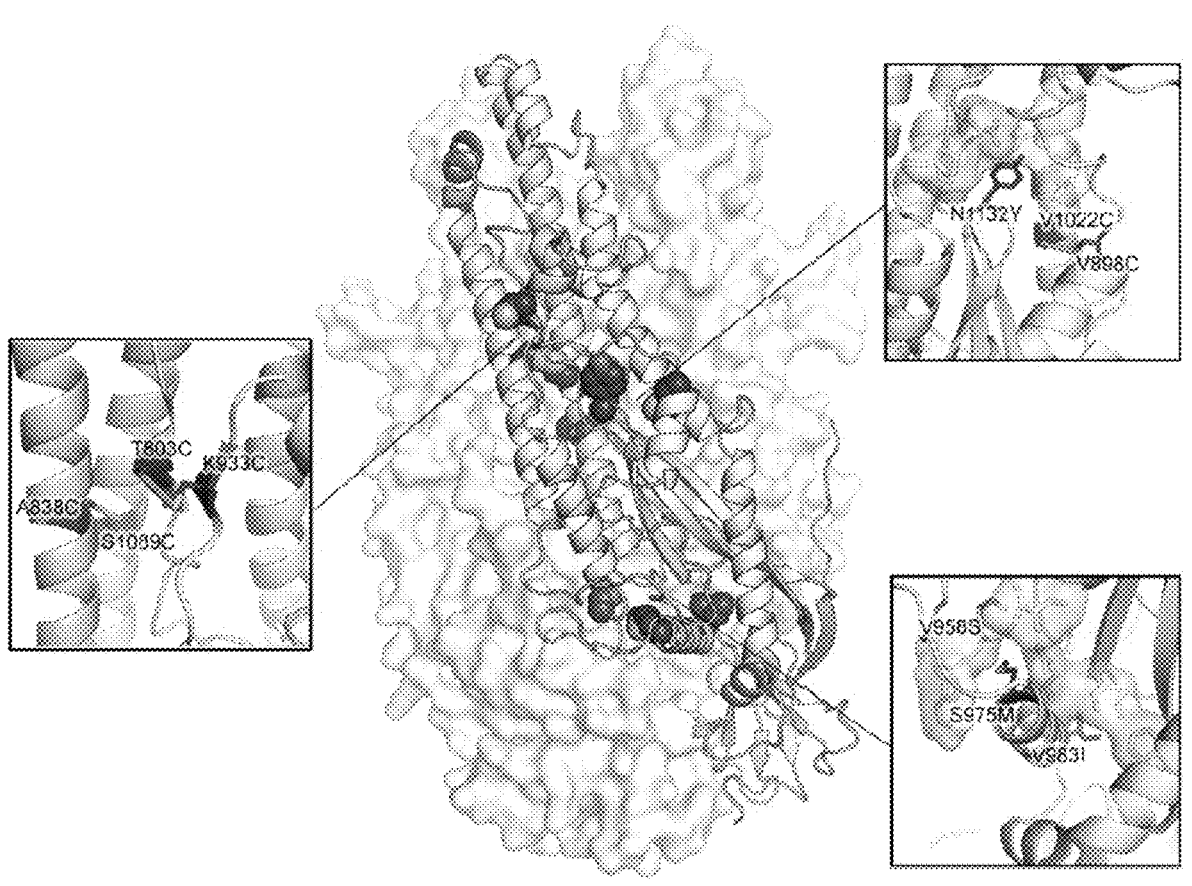
FIG. 1. Exemplary substitutions for MERS spike stem stabilization. Side view of the trimeric MERS-CoV globular spike ectodomain in a prefusion conformation (PDB ID: 5W9I) with S1 subunits omitted. One protomer of the S2 subunits is shown as a ribbon diagram with the other two protomers shown in a transparent molecular surface. The regions that refold during the pre-to-postfusion transition are colored cyan with the rest of the S2 in wheat. Each inset corresponds to the location of exemplary substitutions in the MERS SS.V1 construct.

Provided herein are engineered coronavirus spike proteins. In some aspects proteins of the embodiments are stabilized in a conformation present before membrane fusions. Such engineered proteins can be used, for example, to stimulate anti-coronavirus S protein specific immune response. In further aspects, engineered S proteins can be used to detect S protein binding antibodies in a sample. Thus, the engineered proteins provided herein allow for more effective method for vaccination against coronavirus as well as enabling new assay method for detecting anti-coronavirus antibodies, e.g., biological samples.

I. Coronavirus Spike Protein and Stabilized Stem S2

The spike protein of SARS-CoV-2 plays an essential role in virus entry into host cells and thus a primary target by neutralizing antibodies. The spike protein comprises an N-terminal S1 subunit and a C-terminal S2 subunit, which are responsible for receptor binding and membrane fusion. The S1 subunit is further divided into the N-terminal domain, the receptor-binding domain (RBD), the subdomain 1 (SD1) and subdomain 2 (SD2), and the S2 subunit is further divided into the fusion peptide (FP), the heptad repeat 1 (HR1) and heptad repeat 2 (HR2). The spike binds to a cellular receptor through its RBD, which triggers a conformational change of the spike. The activated spike is cleaved by a protease (such as TMPRSS2 for SARS-CoV and SARS-CoV-2) at S1/S2 site to release the S1 subunit and expose the FP on S2 subunit. The HR1 and HR2 refold to the post-fusion conformation to drive membrane fusion 35. Due to the functionality and a higher immunogenicity of the S1, most neutralizing antibodies characterized for coronavirus to date target the S1 subunit. A major challenge is that the S2 conformation is highly dynamic during membrane fusion, making it difficult to prepare the spike protein antigen and generate effective immune responses against spike (e.g., produce neutralizing antibodies). Spike protein stabilizing strategies have been demonstrated by mutation of the spike protein coding sequence (see mutations provided in Table 1; see Hsieh et al., 2020, which is incorporated herein by reference in its entirety). Additional inter-protomer disulfide bond designs are provided in Table 1.

Any of the substitutions described herein may engineered into any known coronavirus S protein variant, including, but not limited to, a coronavirus S protein having any one or more of the following modifications (see SEQ ID NO: 4): L5F, S13I, L18F, T19R, T20N, P26S, Q52R, A67V, H69del, V70del, V70I, D80A, T95I, D138Y, Y144del, Y144V, W152C, E154K, R190S, D215G, L242del, A243del, L244del, D253G, W258L, K417N, K417T, L452R, S477N, T478K, E484K, E484Q, E484K, N501Y, A570D, D614G, H655Y, Q677H, P681R, P681H, A701V, T716I, F888L, D950N, S982A, T1027I, D1118H, and V1176F. Exemplary combinations of such modifications are provided in Table 2.

All CoV spikes are composed of an S1 subunit, a major determinant for host cell tropism, and an S2 subunit, which contains the machinery that drives viral-host fusion (Li, 2016; Siebert et al., 2003). The S1 subunit, which directly interacts with the host receptor, is composed of an N-terminal domain (NTD), a receptor-binding domain (RBD) and subdomains (SDs). For SARS-CoV-2, transient hinging of the RBD into an 'up' conformation allows for host-cell receptor engagement. In the S2 subunit, a helix-loop region spanning from the fusion peptide (FP) to heptad repeat 1 (HR1), constitutes a metastable structure that transitions to a long stable α-helix in the postfusion conformation during viral entry. The FP, HR1, central helix (CH) and connector domain (CD) comprise the globular head of the S2 subunit. In contrast, the helical stalk region, connecting the globular head to the viral membrane, is elongated and highly flexible (Ke et al., 2020; Turoňová et al., 2020). The stalk region can be further divided into a hip, knee, and ankle, wherein the knee functions as a hinge, providing a considerable range in flexibility and movement for the spikes on the viral surface. As the S1 is responsible for interacting directly with the host receptor, the majority of vaccine-induced antibodies and antibodies elicited upon natural infection target this subunit, most notably the RBD (Corbett et al., 2020b, 2020a; Jackson et al., 2020). In addition, a portion of neutralizing monoclonal antibodies (mAbs) isolated from convalescent COVID-19 patients recognize the NTD (Chi et al., 2020; Liu et al., 2020). Amino acid changes are concentrated in the S1 subunit among the majority of SARS-CoV-2 variants described thus far. Additionally, recent data suggest that antibodies in convalescent sera that target neutralization-sensitive epitopes in the S1 domain induce a selective pressure that yields escape mutations in these epitopes (Andreano et al., 2020).

The S2 subunit of CoV S, analogous to HA2 of influenza virus HA and gp41 of HIV-1 Env, functions as a fusogen by bringing viral and host cell membranes together, thus enabling viral entry. To complete fusion, the S2 subunit transitions from a metastable prefusion to a highly stable 250 post-fusion conformation (Li, 2016). The introduction of stabilizing mutations into the S2 subunit of MERS-CoV, SARS-CoV and SARS-CoV-2 permitted production of large quantities of prefusion stabilized trimeric full-length S retaining well-folded 3D structures resembling native S on the virion surface (Hsieh et al., 2020; Ke et al., 2020; Kirchdoerfer et al., 2018; Pallesen et al., 2017; Turoňová et al., 2020; Wrapp et al., 2020). Importantly, neutralization-sensitive epitopes and host receptor-binding sites in the S1 subunit were completely preserved. Collectively, the strategy of stabilizing S through engineered prevention of S2 refolding has been successful for generating vaccine antigens that protect animals in CoV-challenge models and humans from SARS-CoV-2 infection (Baden et al., 2020; Corbett et al., 2020a, 2020b; Polack et al., 2020).

Efforts toward a universal influenza A virus (IAV) vaccine yielded the first proof-of-concept for exploiting antigenic conservation in the hemagglutinin stem (HA stem) region (functionally analogous to the CoV S2 subunit) to elicit broad protection in animals. Specifically, two independent research groups rationally engineered the HA stem by introducing disulfide bridges, increasing surface hydrophilicity, stabilizing the hydrophobic core, optimizing the protease cleavage site, and/or displaying the HA stem on nanoparticles (Impagliazzo et al., 2015; Yassine et al., 2015). The HA stem trimers stabilized in the prefusion conformation induced neutralizing antibodies targeting stems of various group 1 HA subtypes and protected animals from heterotypic IAV challenge. A similar strategy based on structure-guided vaccine design was successfully applied to more distantly related group 2 IAV (Boyoglu-Barnum et al., 2020; Corbett et al., 2019).

A structure-guided design strategy has been used to generate MERS-CoV S2-only antigens, with the intention of eliciting cross-reactive antibodies against conserved S2 epitopes. Using the PROSS server (Goldenzweig et al., 2016) to identify candidate stabilizing mutations and biochemical analyses to down-select expressed S2 mutant proteins, two S2 subunit constructs optimized for stability, conformational fidelity, and product yields were identified as immunogens. Intra-protomer disulfide bonds were the most effective means of enhancing protein expression and thermostability. The Cys803-Cys933 pair was introduced to cross-link regions of mobility and immobility during the pre- to post-fusion transition in a manner similar to the Cys155-Cys290 substitution in RSV F (DS-Cav1) (McLellan et al., 2013). In addition, a covalent linkage was made across the S2' protease cleavage site, via the formation of a Cys838-Cys1089 bridge, akin to the Cys93(HA2)-Cys310 (HA1) substitution in the HA stem (Impagliazzo et al., 2015). Finally, Cys898 and Cys1022 substitutions were placed in the fusion peptide and HR1 to prevent the helix-loop region from transitioning to a single, elongated helix. Both Cys898 and Cys1022 substitutions were at regions that move substantially, and a similar approach was employed to increase the trimer fraction of HA stem (Cys68-Cys76) and to keep PIV3 F in a prefusion conformation (Cys162-Cys168) (Impagliazzo et al., 2015; Stewart-Jones et al., 2018). Disulfide engineering has also been used to restrict local flexibility of secondary structures in SARS-CoV-2 S (Hsieh et al., 2020) or to trap the RBDs in a closed configuration (Henderson et al., 2020; McCallum et al., 2020; Xiong et al., 2020). Most importantly, MERS SS V2 elicited 10-fold higher neutralizing antibodies against MERS CoV than SS V1 in a single prime-boost immunization regimen. Each disulfide substitution significantly improved thermostability of the MERS SS antigens, consistent with disulfide designs in other class I viral fusion proteins.

The cavity-filling approach proved to be successful in stabilizing loosely packed regions of RSV F in its prefusion conformation (Krarup et al., 2015; McLellan et al., 2013). This tactic was used in the optimization of a stable S2-only MERS immunogen by substituting Ser975 and Val983 with Met and Ile, respectively, at the base of MERS-CoV SS. These changes neatly filled a hydrophobic pocket between HR1 and amino acids that remain stationary during the pre- to post-fusion transition. A lone S975M change proved to be the most effective, leading to more than 10-fold increase in protein yields relative to the parental molecule. Similarly, N1132Y substitution seems to pack against Pro937, Val1206, and Pro1131 and possibly forms H bonds with Gln800 and Asn1029. Other modifications intended to enhance polar interactions—for instance, V958S, S1091E and L1094Q substitutions—were considered as beneficial additions to the best construct. Alternative strategies, such as stabilizing proline substitutions, reducing hydrophobicity at the S1-S2 interface, and nanoparticle display, are viable options to further improve our MERS SS.V2 antigens in efforts to induce cross-neutralizing antibodies.

MERS SS-immunization stimulated the production of antibodies that were cross-reactive to multiple CoV S proteins. This disclosure is the first to show protection against lethal CoV challenge with a stem-only immunogen—protection that comes without elicitation of potent neutralizing antibody responses. Previous studies suggest that in vivo activity of influenza virus stem-specific antibodies rely on Fc-mediated functions (DiLillo et al., 2014, 2016). In fact, only a handful of S2-specific neutralizing antibodies against MERS-CoV have been defined (Wang et al., 2015; Widjaja et al., 2019). One of these, murine mAb G4, protects against challenge in a murine lethal model of MERS-CoV infection and binds a hypervariable loop containing a unique N-glycosylation site in the connector domain (Pallesen et al., 2017; Wang et al., 2018). Roughly one third of SS-cross-reactive antibodies compete with G4 Fab for the loop epitope. Deletion of the highly immunogenic loop from an S2 subunit vaccine might be advantageous to prevent natural immunofocusing on an epitope poorly conserved among even closely related lineage C β-HCoVs.

This disclosure also describes a conserved epitope near the base of S, distinct from the G4-binding site. Two antibodies that recognize this epitope, IgG22 and IgG72, display heterotypic binding to all highly pathogenic β-HCoVs. Both antibodies neutralize authentic MERS-CoV and at low nM concentrations in the case of IgG22. However, IgG72 demonstrated markedly reduced neutralizing activity against MERS-CoV as compared to IgG22 (approximately a 10-fold reduction in inhibitory titer). Sequence alignments of Fab22 and Fab72 reveal only four amino acid differences, one in CDR-L3 and three in CDR-H2, plausibly explaining shared binding profiles for HCoV S proteins. Cryo-EM structures of Fab22 complexed with MERS S-2P and prefusion-stabilized SARS-CoV-2 S (HexaPro) revealed the Fab binding site in proximity to the helical stalk. Although the binding interface was incompletely resolved, the target site was localized to a region upstream of HR2. These residues dramatically refold to form a six-helical bundle with HR1, leading to virus-cell fusion. The faster (nearly 100-fold) dissociation rate of Fab22 for HexaPro (and SARS-CoV S-2P) compared to MERS-CoV S-2P provides an explanation for the undetectable heterotypic neutralizing activity by IgG22 (and IgG72). Similar antibodies have been recently described (Sauer et al., 2021; Wang et al., 2020), although in these cases sequential immunization was employed using full-length spikes from divergent β-CoVs to induce a response to the conserved S2.

In summary, this disclosure provides rationally engineered CoV S stems as stabilized immunogens to elicit antibodies cross-reactive with all three epidemic β-HCoVs and to provide complete protection in animals against a lethal MERS-CoV challenge. Using a stabilized stem construct, the production of antibodies was elicited which enabled the identification of a novel site of vulnerability in the S2 subunit, which will inform development of next-generation CoV vaccines and fortify CoV pandemic preparedness.

TABLE 1

| Spike protein substitutions and mutations | | |
|---|---|---|
| Designation | Mutations (relative to SEQ ID NO: 4) | Strategy |
| | Y707C/P792C | Inter-protomer disulfide bond |
| | Y707C/T883C | Inter-protomer disulfide bond |
| | S704C/K790C | Inter-protomer disulfide bond |
| | A713C/L894C | Inter-protomer disulfide bond |
| | Q755C/N969C | Inter-protomer disulfide bond |
| | G757C/S968C | Inter-protomer disulfide bond |
| | G891C/P1069C | Inter-protomer disulfide bond |
| | S1030C/D1041C | Inter-protomer disulfide bond |
| | G1035C/V1040C | Inter-protomer disulfide bond |
| | A846P | Proline |
| | V1065F | Cavity filling |
| | A1020Q | Polar |
| | H1058Y | Cavity filling |
| | L752R | Salt bridge |
| | G946Q | Polar |
| | E1072Y | Cavity filling |
| | N777E | Salt bridge |
| | S735C/T859C | Disulfide bond |
| | V736C/L858C | |
| | T791C/A879C | Disulfide bond |
| | Q901M | Cavity filling |
| | L849K/L959E | Salt bridge |
| | P863F/L865K | Cavity filling |
| | L849W/L959F | Cavity filling |
| | T719D/S929K | Salt bridge |
| | V772E | Salt bridge |
| | S704C/K790C | Disulfide bond |
| | R1016R | Salt bridge |
| | K986P | Proline |
| | V987P | Proline |
| | V826C/L948C/Q949C | Disulfide bond |
| | N777C/A1022C | Disulfide bond |
| | I770C/A1015C | Disulfide bond |

TABLE 1-continued

Spike protein substitutions and mutations

| Designation | Mutations (relative to SEQ ID NO: 4) | Strategy |
|---|---|---|
| HP | F817P/A892P/A899P/A942P/K986P/V987P | |
| HP-S2 | HP Δ1-695 + T696Q with N terminal artificial signal peptide MRPTWAWWLFLVLLLALWAPARGAS | |
| S2-28 | HP-S2 + Y707C/P792C | Interprotomer Disulfide bond |
| S2-29 | HP-S2 + Y707C/T883C | Interprotomer Disulfide bond |
| S2-30 | HP-S2 + S704C/K790C | Interprotomer Disulfide bond |
| S2-31 | HP-S2 + A713C/L894C | Interprotomer Disulfide bond |
| S2-32 | HP-S2 + Q755C/N969C | Interprotomer Disulfide bond |
| S2-33 | HP-S2 + G757C/S968C | Interprotomer Disulfide bond |
| S2-34 | HP-S2 + G891C/P1069C | Interprotomer Disulfide bond |
| S2-35 | HP-S2 + S1030C/D1041C | Interprotomer Disulfide bond |
| S2-36 | HP-S2 + G1035C/V1040C | Interprotomer Disulfide bond |
| S2-62 | HP-S2 + Q957E | Salt bridge |
| S2-60 | HP-S2 + A895P | Proline |
| S2-50 | HP-S2 + G769E | Salt bridge |
| S2-61 | HP-S2 + G946P | Proline |
| S2-30 Δstalk | S2-30 Δ1142-1208 | |
| S2-30 HS5.V1 | S2-30 with 1162-1208 replaced with SEQ ID NO: 8 | |
| S2-37 | HP-S2 + Q957E + S704C/K790C | |
| S2-37 Δstalk | S2-30 Δ1142-1208 | |
| S2-37 HS5.V1 | S2-37 with 1162-1208 replaced with SEQ ID NO: 8 | |
| 2P | K986P/V987P | |
| mut5 | S884S/A1020Q/H1058Y/K986P/V987P | |
| mut7 | A846P/V1065F/A1020Q/H1058Y/K986P/ V987P | |
| mut11 | A846P/V1065F/A1020Q/H1058Y/L752R/ G946Q/E1072Y/K986P/V987P | |
| SS.V1 | Q901M/[S735C/T859C or V736C/L858C]/A1020Q/H1058Y/K986P/ V987P | |
| SS.V2 | Q901M/[S735C/T859C or V736C/L858C]/A1020Q/H1058Y/K986P/ V987P/V826C/L948C/Q949C/I770C/A1015C | |
| CL-1 | T724M | Cav |
| CL-2 | T752K | salt bridge |
| CL-3 | T778Q | H bond |
| CL-4 | T961D | salt bridge (inter-prot) |
| CL-5 | I1013F | Cav |
| CL-6 | H1058W | Cav |
| CL-7 | S735C, T859C | DS |
| CL-8 | I770C, A1015C | DS |
| CL-9 | L727C, S1021C | DS |
| CL-10 | Q901M | Cav (at the expense of H bond) |
| CL-11 | S875F | Cav |
| CL-12 | T912R | salt bridge |
| CL-13 | H1088W | Cav |
| CL-14 | L1141F | Cav |
| CL-15 | V1040F | Cav |
| CL-16 | L966D | salt bridge |
| CL-17 | A766E | salt bridge (inter-prot) |
| CL-18 | del(829-851) | remove flexible region |
| CL-19 | T778L | Cav |
| CL-20 | L938F | Cav |
| CL-21 | V963L | Cav |
| CL-22 | V911C, N1108C | DS |
| CL-23 | V705C-A893C | DS (inter-prot), introduce N-glycan |
| CL-24 | N703Q/V705C-A893C | DS (inter-prot) |
| CL-25 | replace (673-686) with GS | remove flexible region |
| CL-26 | replace (673-686) with GS + A672C-A694C | remove flexible region, DS (S1-S2) |
| CL-48 | A1080C/I1132C | DS |
| CL-58 | P862E | salt bridge (inter-S1/S2) |
| CL-59 | T859K | salt bridge (inter-S1/S2) |
| CL-60 | T547C/N978C | DS (inter-S1/S2) |
| CL-61 | T961C/S758C | DS (inter-prot) |
| CL-62 | T961C/Q762C | DS (inter-prot) |
| CL-63 | D1118F | Charge removal, pi-pi stacking |
| CL-64 | S659C-S698C | DS (inter-S1/S2) |
| CL-65 | delHR2 | Remove flexible HR2 (1161-1208) |
| CL-66 | delStalk | Remove flexible stalk region (1142-1208) |

TABLE 1-continued

| | Spike protein substitutions and mutations | |
| --- | --- | --- |
| Designation | Mutations (relative to SEQ ID NO: 4) | Strategy |
| DW-1 | R1039F | Charge removal, pi-pi stacking |
| JM-1 | V722C, A930C | Disulfide |
| JM-3 | A903C, Q913C | Disulfide |
| JM-6 | S974C, D979C | Disulfide |
| JM-11 | P728C, V951C | Disulfide |
| JM-14 | V736C, L858C | Disulfide |
| JM-15 | S884C, A893C | Disulfide |
| JM-18 | P807C, S875C | Disulfide |
| JM-19 | T791C, A879C | Disulfide |
| JM-25 | G799C, A924C | Disulfide |
| CL-49 | V826L | Cav |
| CL-50 | A899F | Cav (inter-prot) |
| CL-51 | F817P | Proline |
| CL-52 | L865P/Q779M | Proline/Cav |
| CL-35 | T866P | Proline |
| CL-36 | A892P | Proline, Cav |
| CL-37 | A899P | Proline, Cav |
| CL-38 | T912P | Proline, Cav |
| JG-1 | A570C/V963C | Disulfide |
| CL-27 | T874C, S1055C | DS |
| CL-28 | L894F | Cav (inter-prot) |
| CL-29 | A713S | H bond |
| CL-30 | V729C, A1022C | DS |
| CL-31 | L828K | salt bridge |
| CL-32 | L828R | salt bridge |
| CL-33 | H1058F | Cav |
| CL-34 | H1058Y | Cav, maybe H bond |
| JM-2 | L822C, A1056C | Disulfide |
| JM-4 | Q965C, S1003C | Disulfide |
| JM-5 | A972C, Q992C | Disulfide |
| JM-7 | I980C, Q992C | Disulfide |
| JM-8 | A1078C, V1133C | Disulfide |
| JM-9 | H1088C, T1120C | Disulfide |
| JM-10 | I870C, S1055C | Disulfide |
| JM-12 | T1117C, D1139C | Disulfide |
| JM-13 | T1116C, Y1138C | Disulfide |
| JM-16 | I896C, Q901C | Disulfide |
| JM-17 | G885C, Q901C | Disulfide |
| JM-20 | F1103C, P1112C | Disulfide |
| JM-21 | G889C, L1034C | Disulfide |
| JM-22 | E819C, S1055C | Disulfide |
| JM-23 | A972C, I980C | Disulfide |
| JM-24 | I1081C, N1135C | Disulfide |
| JM-26 | E819C, Q1054C | Disulfide |
| JM-27 | Q957E | salt bridge (inter-prot) |
| CL-44 | V1040Y | Cav |
| CL-45 | H1088Y | Cav |
| CL-46 | V1104I | Cav |
| CL-47 | I1130Y | H bond (inter-pro) |
| JM-28 | R1000Y | Cavity-filling plus H-bond to HR1 |
| JM-29 | R1000W | Cavity-filling |
| JM-30 | A944F | Cavity-filling |
| JM-31 | A944F, T724I | Cavity-filling |
| JM-32 | A944Y | Cavity-filling |
| JM-33 | S730L | Cavity-filling |
| JM-34 | S730R | Salt bridge |
| JM-35 | G769E | Salt bridge |
| CL-53 | A893P | Proline |
| CL-54 | Q895P | Proline |
| CL-55 | K921P | Proline |
| CL-56 | L922P | Proline |
| CL-57 | N978P | Proline |
| CL-39 | A942P | Proline |
| CL-40 | G946P | Proline |
| CL-41 | S975P | Proline |
| CL-42 | A890V | Cav |
| CL-43 | S1003V | Cav |
| NW-1 | R983P | proline |
| NW-2 | L984P | proline |

TABLE 1-continued

| Spike protein substitutions and mutations | | |
|---|---|---|
| Designation | Mutations (relative to SEQ ID NO: 4) | Strategy |
| NW-3 | D985P | proline |
| NW-4 | 986P | proline |
| NW-5 | 987P | proline |
| delta Strep | Remove one Strep tag | |
| delta TwinStrep | Remove both Strep tags | |
| JM-36 | T1027I | Cav |
| delta RBD | replace 333-525 with GGSG | remove RBD |
| delta MPER | end at 1161 | delete C-terminal |
| NW-6 | 984P, 985P | proline |
| NW-7 | 984P, 985G, 986P | proline/glycine |
| NW-8 | 984P, 985G, 986G | proline/glycine |
| NW-9 | 984G, 985P, 986G | proline/glycine |
| NW-10 | 984G, 985P, 986P | proline/glycine |
| NW-11 | 984G, 985G, 986P | proline/glycine |
| NW-12 | 984P, 985P, 986G | proline/glycine |

20

TABLE 2

| SARS-COV-2 Variant Classification and Definitions | |
|---|---|
| Variant Name (Pango lineage) | Spike Protein Substitutions (see SEQ ID NO: 4) |
| B.1.525 | Q52R, A67V, V70I, Y144V, E484K, D614G, Q677H, F888L |
| B.1.526 | L5F, T95I, D253G, S477N, E484K, D614G, A701V |
| B.1.617.1 | T95I, E154K, L452R, E484Q, D614G, P681R |
| B.1.617.2 | T19R, L452R, T478K, D614G, P681R, D950N |
| P.2 | E484K, D614G, V1176F |
| B.1.1.7 | H69del, V70del, Y144del, N501Y, A570D, D614G, P681H, T716I, S982A, D1118H |
| B.1.351 | D80A, D215G, L242del, A243del, L244del, K417N, E484K, N501Y, D614G, A701V |
| B.1.427 | S13I, W152C, W258L, L452R, D614G |
| B.1.429 | S13I, P26S, W152C, L452R, D614G |
| P.1 | L18F, T20N, P26S, D138Y, R190S, K417T, E484K, N501Y, D614G, H655Y, T1027I, V1176F |
| B.1.1.529 | A67V, H69del, V70del, T95I, G142D, V143del, Y144del, Y145del, N211del, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F |

II. Definitions

It is to be understood that both the foregoing general description and the following detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety.

As used herein, the singular forms "a", "an" and "the" include plural references unless the context clearly dictates otherwise. As used herein in the specification, "a" or "an" may mean one or more. As used herein in the claim(s), when used in conjunction with the word "comprising," the words "a" or "an" may mean one or more than one.

The term "about" as used herein when referring to a measurable value such as an amount, a temporal duration, and the like, is meant to encompass variations of up to ±10% from the specified value. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the disclosed subject matter. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding protein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies as described further below. The antigen binding proteins, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the term also encompasses peptibodies.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology, Ch. 7 (Paul, W., ed., 2nd ed. Raven Press, N.Y. (1989)) (incorporated by reference in its entirety for all purposes). The variable regions of each light/heavy chain pair typically form the antigen binding site.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), Chothia & Lesk, J. Mol. Biol., 196:901-917 (1987) or Chothia et al., Nature, 342: 878-883 (1989).

In certain embodiments, an antibody heavy chain binds to an antigen in the absence of an antibody light chain. In certain embodiments, an antibody light chain binds to an antigen in the absence of an antibody heavy chain. In certain embodiments, an antibody binding region binds to an antigen in the absence of an antibody light chain. In certain embodiments, an antibody binding region binds to an antigen in the absence of an antibody heavy chain. In certain embodiments, an individual variable region specifically binds to an antigen in the absence of other variable regions.

In certain embodiments, definitive delineation of a CDR and identification of residues comprising the binding site of an antibody is accomplished by solving the structure of the antibody and/or solving the structure of the antibody-ligand complex. In certain embodiments, that can be accomplished by any of a variety of techniques known to those skilled in the art, such as X-ray crystallography. In certain embodiments, various methods of analysis can be employed to identify or approximate the CDR regions. Examples of such methods include, but are not limited to, the Kabat definition, the Chothia definition, the AbM definition and the contact definition.

The Kabat definition is a standard for numbering the residues in an antibody and is typically used to identify CDR regions. See, e.g., Johnson & Wu, Nucleic Acids Res., 28: 214-8 (2000). The Chothia definition is similar to the Kabat definition, but the Chothia definition takes into account positions of certain structural loop regions. See, e.g., Chothia et al., J. Mol. Biol., 196: 901-17 (1986); Chothia et al., Nature, 342: 877-83 (1989). The AbM definition uses an integrated suite of computer programs produced by Oxford Molecular Group that model antibody structure. See, e.g., Martin et al., Proc Natl Acad Sci (USA), 86:9268-9272 (1989); "AbM™, A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., "Ab Initio Protein Structure Prediction Using a Combined Hierarchical Approach," in PROTEINS, Structure, Function and Genetics Suppl., 3:194-198 (1999). The contact definition is based on an analysis of the available complex crystal structures. See, e.g., MacCallum et al., J. Mol. Biol., 5:732-45 (1996).

By convention, the CDR regions in the heavy chain are typically referred to as H1, H2, and H3 and are numbered sequentially in the direction from the amino terminus to the carboxy terminus. The CDR regions in the light chain are typically referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

A bispecific or bifunctional antibody typically is an artificial hybrid antibody having two different heavy/light chain pairs and two different binding sites. Bispecific antibodies can be produced by a variety of methods including, but not limited to, fusion of hybridomas or linking of Fab' fragments. See, e.g., Songsivilai et al., Clin. Exp. Immunol., 79: 315-321 (1990); Kostelny et al., J. Immunol., 148:1547-1553 (1992).

The term "antigen" refers to a substance capable of inducing adaptive immune responses. Specifically, an antigen is a substance which serves as a target for the receptors of an adaptive immune response. Typically, an antigen is a molecule that binds to antigen-specific receptors but cannot induce an immune response in the body by itself. Antigens are usually proteins and polysaccharides, less frequently also lipids. As used herein, antigens also include immunogens and haptens.

An "Fc" region comprises two heavy chain fragments comprising the CH1 and CH2 domains of an antibody. The two heavy chain fragments are held together by two or more disulfide bonds and by hydrophobic interactions of the CH3 domains.

The "Fv region" comprises the variable regions from both the heavy and light chains but lacks the constant regions.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope. For example, the Coronavirus S protein specific antibodies of the present invention are specific to Coronavirus S protein. In some embodiments, the antibody that binds to Coronavirus S protein has a dissociation constant (Kd) of $\leq$100 nM, $\leq$10 nM, $\leq$1 nM, $\leq$0.1 nM, $\leq$0.01 nM, or $\leq$0.001 nM (e.g., $10^{-8}$ M or less, e.g., from $10^{-8}$ M to $10^{-13}$ M, e.g., from $10^{-9}$ M to $10^{-13}$ M).

The term "compete" when used in the context of antigen binding proteins (e.g., antibody or antigen-binding fragment thereof) that compete for the same epitope means competition between antigen binding proteins as determined by an assay in which the antigen binding protein (e.g., antibody or antigen-binding fragment thereof) being tested prevents or inhibits (e.g., reduces) specific binding of a reference antigen binding protein (e.g., a ligand, or a reference antibody) to a common antigen (e.g., Coronavirus S protein or a fragment thereof). Numerous types of competitive binding assays can be used to determine if one antigen binding protein competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Additional details regarding methods for determining competitive binding are provided in the examples herein. Usually, when a competing antigen binding protein is present in excess, it will inhibit (e.g., reduce) specific binding of a reference antigen binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

The term "epitope" as used herein refers to the specific group of atoms or amino acids on an antigen to which an antibody binds. The epitope can be either linear epitope or a conformational epitope. A linear epitope is formed by a continuous sequence of amino acids from the antigen and interacts with an antibody based on their primary structure. A conformational epitope, on the other hand, is composed of discontinuous sections of the antigen's amino acid sequence and interacts with the antibody based on the 3D structure of the antigen. In general, an epitope is approximately five or six amino acid in length. Two antibodies may bind the same epitope within an antigen if they exhibit competitive binding for the antigen.

The term "host cell" means a cell that has been transformed, or is capable of being transformed, with a nucleic acid sequence and thereby expresses a gene of interest. The term includes the progeny of the parent cell, whether or not the progeny is identical in morphology or in genetic makeup to the original parent cell, so long as the gene of interest is present.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3×the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Examples of parameters that can be employed in determining percent identity for polypeptides or nucleotide sequences using the GAP program can be found in Needleman et al., 1970, J. Mol. Biol. 48:443-453.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 or other number of contiguous amino acids of the target polypeptide.

The term "link" as used herein refers to the association via intramolecular interaction, e.g., covalent bonds, metallic bonds, and/or ionic bonding, or inter-molecular interaction, e.g., hydrogen bond or noncovalent bonds.

The term "operably linked" refers to an arrangement of elements wherein the components so described are configured so as to perform their usual function. Thus, a given signal peptide that is operably linked to a polypeptide directs the secretion of the polypeptide from a cell. In the case of a promoter, a promoter that is operably linked to a coding sequence will direct the expression of the coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The term "polynucleotide" or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The terms "polypeptide" or "protein" means a macromolecule having the amino acid sequence of a native protein, that is, a protein produced by a naturally-occurring and non-recombinant cell; or it is produced by a genetically-engineered or recombinant cell, and comprise molecules having the amino acid sequence of the native protein, or molecules having deletions from, additions to, and/or substitutions of one or more amino acids of the native sequence. The term also includes amino acid polymers in which one or more amino acids are chemical analogs of a corresponding naturally occurring amino acid and polymers. The terms "polypeptide" and "protein" specifically encompass Coronavirus S protein binding proteins, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. In certain embodiments, fragments are about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a CORONAVIRUS S PROTEIN-binding antibody, useful fragments include but are not limited to a CDR region, a variable domain of a heavy and/or light chain, a portion of an antibody chain or just its variable region including two CDRs, and the like.

The pharmaceutically acceptable carriers useful in this invention are conventional. Remington's Pharmaceutical Sciences, by E. W. Martin, Mack Publishing Co., Easton, Pa., 15th Edition (1975), describes compositions and formulations suitable for pharmaceutical delivery of the fusion proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

The term "therapeutically effective amount" or "effective dosage" as used herein refers to the dosage or concentration of a drug effective to treat a disease or condition. For example, with regard to the use of the monoclonal antibodies or antigen-binding fragments thereof disclosed herein to treat viral infection.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

As used herein, a "vector" refers to a nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

III. Pharmaceutical Formulations

The present disclosure provides pharmaceutical compositions comprising an engineered, stabilized beta-coronavirus S2 domain-only protein, a nucleic acid molecule encoding an engineered, stabilized beta-coronavirus S2 domain-only protein, and viral vector comprising an engineered, stabilized beta-coronavirus S2 domain-only protein and/or encoding the engineered, stabilized beta-coronavirus S2 domain-only protein in its genomic material. Such compositions can be used for stimulating an immune response, such as part of a vaccine formulation.

In the case that a nucleic acid molecule encoding an engineered, stabilized beta-coronavirus S2 domain-only protein is used in a pharmaceutical composition, the nucleic acid molecule may comprise or consist of deoxyribonucleotides and/or ribonucleotides, or analogs thereof, covalently linked together. A nucleic acid molecule as described herein generally contains phosphodiester bonds, although in some cases, nucleic acid analogs are included that may have at least one different linkage, e.g., phosphoramidate, phosphorothioate, phosphorodithioate, or O-methylphophoroamidite linkages, and peptide nucleic acid backbones and linkages. Mixtures of naturally occurring polynucleotides and analogs can be made; alternatively, mixtures of different polynucleotide analogs, and mixtures of naturally occurring polynucleotides and analogs may be made. A nucleic acid molecule may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, the term polynucleotide encompasses both the double-stranded form and each of two complementary single-stranded forms known or predicted to make up the double-stranded form. A nucleic acid molecule is composed of a specific sequence of four nucleotide bases: adenine (A), cytosine (C), guanine (G), thymine (T), and uracil (U) for thymine when the polynucleotide is RNA. Thus, the term "nucleic acid sequence" is the alphabetical representation of a nucleic acid molecule. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues.

In some embodiments, the nucleic acids of the present disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In some embodiments, modified sugar moieties are substituted sugar moieties. In some embodiments, modified sugar moieties are sugar surrogates. Such sugar surrogates may comprise one or more substitutions corresponding to those of substituted sugar moieties.

In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, $CF_3$, $OCF_3$, O, S, or $N(R_m)$-alkyl; O, S, or $N(R_m)$-alkenyl; O, S or $N(R_m)$-alkynyl; O-alkylenyl-O-alkyl, alkynyl, alkaryl, aralkyl, O-alkaryl, O-aralkyl, $O(CH_2)_2SCH_3$, $O(CH_2)_2$—O—$N(R_m)(R_n)$ or O—$CH_2$—C($=$O)—$N(R_m)$ $(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In some embodiments, a 2'-substituted nucleoside comprises a 2'-substituent group selected from F, $NH_2$, $N_3$, $OCF_3$, O—$CH_3$, $O(CH_2)_3NH_2$, $CH_2$—CH$=$$CH_2$, O—$CH_2$—CH$=$$CH_2$, $OCH_2CH_2OCH_3$, $O(CH_2)_2SCH_3$, O—$(CH_2)_2$—O—$N(R_m)(R_n)$, $O(CH_2)_2O(CH_2)_2N(CH_3)_2$, and N-substituted acetamide (O—$CH_2$—C($=$O)—$N(R_m)$ $(R_n)$ where each $R_m$ and $R_n$ is, independently, H, an amino protecting group or substituted or unsubstituted $C_1$-$C_{10}$ alkyl.

In some embodiments, a 2'-substituted nucleoside comprises a sugar moiety comprising a 2'-substituent group selected from F, $OCF_3$, O—$CH_3$, $OCH_2CH_2OCH_3$, $O(CH_2)_2SCH_3$, $O(CH_2)_2$—O—$N(CH_3)_2$, —$O(CH_2)_2O$ $(CH_2)_2N(CH_3)_2$, and O—$CH_2$—C($=$O)—N(H)$CH_3$.

In some embodiments, a 2'-substituted nucleoside comprises a sugar moiety comprising a 2'-substituent group selected from F, O—$CH_3$, and $OCH_2CH_2OCH_3$.

In some embodiments, nucleosides of the present disclosure comprise one or more unmodified nucleobases. In certain embodiments, nucleosides of the present disclosure comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-amino-propyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2':4,5]pyrrolo[2,3- d]pyrimidin-2-one). Modified nucleobases may also include those in which the purine or pyrimidine base is replaced with other heterocycles, for example 7-deaza-adenine, 7-deaza-aguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., 1991; and those disclosed by Sanghvi, Y. S., 1993.

Representative United States patents that teach the preparation of certain of the above noted modified nucleobases as well as other modified nucleobases include without limitation, U.S. Pat. Nos. 3,687,808; 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121; 5,596,091; 5,614,617; 5,645,985; 5,681, 941; 5,750,692; 5,763,588; 5,830,653 and 6,005,096, each of which is herein incorporated by reference in its entirety.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., 1989), cholic acid (Manoharan et al., 1994), a thioether, e.g., hexyl-5-tritylthiol (Manoharan et al., 1992; Manoharan et al., 1993), a thio-cholesterol (Oberhauser et al., 1992), an aliphatic chain, e.g., dodecandiol or undecyl residues (Saison-Behmoaras et al., 1991; Kabanov et al., 1990; Svinarchuk et al., 1993), a phospholipid, e.g., di-hexadecyl-rac-glycerol or triethylammonium 1,2-di-O-hexadecyl-rac-glycero-3-H-phosphonate (Manoharan et al., 1995; Shea et al., 1990), a polyamine or a polyethylene glycol chain (Manoharan et al., 1995), or adamantane acetic acid (Manoharan et al., 1995), a palmityl moiety (Mishra et al., 1995), or an octadecylamine or hexylamino-carbonyl-oxycholesterol moiety (Crooke et al., 1996). The some aspects, a nucleic acid molecule encoding an engineered Coronavirus S protein is a modified RNA, such as, for example, a modified mRNA. Modified (m)RNA contemplates certain chemical modifications that confer increased stability and low immunogenicity to mRNAs, thereby facilitating expression of therapeutically important proteins. For instance, N1-methyl-pseudouridine (N1m$\Psi$) outperforms several other nucleoside modifications and their combinations in terms of translation capacity. In some embodiments, the (m)RNA molecules used herein may have the uracils replaced with psuedouracils such as 1-methyl-3'-pseudouridylyl bases. In some embodiments, some of the uracils are replaced, but in other embodiments, all of the uracils have been replaced. The (m)RNA may comprise a 5' cap, a 5' UTR element, an optionally codon optimized open reading frame, a 3' UTR element, and a poly(A) sequence and/or a polyadenylation signal.

The nucleic acid molecule, whether native or modified, may be delivered as a naked nucleic acid molecule or in a delivery vehicle, such as a lipid nanoparticle. A lipid nanoparticle may comprise one or more nucleic acids present in a weight ratio to the lipid nanoparticles from about 5:1 to about 1:100. In some embodiments, the weight ratio of nucleic acid to lipid nanoparticles is from about 5:1, 2.5:1, 1:1, 1:5, 1:10, 1:15, 1:20, 1:25, 1:30, 1:35, 1:40, 1:45, 1:50, 1:60, 1:70, 1:80, 1:90, or 1:100, or any value derivable therein.

In some embodiments, the lipid nanoparticles used herein may contain one, two, three, four, five, six, seven, eight, nine, or ten lipids. These lipids may include triglycerides, phospholipids, steroids or sterols, a PEGylated lipids, or a group with a ionizable group such as an alkyl amine and one or more hydrophobic groups such as C6 or greater alkyl groups.

In some aspects of the present disclosure, the lipid nanoparticles are mixed with one or more steroid or a steroid derivative. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms.

In some aspects of the present disclosure, the lipid nanoparticles are mixed with one or more PEGylated lipids (or PEG lipid). In some embodiments, the present disclosure comprises using any lipid to which a PEG group has been attached. In some embodiments, the PEG lipid is a diglyceride which also comprises a PEG chain attached to the glycerol group. In other embodiments, the PEG lipid is a compound which contains one or more C6-C24 long chain alkyl or alkenyl group or a C6-C24 fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present disclosure are taught by U.S. Pat. No. 5,820,873, WO 2010/141069, or U.S. Pat. No. 8,450,298, which is incorporated herein by reference.

In some aspects of the present disclosure, the lipid nanoparticles are mixed with one or more phospholipids. In some embodiments, any lipid which also comprises a phosphate group. In some embodiments, the phospholipid is a structure which contains one or two long chain C6-C24 alkyl or alkenyl groups, a glycerol or a sphingosine, one or two phosphate groups, and, optionally, a small organic molecule. In some embodiments, the small organic molecule is an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some aspects of the present disclosure, lipid nanoparticle containing compounds containing lipophilic and cationic components, wherein the cationic component is ionizable, are provided. In some embodiments, the cationic ionizable lipids contain one or more groups which is protonated at physiological pH but may deprotonated and has no charge at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some aspects of the present disclosure, composition containing compounds containing lipophilic and cationic components, wherein the cationic component is ionizable, are provided. In some embodiments, ionizable cationic lipids refer to lipid and lipid-like molecules with nitrogen atoms that can acquire charge (pKa). These lipids may be known in the literature as cationic lipids. These molecules with amino groups typically have between 2 and 6 hydrophobic chains, often alkyl or alkenyl such as C6-C24 alkyl or alkenyl groups, but may have at least 1 or more that 6 tails.

In some embodiments, the amount of the lipid nanoparticle with the nucleic acid molecule encapsulated in the pharmaceutical composition is from about 0.1% w/w to about 50% w/w, from about 0.25% w/w to about 25% w/w, from about 0.5% w/w to about 20% w/w, from about 1% w/w to about 15% w/w, from about 2% w/w to about 10% w/w, from about 2% w/w to about 5% w/w, or from about 6% w/w to about 10% w/w. In some embodiments, the amount of the lipid nanoparticle with the nucleic acid molecule encapsulated in the pharmaceutical composition is from about 0.1% w/w, 0.25% w/w, 0.5% w/w, 1% w/w, 2.5% w/w, 5% w/w, 7.5% w/w, 10% w/w, 15% w/w, 20% w/w, 25% w/w, 30% w/w, 35% w/w, 40% w/w, 45% w/w, 50% w/w, 55% w/w, 60% w/w, 65% w/w, 70% w/w, 75% w/w, 80% w/w, 85% w/w, 90% w/w, to about 95% w/w, or any range derivable therein.

In some aspects, the present disclosure comprises one or more sugars formulated into pharmaceutical compositions. In some embodiments, the sugars used herein are saccharides. These saccharides may be used to act as a lyoprotectant that protects the pharmaceutical composition from destabilization during the drying process. These water-soluble excipients include carbohydrates or saccharides such as disaccharides such as sucrose, trehalose, or lactose, a trisaccharide such as fructose, glucose, galactose comprising raffinose, polysaccharides such as starches or cellulose, or a sugar alcohol such as xylitol, sorbitol, or mannitol. In some embodiments, these excipients are solid at room temperature. Some non-limiting examples of sugar alcohols include erythritol, threitol, arabitol, xylitol, ribitol, mannitol, sorbitol, galactitol, fucitol, iditol, inositol, volemitol, isomalt, maltitol, lactitol, maltotritol, maltotetraitol, or a polyglycitol.

In some embodiments, the amount of the sugar in the pharmaceutical composition is from about 25% w/w to about 98% w/w, 40% w/w to about 95% w/w, 50% w/w to about 90% w/w, 50% w/w to about 70% w/w, or from about 80% w/w to about 90% w/w. In some embodiments, the amount of the sugar in the pharmaceutical composition is from about 10% w/w, 15% w/w, 20% w/w, 25% w/w, 30% w/w, 35% w/w, 40% w/w, 45% w/w, 50% w/w, 52.5% w/w, 55% w/w, 57.5% w/w, 60% w/w, 62.5% w/w, 65% w/w, 67.5% w/w, 70% w/w, 75% w/w, 80% w/w, 82.5% w/w, 85% w/w, 87.5% w/w, 90% w/w, to about 95% w/w, or any range derivable therein.

In some embodiments, the pharmaceutically acceptable polymer is a copolymer. The pharmaceutically acceptable polymer may further comprise one, two, three, four, five, or six subunits of discrete different types of polymer subunits. These polymer subunits may include polyoxypropylene, polyoxyethylene, or a similar subunit. In particular, the pharmaceutically acceptable polymer may comprise at least one hydrophobic subunit and at least one hydrophilic subunit. In particular, the copolymer may have hydrophilic subunits on each side of a hydrophobic unit. The copolymer may have a hydrophilic subunit that is polyoxyethylene and a hydrophobic subunit that is polyoxypropylene.

In some embodiments, expression cassettes are employed to express an engineered, stabilized beta-coronavirus S2 domain-only protein, either for subsequent purification and delivery to a cell/subject, or for use directly in a viral-based delivery approach. Provided herein are expression vectors which contain one or more nucleic acids encoding an engineered, stabilized beta-coronavirus S2 domain-only protein.

Expression requires that appropriate signals be provided in the vectors and include various regulatory elements such as enhancers/promoters from both viral and mammalian sources that drive expression of the an engineered, stabilized beta-coronavirus S2 domain-only protein in cells. Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

The promoter and/or enhancer may be, for example, immunoglobulin light chain, immunoglobulin heavy chain, T-cell receptor, HLA DQ a and/or DQ β, β-interferon, interleukin-2, interleukin-2 receptor, MHC class II 5, MHC class II HLA-Dra, β-Actin, muscle creatine kinase (MCK), prealbumin (transthyretin), elastase I, metallothionein (MTII), collagenase, albumin, α-fetoprotein, t-globin, β-globin, c-fos, c-HA-ras, insulin, neural cell adhesion molecule (NCAM), $\alpha_1$-antitrypain, H2B (TH2B) histone, mouse and/or type I collagen, glucose-regulated proteins (GRP94 and GRP78), rat growth hormone, human serum amyloid A (SAA), troponin I (TN I), platelet-derived growth factor (PDGF), SV40, polyoma, retroviruses, papilloma virus, hepatitis B virus, human immunodeficiency virus, cytomegalovirus (CMV), and gibbon ape leukemia virus.

Where a cDNA insert is employed, one will typically desire to include a polyadenylation signal to effect proper polyadenylation of the gene transcript. Any polyadenylation sequence may be employed such as human growth hormone and SV40 polyadenylation signals. Also contemplated as an element of the expression cassette is a terminator. These elements can serve to enhance message levels and to minimize read through from the cassette into other sequences.

There are a number of ways in which expression vectors may be introduced into cells. In certain embodiments, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells. These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals.

One method for in vivo delivery involves the use of an adenovirus expression vector. "Adenovirus expression vector" is meant to include those constructs containing adenovirus sequences sufficient to (a) support packaging of the construct and (b) to express engineered, stabilized beta-coronavirus S2 domain-only protein that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off. The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNAs issued from this promoter possess a 5'-tripartite leader (TPL) sequence which makes them preferred mRNAs for translation. In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins. Since the E3 region is dispensable from the adenovirus genome, the current adenovirus vectors, with the help of 293 cells, carry foreign DNA in either the E1, the D3 or both regions. In nature, adenovirus can package approximately 105% of the wild-type genome, providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

The adenoviruses of the disclosure are replication defective, or at least conditionally replication defective. The adenovirus may be of any of the 42 different known serotypes or subgroups A-F. Adenovirus type 5 of subgroup C is one exemplary starting material that may be used to obtain the conditional replication-defective adenovirus vector for use in the present disclosure.

Other viral vectors may be employed as expression constructs in the present disclosure. Vectors derived from viruses such as vaccinia virus, adeno-associated virus (AAV) and herpesviruses may be employed. They offer several attractive features for various mammalian cells.

In embodiments, particular embodiments, the vector is an AAV vector. AAV is a small virus that infects humans and some other primate species. AAV is not currently known to cause disease. The virus causes a very mild immune response, lending further support to its apparent lack of pathogenicity. In many cases, AAV vectors integrate into the host cell genome, which can be important for certain applications, but can also have unwanted consequences. Gene therapy vectors using AAV can infect both dividing and quiescent cells and persist in an extrachromosomal state without integrating into the genome of the host cell, although in the native virus some integration of virally carried genes into the host genome does occur. These features make AAV a very attractive candidate for creating viral vectors for gene therapy, and for the creation of isogenic human disease models. Recent human clinical trials using AAV for gene therapy in the retina have shown promise. AAV belongs to the genus Dependoparvovirus, which in turn belongs to the family Parvoviridae. The virus is a small (20 nm) replication-defective, nonenveloped virus.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. This feature makes it somewhat more predictable than retroviruses, which present the threat of a random insertion and of mutagenesis, which is sometimes followed by development of a cancer. The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatemer formation in the nucleus after the single-stranded vector DNA is converted by host cell DNA polymerase complexes into double-stranded DNA. AAV-based gene therapy vectors form episomal concatemers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for human gene therapy.

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

The Inverted Terminal Repeat (ITR) sequences comprise 145 bases each. They were named so because of their symmetry, which was shown to be required for efficient multiplication of the AAV genome. The feature of these sequences that gives them this property is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particles.

With regard to gene therapy, ITRs seem to be the only sequences required in cis next to the therapeutic gene: structural (cap) and packaging (rep) proteins can be delivered in trans. With this assumption many methods were established for efficient production of recombinant AAV (rAAV) vectors containing a reporter or therapeutic gene. However, it was also published that the ITRs are not the only elements required in cis for the effective replication and encapsidation. A few research groups have identified a sequence designated cis-acting Rep-dependent element (CARE) inside the coding sequence of the rep gene. CARE was shown to augment the replication and encapsidation when present in cis.

In some aspects, the present disclosure provides pharmaceutical compositions that contain one or more salts. The salts may be an inorganic potassium or sodium salt such as potassium chloride, sodium chloride, potassium phosphate dibasic, potassium phosphate monobasic, sodium phosphate dibasic, or sodium phosphate monobasic. The pharmaceutical composition may comprise one or more phosphate salts such to generate a phosphate buffer solution. The phosphate buffer solution may be comprise each of the phosphates to buffer a solution to a pH from about 6.8, 6.9, 7.0, 7.1, 7.2, 7.3, 7.4, 7.5, 7.6, 7.7, 7.8, 7.9, or 8.0, or any range derivable therein.

In some aspects, the present disclosure comprises one or more excipients formulated into pharmaceutical compositions. An "excipient" refers to pharmaceutically acceptable carriers that are relatively inert substances used to facilitate administration or delivery of an API into a subject or used to facilitate processing of an API into drug formulations that can be used pharmaceutically for delivery to the site of action in a subject. Furthermore, these compounds may be used as diluents in order to obtain a dosage that can be readily measured or administered to a patient. Non-limiting examples of excipients include polymers, stabilizing agents, surfactants, surface modifiers, solubility enhancers, buffers, encapsulating agents, antioxidants, preservatives, nonionic wetting or clarifying agents, viscosity increasing agents, and absorption-enhancing agents.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and can preferably include an adjuvant. Water is a particular carrier when the pharmaceutical composition is administered by injections, such an intramuscular injection. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Engineered proteins or nucleic acids encoding engineered proteins of the present disclosure, as described herein, can be formulated for parenteral administration, e.g., formulated for injection via the intradermal, intravenous, intramuscular, subcutaneous, intra-tumoral or even intraperitoneal routes. The formulation could alternatively be administered by a topical route directly to the mucosa, for example by nasal drops, inhalation, or by nebulizer. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Dosage can be by a single dose schedule or a multiple dose schedule. Multiple doses may be used in a primary immunization schedule and/or in a booster immunization schedule. In a multiple dose schedule the various doses may be given by the same or different routes. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein may be used to treat both children and adults. Thus a human subject may be less than 1 year old, 1-5 years old, 5-16 years old, 16-55 years old, 55-65 years old, or at least 65 years old.

Preferred routes of administration include, but are not limited to, intramuscular, intraperitoneal, intradermal, subcutaneous, intravenous, intraarterial, and intraoccular injection. Particularly preferred routes of administration include intramuscular, intradermal and subcutaneous injection.

IV. Immunodetection Methods

In still further embodiments, the present disclosure concerns immunodetection methods for binding, purifying, removing, quantifying and otherwise generally detecting Coronavirus S protein. While such methods can be applied in a traditional sense, another use will be in quality control and monitoring of vaccine stocks, where antibodies according to the present disclosure can be used to assess the amount or integrity (i.e., long term stability) of antigens. Alternatively, the methods may be used to screen various antibodies for appropriate/desired reactivity profiles.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Coronavirus S protein also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Coronavirus S protein, and contacting the sample with a first antibody in accordance with the present disclosure, as the case may be, under conditions effective to allow the formation of immunocomplexes.

These methods include methods for detecting or purifying Coronavirus S protein or Coronavirus S protein from a sample. The antibody will preferably be linked to a solid support, such as in the form of a column matrix, and the sample suspected of containing the Coronavirus S protein will be applied to the immobilized antibody. The unwanted components will be washed from the column, leaving the Coronavirus S protein-expressing cells immunocomplexed to the immobilized antibody, which is then collected by removing the organism or antigen from the column.

The immunobinding methods also include methods for detecting and quantifying the amount of Coronavirus S protein or related components in a sample and the detection and quantification of any immune complexes formed during the binding process. Here, one would obtain a sample suspected of containing Coronavirus S protein and contact the sample with an antibody that binds Coronavirus S protein or components thereof, followed by detecting and quantifying the amount of immune complexes formed under the specific conditions. In terms of antigen detection, the biological sample analyzed may be any sample that is suspected of containing Coronavirus S protein, such as a tissue section or specimen, a homogenized tissue extract, a biological fluid (e.g., a nasal swab), including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Coronavirus S protein. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Coronavirus S protein is added to the wells. After binding and washing to remove non-specifically bound immune complexes, the bound antigen may be detected. Detection may be achieved by the addition of another anti-Coronavirus S protein antibody that is linked to a detectable label. This type of ELISA is a simple "sandwich ELISA." Detection may also be achieved by the addition of a second anti-Coronavirus S protein antibody, followed by the addition of a third antibody that has binding affinity for the second antibody, with the third antibody being linked to a detectable label.

In another exemplary ELISA, the samples suspected of containing the Coronavirus S protein (e.g., potentially infected cells) are immobilized onto the well surface and then contacted with the anti-Coronavirus S protein antibodies of the disclosure. After binding and washing to remove non-specifically bound immune complexes, the bound anti-Coronavirus S protein antibodies are detected. Where the initial anti-Coronavirus S protein antibodies are linked to a detectable label, the immune complexes may be detected directly. Again, the immune complexes may be detected using a second antibody that has binding affinity for the first anti-Coronavirus S protein antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG)

or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Coronavirus S protein, the antibodies may be included in the kit. The immunodetection kits will thus comprise, in suitable container means, a first antibody that binds to an Coronavirus S protein, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of Coronavirus S protein, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Flow Cytometry and FACS

The antibodies of the present disclosure may also be used in flow cytometry or FACS. Flow cytometry is a laser- or impedance-based technology employed in many detection assays, including cell counting, cell sorting, biomarker detection and protein engineering. The technology suspends cells in a stream of fluid and passing them through an electronic detection apparatus, which allows simultaneous multiparametric analysis of the physical and chemical characteristics of up to thousands of particles per second. Flow cytometry is routinely used in the diagnosis disorders, especially blood cancers, but has many other applications in basic research, clinical practice and clinical trials.

Fluorescence-activated cell sorting (FACS) is a specialized type of cytometry. It provides a method for sorting a heterogenous mixture of biological cells into two or more containers, one cell at a time, based on the specific light scattering and fluorescent characteristics of each cell. In general, the technology involves a cell suspension entrained in the center of a narrow, rapidly flowing stream of liquid. The flow is arranged so that there is a large separation between cells relative to their diameter. A vibrating mechanism causes the stream of cells to break into individual droplets. Just before the stream breaks into droplets, the flow passes through a fluorescence measuring station where the fluorescence of each cell is measured. An electrical charging ring is placed just at the point where the stream breaks into droplets. A charge is placed on the ring based immediately prior to fluorescence intensity being measured, and the opposite charge is trapped on the droplet as it breaks form the stream. The charged droplets then fall through an electrostatic deflection system that diverts droplets into containers based upon their charge.

In certain embodiments, to be used in flow cytometry or FACS, the antibodies of the present disclosure are labeled with fluorophores and then allowed to bind to the cells of interest, which are analyzed in a flow cytometer or sorted by a FACS machine.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

Design scheme for MERS stem stabilized spike variants. The base construct used for the S2 subunit of MERS-CoV S-2P variant contained residues 762-1291 of MERS-CoV S (GenBank ID: AFY13307) with proline substituted at residues 1060 and 1061, the foldon trimerization motif of T4 fibritin, an HRV3C protease recognition site, an octa-histidine tag, and a tandem Twin-Strep-tag, cloned into the mammalian expression plasmid pαH. All mutations in subsequent designs were introduced into this base construct. The initial design was conducted via the PROSS server (Goldenzweig et al., 2016), and a total of 11 substitutions were picked (yielding the 'mut11' construct) from 53 computational designs based on the biochemical property of the residues and steric effect on the prefusion-stabilized MERS S-2P structure (PDB ID: 5W91). Using structure-based design, additional substitutions that were aimed at favoring the stability of the prefusion structure were introduced into the mut11 backbone. Pairs of core-facing residues less than 5 Å apart were replaced with aromatic sidechains or pairs of aromatic and positively charged sidechains to favor pi-pi or pi-cation interactions, respectively. Alternatively, residues were replaced with extended or bulkier hydrophobic sidechains in efforts to fill pre-existing internal cavities. Disulfide bonds were designed to increase overall stability or prevent formation of the postfusion conformation. The charged or polar substitutions were aimed to establish hydrogen bonds or salt bridges with the native residues that were predicted to be within 4.0 Å. To examine the effect of the substitutions in the mut11 backbone, the mutations were individually or combinatorially reverted back to the wildtype sequence. Three designs, each containing 5-7 of the beneficial substitutions from the PROSS server (mut5, mut6 and mut7) were chosen to serve as backgrounds for subsequent rounds of design. These were then combined with individual substitutions or combinations of substitutions from the structure-based designs that were shown to be beneficial, for subsequent assessment of improved monodispersity and thermostability. Substitutions predicted to potentially interfere with one another or clash with native residues were avoided.

Protein expression and purification for MERS SS variants. Plasmids encoding MERS SS variants were transiently transfected into FreeStyle293F cells (Thermo Fisher) using polyethyleneimine, with 5 µM kifunensine being added 3 h post-transfection. Cultures were grown for 6 days, and culture supernatant was separated via centrifugation and passage through a 0.22 µm filter. Protein was purified from supernatants using StrepTactin resin (IBA). MERS SS variants were further purified by size-exclusion chromatography (SEC) using a Superose 6 10/300 column (GE Healthcare) in a buffer composed of 2 mM Tris pH 8.0, 200 mM NaCl and 0.02% NaN3. For initial purification and characterization, single-substitution and combinatorial variants were purified from 40 mL cultures. The SS.V1 and SS.V2 variants were further tested in large-scale expression and purification from 1 L cultures. The protein purity, monodispersity and expression level were determined by SDS-PAGE and SEC.

Differential scanning fluorimetry. MERS SS variants were prepared at a concentration of 1.5 µM with a final concentration 5×SYPRO Orange Protein Gel Stain (ThermoFisher) in a white, opaque 96-wellplate. Continuous fluorescence measurements ($\lambda$ex=465 nm, $\lambda$em=580 nm) were performed using a Roche LightCycler 480 II, with a temperature ramp rate of 4.4° C./minute, and a temperature range of 25° C. to 95° C. Data were plotted as the derivative of the melting curve.

Mouse experiments. Mouse experiments were carried out in compliance with all pertinent US National Institutes of Health regulations and approval from the Animal Care and Use Committee (ACUC) of the Vaccine Research Center, University of North Carolina at Chapel Hill, or Abcellera Biologics. For immunogenicity studies, female BALB/cJ mice aged 6- to 8-weeks (Jackson Laboratory) were used. Per the experimental design schema outlined in FIG. 3A, mice were inoculated intramuscularly with protein immunogens adjuvanted with SAS as previously described (Pallesen et al., 2017) and bled for serological assays. For challenge studies to evaluate MERS-CoV vaccines, 16- to 20-week-old male and female 288/330+/+ mice (Cockrell et al., 2016) were immunized, bled, and challenged, as detailed in FIG. 4A. Mice were challenged with $5\times10^5$ PFU of a mouse-adapted MERS-CoV EMC derivative, m35c4 (Douglas et al., 2018). On days 3 and 5 post-challenge, lungs were collected from selected mice to assess viral titers and hemorrhage, using previously published methods. For S-reactive monoclonal antibody isolation, female C57BL/6J mice aged 4- to 8-weeks (Jackson Laboratory) were used. Mice were immunized intramuscularly with 10 µg MERS SS.V1+SAS at weeks 0, 3, and 9. At week 13, mice were euthanized and spleens, thymuses, and lymph nodes were harvested for single B cell technology for mAb isolation. Sample size for animal experiments was determined on the basis of criteria set by institutional ACUC. Experiments were neither randomized nor blinded.

Serum IgG measurement. HCoV S-2P-specific IgG in immunized mouse sera were quantified via enzyme-linked immunosorbent assay (ELISA). Briefly, Nunc MaxiSorp 96-well plates (ThermoFisher) were coated with either MERS S2P, SARS S-2P, SARS-CoV-2 S-2P, or HKU1 S-2P at 1 µg/mL in 1×PBS 400 at 4° C. for 16 h. Sera dilutions were prepared in blocking buffer, which consisted of PBS-Tween 20+5% non-fat dairy milk, and diluted serially at 1:100, four-fold, 8×. To eliminate foldon-specific binding, 50 µg/mL of foldon was added to the dilutions and incubated for an hour at room temperature. After standard washes and blocks, goat anti-mouse IgG-horseradish peroxidase (HRP) conjugate (SigmaAldrich) was used as secondary antibody.

Plates were reacted with 3,5,3'5'-tetramethylbenzidine (TMB) (KPL) to detect binding responses. Plates were read at OD450/650 using SpectraMax Paradigm (Molecular Devices). Endpoint titers were calculated as the reciprocal serum dilution that yielded a signal 4×greater than that of the background signal (secondary antibody alone).

Pseudovirus neutralization assay. Neutralization activity was assessed as previously described (Pallesen et al., 2017). Briefly, Huh7.5 cells were seeded at 10,000 cells/well in 96-well black/white Isoplates (PerkinElmer) 24-h prior to infection. Sera were serially diluted (1:40, 4-fold dilutions, 8×) in DMEM (Gibco)+1% penicillin/streptomycin, and mixed with a pseudotyped MERS-CoV England1 lentivirus reporter that was previously titrated to $10^4$ RLU, and incubated for 30 minutes at room temperature. Thr sera+ pseudovirus mixture was then added to Huh7.5 cells in duplicate, and incubated at 37° C. and 5% CO2 for 2 h. Then, 100 µL of DMEM supplemented with 10% FBS, 2 mM glutamine, and 1% penicillin/streptomycin was added to each well, and incubated for 72 h. Cells were then lysed, and luciferase substrate (Promega) was added. Luciferase activity was measured as relative luciferase units (RLU) at 570 nm, using a SpectraMaxL (Molecular Devices). Sigmoidal curves, taking averages of triplicates at each dilution, were generated from RLU readings; 50% neutralization ($ID_{50}$) titers were calculated considering uninfected cells as 100% neutralization and cells transduced with only virus as 0% neutralization, by fitting RLU readings to a log(agonist) vs. normalized-response (variable slope) nonlinear regression model in Prism v8 (GraphPad).

Single-cell screening and recovery. Immunized mice exhibiting elevated serum titers were sacrificed and plasma cells from lymph node, spleen, and bone marrow tissues were isolated using standard protocols. Samples were screened with AbCellera's high-throughput single-cell microfluidic platform using a multiplexed microbead assay on devices containing individual nanoliter-volume reaction chambers (Lecault et al., 2011). The multiplexed assay employed multiple optically-encoded beads, each conjugated to one of the following unique antigens: full-length pre-fusion stabilized spike proteins of MERS-CoV, SARS-CoV, or HKU1-CoV, or the S2 subunit of MERS-CoV spike. Bead-conjugated bovine serum albumin (BSA) His-tag and T4 foldon trimerization domain were used as negative controls. Beads were flowed into microfluidic screening devices and incubated with single antibody-secreting cells, and monoclonal antibody binding to cognate antigens was detected via a fluorescently labeled anti-human IgG secondary antibody. Positive hits were identified using machine vision and recovered using automated robotics-based protocols.

Single-cell sequencing, bioinformatic analysis, and cloning. For recovery of paired heavy and light chain sequences, single-cell polymerase chain reaction (PCR) and next-generation sequencing (MiSeq, Illumina) were performed using automated workstations (Bravo, Agilent) and custom molecular biology protocols. Sequences were analyzed using a custom bioinformatics pipeline to yield paired heavy and light chain sequences for each recovered antibody secreting cell. Each sequence was assigned the closest germline (V(D)J) genes, degree of somatic hypermutation, and potential sequence liabilities.

Expression and purification of IgGs and Fab. Twenty monoclonal antibodies discovered by single B cell technology were selected for characterization based on their binding specifies to HKU1-S, MERS-S and SARS-1-S (monospecific, bi-specific or tri-specific), diversity of heavy and light chain CDR3s, and high frequency rates in the B cell reper-
toire (independently isolated by the probes more than 2
times). The individual VH sequence of selected IgGs was
cloned into a mammalian expression plasmid pVRC8400
containing HRV 3C cleavage site in the hinge, and human
IgG1 Fc domain. VL sequences were also cloned into
pVRC8400 with human CL. Paired VH and VL in a 1:1 ratio
were co-transfected transiently into FreeStyle293F cells as
previously described. The supernatant was harvested six
days post-transfection and IgGs were purified with Protein A
agarose (ThermoFisher). IgGs were eluted with 100 mM
glycine, pH 3 into ¹⁄₁₀th volume 1 M Tris-HCl pH 8.0. IgGs
were then buffer exchanged into PBS pH 7.4. Fab fragments
were generated by digesting the IgGs with HRV 3C protease
at 4° C. Fc was removed by passing digests over a fresh
Protein A agarose, leaving the Fab in the flowthrough, which
was further purified by SEC using a Superdex 200 increase
10/300 column (GE Healthcare) in PBS buffer, pH 7.4.

Spike binding analysis by Biolayer interferometry. The
binding affinity of purified IgGs to HKU1-CoV S, MERS-
CoV S or SARS-CoV S was characterized by BLI using an
Octet RED96e (FortéBio). Briefly, anti-human Fc (AHC)
sensors (FortéBio) with captured IgG were dipped into the
wells containing 100 nM of CoV spikes in a BLI buffer
composed of 10 mM HEPES pH 7.4, 150 mM NaCl, 0.005%
v/v Tween 20 and 1 mg/mL BSA. After 600 s association
step, the dissociation step was carried out in the wells
containing only BLI buffer for 600 s. RSV F-foldon was also
included in the experiments as negative control. The binding
affinity of purified mAb G4 to MERS-CoV S and MERS SS
was also characterized by BLI using similar approach. AHC
sensors with captured mAb G4 were dipped into the wells
containing serial dilutions of MERS-CoV S or MERS SS at
concentration ranging from 100 to 1.56 nM in a BLI buffer.
The data were aligned to a baseline prior to association step
and fit to a 1:1 binding model to calculate rate and disso-
ciation constants using Octet Data Analysis software v11.1.
The IgGs exhibiting binding to MERS-CoV S was further
examined for the ability to compete with mAb G4, the only
S2-targed antibody MERS-S antibody with a defined epitope
(Pallesen et al., 2017). Four-fold molar excess of G4 Fab
was preincubated with 100 nM MERS-S at room tempera-
ture for 10 min. The IgG being tested was loaded on AHC
sensors and then dipped into either 100 nM apo MERS-S or
100 nM G4-presaturated MERS-S. G4 IgG was also
included in one set of the experiments as a control. The data
were plotted as the difference between the binding level of
G4-saturated and apo MERS-S, normalized to the binding
level of apo MERS-S to the IgG of interest.

Surface plasmon resonance. To accurately determine the
binding kinetics, His-tagged spike variants (MERS-CoV
S-2P, SARS-CoV S-2P and SARS-CoV-2 S-HexaPro) were
immobilized to a Ni-NTA sensorchip (GE Healthcare) to a
level of ~600 response units (RUs) using a Biacore X100
(GE Healthcare) and running buffer composed of 10 mM
HEPES pH 8.0, 150 mM NaCl and 0.05% Tween 20. Serial
dilutions of purified Fab22 were injected at concentrations
ranging from 400 to 6.25 nM over immobilized MERS-CoV
S-2P. For the SARS-CoV S-2P and SARS-CoV-2 S-HexaPro
binding experiments, Fab22 concentrations ranging from
100 to 3.13 nM were used instead. The Ni-NTA sensorchip
was regenerated between each cycle with 0.35 M EDTA, 50
mM NaOH and followed by 0.5 mM NiCl2. Response
curves were double-reference subtracted and fit to a 1:1
binding model using Biacore X100 Evaluation Software
(GE Healthcare).

Plaque reduction neutralization test (PRNT). Four-fold
serial dilutions of mAbs were combined with an average of
124 plaque-forming units of MERS-CoV (HCoV-EMC/
2012) or SARS-CoV-2 (SARS-CoV-2/human/USA/USA-
WA1/2020) in 200 μL gelatin saline (0.3% [wt/vol] gelatin
in phosphate-buffered saline supplemented with $CaCl_2$ and
$MgCl_2$) for 20 min at 37° C., and 100 μL of virus-mAb
mixture was applied to each of two confluent Vero 81 or
Vero E6 cell monolayers, respectively, in 6-well (10-$cm^2$)
plates. Monolayers were overlaid with Dulbecco's modified
Eagle's medium (DMEM) containing 1% agar following
virus adsorption for 30 min at 37° C., and plaques were
enumerated at 72 h or 96 h post-infection. Percent plaque
reduction resulting from mAb treatment (relative to
untreated virus control) was plotted as a function of $\log_{10}$
mAb concentration. Neutralization data were subjected to
five-parameter logistic regression modeling using GraphPad
PRISM 9.0.0. Minimum mAb concentrations resulting in
50% and 80% virus neutralization were interpolated from
fitted dose-response curves.

Negative stain EM for spike-Fab complexes. Purified
MERS-CoV S-2P or SARS-CoV-2 S-HexaPro were incu-
bated with 2-fold molar excess of Fab22 or Fab72 in 2 mM
Tris pH 8.0, 200 mM NaCl and 0.02% $NaN_3$ at room
temperature for 30 min. The spike-Fab complexes were
diluted to a concentration of 0.06 mg/mL in 2 mM Tris pH
8.0, 200 mM NaCl and 0.02% $NaN_3$. Each protein complex
was deposited on a CF-400-CU grid (Electron Microscopy
Sciences) that had been plasma cleaned for 30 seconds in a
Solarus 950 plasma cleaner (Gatan) with a 4:1 ratio of
O2/H2 and stained using methylamine tungstate (Nano-
probes). Grids were imaged at a magnification of 92,000×
(corresponding to a calibrated pixel size of 1.63 Å/pix) in a
Tabs F200C TEM microscope equipped with a Ceta 16M
detector (Thermo Fisher Scientific). The CTF-estimation
and particle picking were performed in cisTEM (Grant et al.,
2018). Particles were then imported into cryoSPARC
v2.15.0 for 2D classification (Punjani et al., 2017).

Figure 12A:
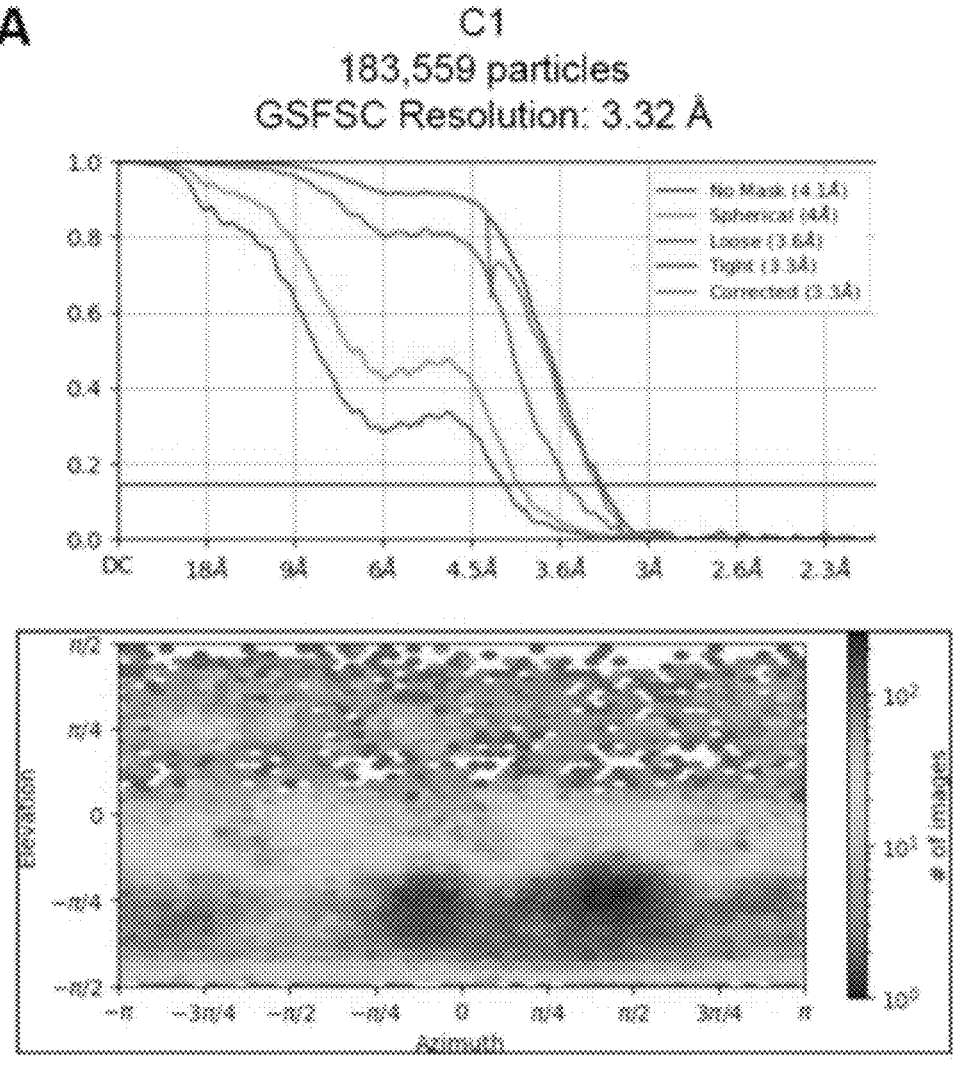
FIGS. 12A-C. Cryo-EM structure validation. FSC curves and viewing distribution plots for (FIG. 12A) MERS-CoV S-Fab 22 structure, (FIGS. 12B-C) SARS-CoV-2 S-Fab 22 structures with (FIG. 12B) 1-RBD up and (FIG. 12C) 3-RBD down generated in cryoSPARC v2.15.
Figure 12B:
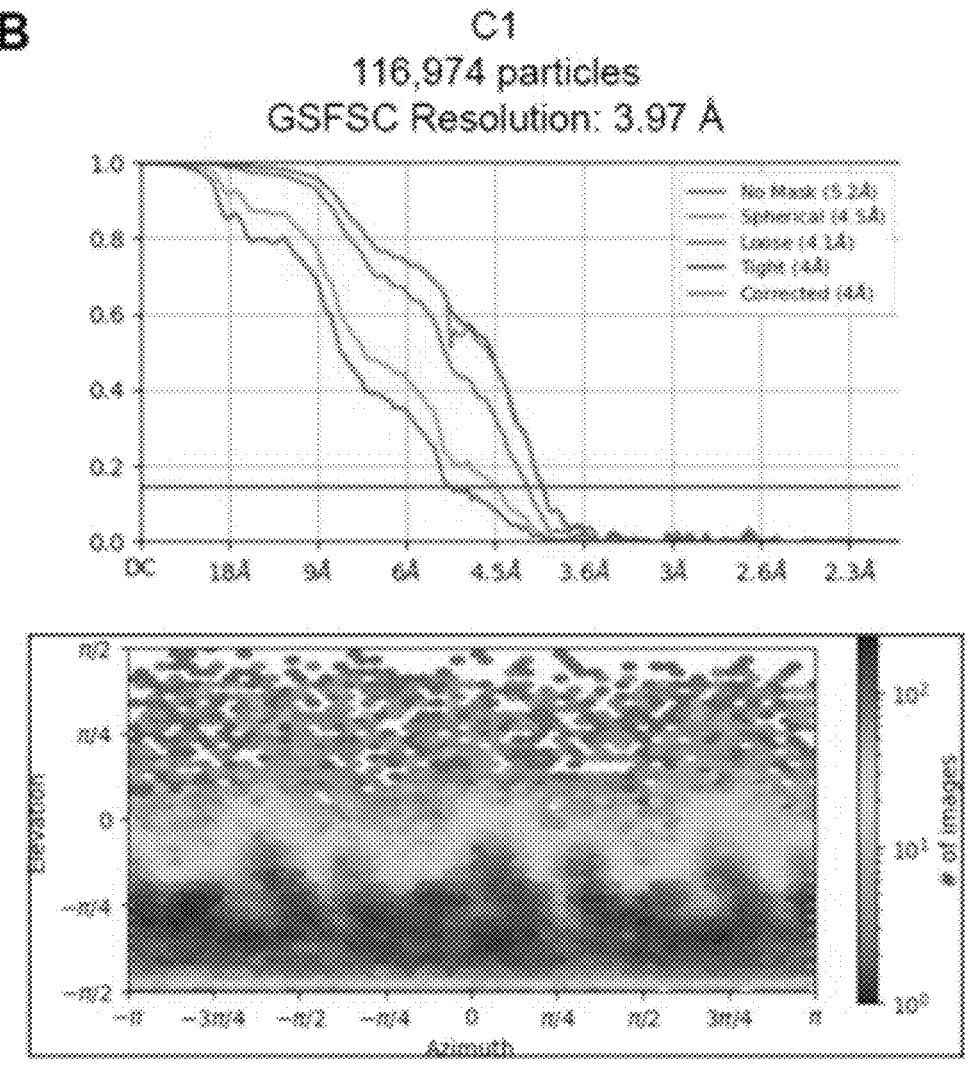
Figure 12C:
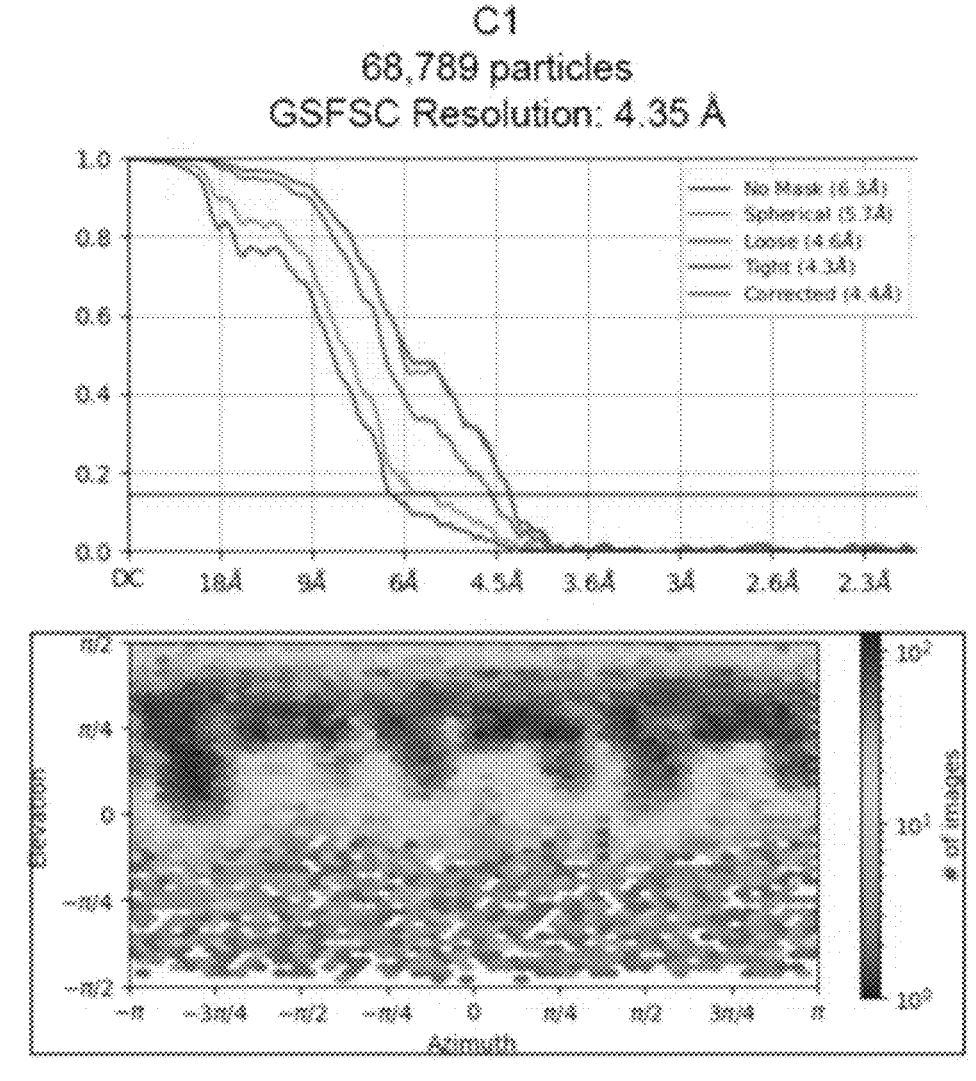

Cryo-EM sample preparation, data collection and pro-
cessing. Purified MERS-CoV S-2P at 1 mg/mL was incu-
bated with 2-fold molar excess of Fab22 in 2 mM Tris pH
8.0, 200 mM NaCl and 0.02% NaN3 at room temperature for
30 min. Sample was then deposited on a plasma-cleaned
CF-400 1.2/1.3 grid before being blotted for 5 seconds with
+1 force in a Vitrobot Mark IV (ThermoFisher) and plunge-
frozen into liquid ethane. Similarly, purified SARS-CoV-2 S
(HexaPro variant) complexed with 2-fold molar excess of
Fab22 was diluted to a concentration of 0.37 mg/mL in 2
mM Tris pH 8.0, 200 mM NaCl, 0.02% NaN3 and applied
to plasma-cleaned CF-400 1.2/1.3 grids before being blotted
for 3.5 seconds with −4 force in a Vitrobot Mark IV and
plunge-frozen into liquid ethane. For the Fab22-MERS S-2P
sample, 4,330 micrographs were collected from a single
grid. For the Fab22-HexaPro sample, 2,013 micrographs
were collected from a single grid. FEI Titan Krios (Ther-
moFisher) equipped with a K3 direct electron detector
(Gatan) was used for imaging. Data were collected at a
magnification of 22,500×, corresponding to a calibrated
pixel size of 1.07 Å/pix. A full description of the data
collection parameters can be found in Table 3. Warp was
used for motion correction, CTF estimation, and particle
picking (Tegunov and Cramer, 2019). The particle stack was
then imported into cryoSPARC v2.15.0, which was used to
curate the particles via iterative rounds of 2D classification
(Punjani et al., 2017). The final reconstructions were then
arrived at via ab initio reconstruction, heterogeneous refinement, and subsequently non-uniform homogeneous refinement of final classes. The structure validation can be found in FIGS. 12A-C.

TABLE 3

| Cryo-EM data collection and processing statistics | | |
|---|---|---|
| EM data collection | | |
| Microscope | FEI Titan Krios | FEI Titan Krios |
| Voltage (kV) | 300 | 300 |
| Detector | Gatan K3 | Gatan K3 |
| Magnification (nominal) | 22500 | 22500 |
| Pixel size (Å/pix) | 1.1 | 1.1 |
| Flux (e$^-$/pix/sec) | 8.0 | 9.1 |
| Frames per exposure | 80 | 30 |
| Exposure (e$^-$/Å$^2$) | 80 | 37.2 |
| Defocus range (μm) | 1.0-2.5 | 1.0-2.5 |
| Micrographs collected | 2,383 | 2,013 |
| Sample | MERS-CoV-2 S + Fab 22 | SARS-CoV-2 S + Fab 22 |
| 3D reconstruction statistics | | |
| | 3-RBD down | 1-RBD up | 3-RBD down |
| Particles | 89,372 | 119,974 | 68,789 |
| Symmetry | C1 | C1 | C1 |
| Map sharpening B-factor | −78.4 | −135.8 | −159.1 |
| Unmasked resolution at 0.143 FSC (Å) | 4.10 | 5.20 | 6.30 |
| Masked resolution at 0.143 FSC (Å) | 3.29 | 3.97 | 4.35 |

Example 1—Structure-Based Vaccine Design of MERS-CoV Stabilized Stem (SS) Antigens To stabilize the stem region (S2 subunit) of the spike, the Protein Repair One-Stop Shop (PROSS) was first used to computationally design stabilizing mutations based on a prefusion-stabilized structure of the MERS-CoV spike ectodomain (PDB ID: 5W9I) (Goldenzweig et al., 2016; Pallesen et al., 2017). Among 53 designs, 11 substitutions were selected and introduced in varying combinations into the S2 subunit of MERS-CoV S. The protein expression level of the mutant containing all 11 substitutions (mut11) was substantially higher than MERS S2-2P (base construct) (FIG. 2A). To further improve the protein expression and thermostability of S2, a variety of stabilization strategies were employed to design 12 different substitutions, which were added onto the mut11 background. The strategies employed include using hydrophobic residues to fill loosely packed internal cavities (FIG. 2B), disulfide bonds to lock the regions that move substantially during the pre-to-post-fusion transition (FIG. 2C), polar residues to counter internal charge imbalance (FIG. 2D), and aromatic side chains to favor pi-pi or cation-pi interactions with positively charged residues (FIG. 2B). Except for the S858C/G953C variant, all other single substitutions increased the protein expression to various extents compared to mut11. Particularly, S975M, L923W/L1033F, Q796C/S858C, T803C/K933C, S845E, A1094S and A1093R substitutions exhibited more than 10-fold higher expression than their parental construct mut11 (FIGS. 2A-D). The size-exclusion chromatography (SEC) traces of all variants showed a major trimeric peak with some minor shoulder peaks, with the retention volumes of the trimeric variants being similar to the base construct and mut11.

Next, whether the contribution of the individual substitutions comprising mut11 to protein expression and thermostability was examined by reverting each of the substitutions back to the wildtype residue. Reverting K816R, H1020Q, H1146Y or V1150T increased the protein expression relative to mut11, meaning these four substitutions in mut11 are dispensable. Thus, a new base construct containing 7 substitutions (mut7) was used for subsequent designs (FIG. 2E). To test whether the structure-based designs (previously tested individually on the mut11 background) have additive effects, a disulfide design (T803C/K933C), a cavity filling design (S975M), or a combination of both designs (S975M, T803C/K933C) was added on top of mut7. However, unlike the increase in expression for mut11, T803C/K933C decreased the protein expression relative to mut7, but increased the Tm by 1.7° C. (FIG. 7A). S975M substitution not only boosted the protein expression relative to mut7, but also enhanced the thermostability. Combining both T803C/K933C and S975M on the mut7 backbone restored the expression to a level similar to mut7 and increased Tm by 4.0° C. After iterative screening of WT reversions in mut7 S975M/T803C/K933C, A918P and V1139F were found to have adverse effects on protein expression and thermostability (FIGS. 2E and 7). Removal of A918P and V1193F resulted in the first stabilized stem antigen, MERS SS.V1, containing 7 substitutions in addition to the original 2P mutations (S975M, T803C/K933C, V958S, V983I, S1091E, L1094Q, N1132Y, V1060P, L1061P).

To evaluate the viability of MERS SS.V1 as an immunogen, large-scale production in FreeStyle 293-F cells, thermostability, and epitope integrity were investigated. After two consecutive runs of SEC, MERS SS.V1 exhibited a monodispersed trimeric peak, with a yield of 2.2 mg from 1 L of cell culture (FIG. 2H). The Tm of MERS SS.V1 is 59.9° C., which is a 6.3° C. increase relative to mut11. mAb G4 is one of very few S2-directed antibodies showing neutralizing activity to MERS-CoV (Wang et al., 2015). The binding kinetics of MERS SS.V1 to G4 IgG were comparable to those of MERS S-2P ectodomain, with apparent affinities of 8.5 nM and 13.2 nM, respectively (FIG. 8). Taken together, these results suggest that MERS SS.V1 retains the integrity of the known neutralization epitope and should be amenable to large-scale production.

Introducing disulfide linkages to lock viral glycoproteins in the prefusion conformation has proven effective in class I viral fusion proteins such as RSV F, HIV-1 Env and Ebola GP (McLellan et al., 2013; Rutten et al., 2020; Sanders et al., 2013). Although it was not successfully applied to the SARS CoV-2 spike (Hsieh et al., 2020), its feasibility on MERS SS.V1 was explored. Three disulfide designs, A838C/ 51089C, S845C/A1096C and V898C/V1022C, were introduced individually or in combination to stabilize the region proximal to the fusion peptide and central helix. With the addition of V898C/V1022C, the protein expression level increased 1.3-fold relative to MERS SS.V1 and the Tm increased by 4.0° C. (FIGS. 2F-G). Upon combination with either A838C/S1089C or S845C/A1096C substitutions, the protein expression levels increased 1.7-fold relative to MERS SS.V1 and the Tm increased by 6.3° C. Notably, both constructs exhibited a sharp monodisperse trimeric peak on SEC without any prominent shoulder peaks. This led to the MERS SS.V2 construct, which contains A838C/51089C and V898C/V1022C added onto the MERS SS.V1 background. The large-scale expression of MERS SS.V2 outperformed MERS SS.V1, yielding 9.5 mg from 1 L of FreeStyle 293-F cells (FIG. 2H).

Example 2—MERS SS Immunization Elicits Cross-Reactive β-CoV Antibodies

Figure 3F:
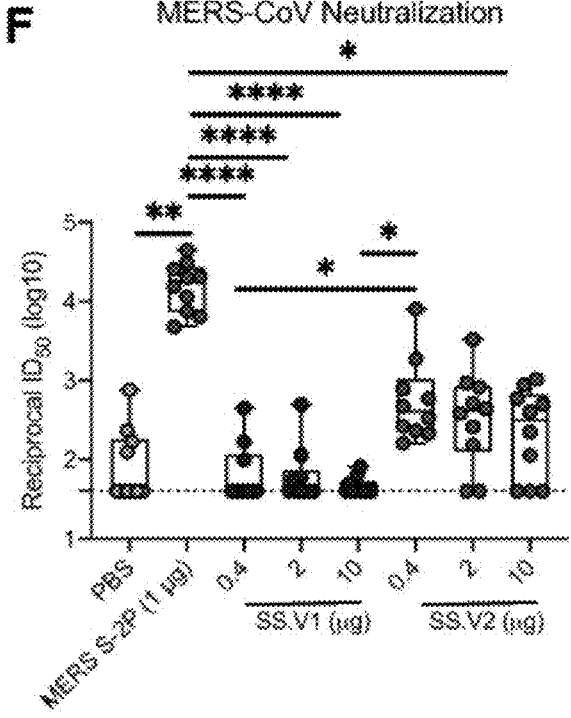

To evaluate the cross-reactive immunogenicity of MERS SS immunogens, BALB/cJ mice were immunized with 0.4, 2, or 10 µg of MERS SS.V1 or SS.V2 or the maximally effective dose of 1 µg stabilized MERS spike ectodomain (MERS S-2P) (Pallesen et al., 2017). The immunogens were administered at weeks 0 and 3 with Sigma Adjuvant System (SAS). Mice were bled 2 weeks post-boost to assess binding IgG and pseudovirus neutralizing antibody responses (FIG. 3A). All doses of both immunogens elicited robust ~$10^5$ MERS S-2P-specific reciprocal endpoint binding titers (FIG. 3B). Both MERS SS.V1 and SS.V2 elicited HKU1, SARS, and SARS-2 S-2P-specific IgG that trended toward dose-dependency; most notably at the 0.4 µg dose, heterotypic SARS and SARS-2 S-2P-specific binding IgG responses were more significant in mice immunized with SS.V1 compared to mice immunized with SS.V2 (FIGS. 3C-E). Conversely, neutralizing antibody responses against a pseudo-typed lentivirus reporter expressing MERS-CoV S was not dose-dependent. As expected, both SS immunogens elicited significantly fewer neutralizing antibodies than MERS S-2P given the lack of the S1 subunit in the SS immunogens. While MERS SS.V1 elicited only modest baseline neutralizing antibody responses (up to a geometric mean ID50 titer, GMT=1/156), SS.V2 induced stronger neutralization responses with GMT of 1/550 (FIG. 3F). Altogether, these data corroborate that the introduction of stabilizing disulfide bonds into the SS.V1 backbone promotes the production of more potently neutralizing MERS-CoV S2-specific antibodies. Additionally, they underscore the importance of targeting conserved epitopes to induce broadly specific antibody responses.

Figure 4A:
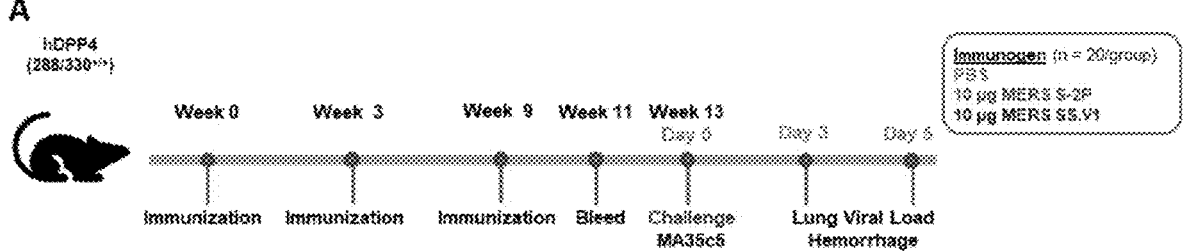

Example 3—MERS SS Protects Humanized-DPP4 Mice Against Lethal MERS-CoV Challenge In order to assess the ability of MERS stabilized stems to protect against lethal MERS-CoV challenge, 288/330+/+ mice (Cockrell et al., 2016) were immunized with 10 µg of MERS SS.V1 or S-2P, adjuvanted with SAS. Mock-immunized mice received PBS. 288/330+/+ mice express human DPP4 and harbor localized lung viral replication and succumb to lethal doses of mouse-adapted (MA) MERS-CoV maM35c4 (Douglas et al., 2018). Giving three immunogen doses at weeks 0, 3, and 9, the antibody responses were then assessed two weeks post-boost and challenged at week 13 (FIG. 4A). Firstly, ELISA revealed MERS SS.V1 elicits similar levels of robust ~$10^5$ homotypic binding IgG as MERS S-2P (FIG. 4B). However, stem-specific binding antibodies were sub-neutralizing as MERS SS.V1-immunized mice had significantly reduced homotypic pseudovirus neutralizing antibody responses (GMT=1/185) as compared to mice receiving MERS S-2P (GMT=1/5758), similar to BALB/cJ mice in FIG. 3F. In fact, only 5 out of 20 MERS SS.V1-immunized 288/330+/+ mice had detectable neutralizing antibody responses (FIG. 4C).

Following challenge, mice immunized with either MERS S-2P or MERS SS.V1 demonstrated no weight loss throughout the course of infection. Conversely, mice in the PBS control group demonstrated severe clinical presentations and succumbed to death one week post-challenge (FIG. 4D). At day 3 post-challenge, the day of peak lung viral titers in this model, MERS S-2P-immunized mice had no detectable lung viral load, and MERS SS.V1-immunized mice hovered about the viral detection limit (geometric mean PFU per lung lobe=167) (FIG. 4E). At day 4 post-challenge, MERS SS.V1 and S-2P-immunized mice alike had cleared viral replication, contrasting against PBS-immunized mice, which presented 2×$10^6$ geometric mean PFU per lung lobe (FIG. 4F). In line with trends of viral replication among SS.V1 and S-2P-immunized mice, at both days 3 and 5 post-challenge there was little to no distinguishable pulmonary hemorrhage; indicating that both vaccines effectively impeded infection and further prevented substantial lung disease (FIG. 4G-H). These findings emphasize the utility of eliciting protective immunity by targeting epitopes outside of immunodominant and neutralization sensitive S1 sites.

Example 4—Discovery of Pan-CoV Antibodies from MERS SS-Immunized Mice

Figure 9C:
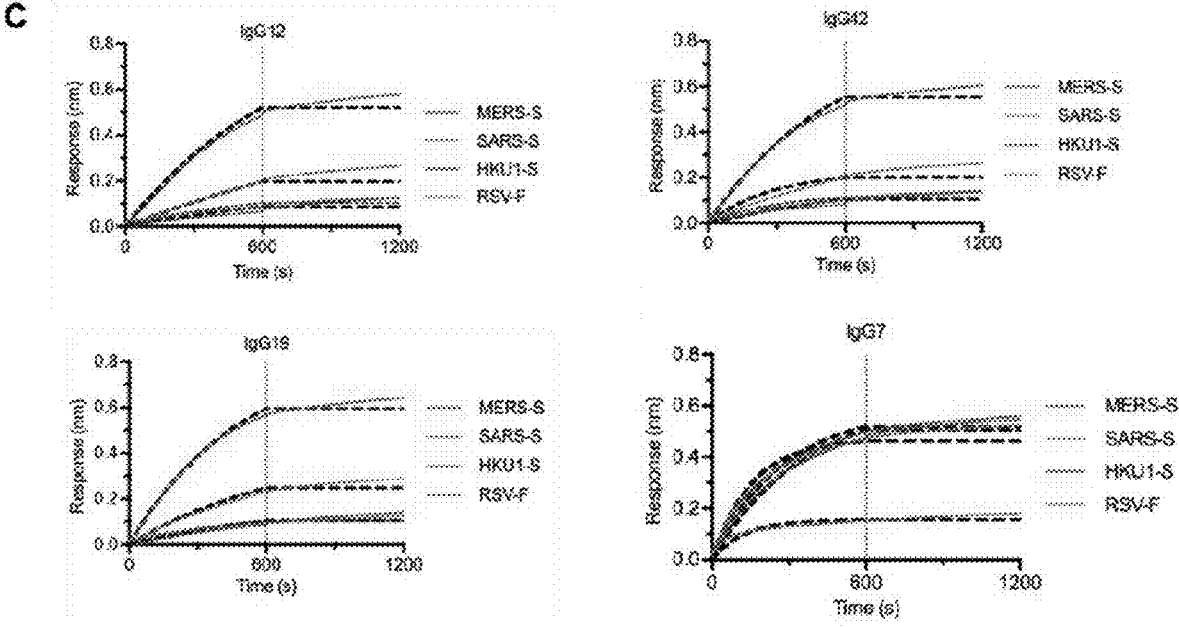
Figure 10A:
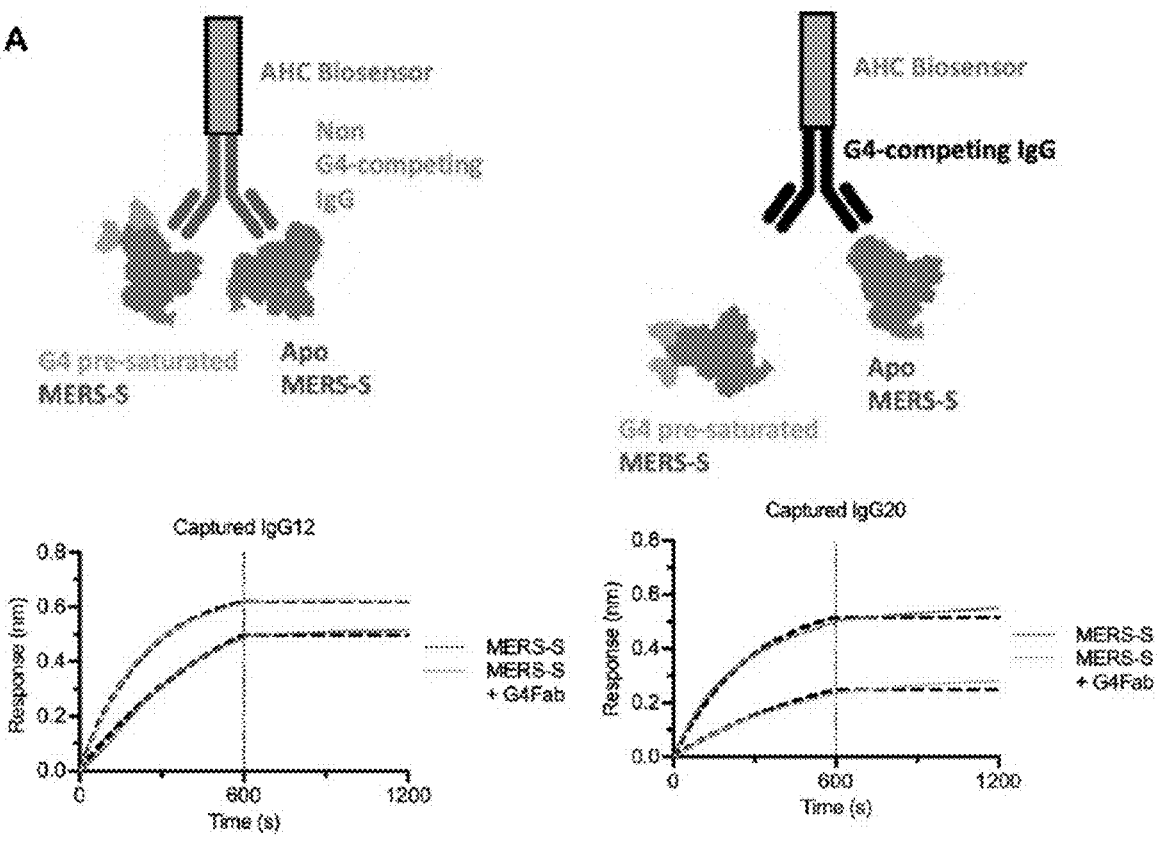
FIGS. 10A-B. Two third of MERS SS.V1 elicited mAbs bind to the regions other than G4 binding loop.
Figure 10B:
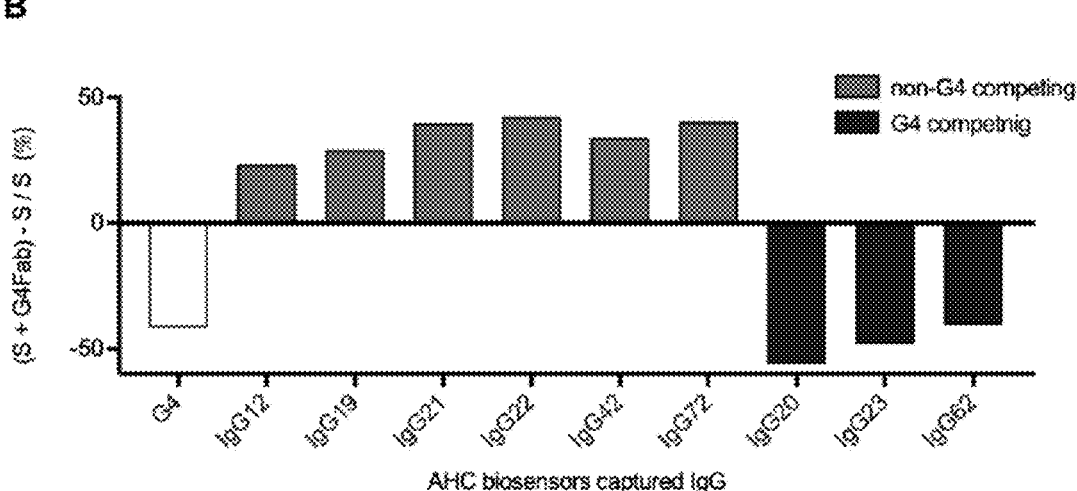

Next, AbCellera's single B cell technology was used to isolate cross-reactive monoclonal antibodies from the spleen, thymus and lymph nodes of mice immunized with MERS SS.V1 antigen. Using HCoV HKU1 S-2P, SARS-CoV S-2P, MERS-CoV S-2P, and MERS SS.V1 as probes, 146 antibodies with a diverse spectrum of specificities to the β-CoV spikes were discovered. Antibodies exhibiting broader spike reactivities, higher frequencies, and unique CDR3s in both heavy and light chains were selected for in order to cover a wide distribution of the germline family. The selected IgGs were then expressed recombinantly in vitro and characterized by binding specificities to β-CoV prefusion-stabilized S, namely HCoV-HKU1 S-2P, MERS-CoV S-2P, and SARS-CoV S-2P. IgG20, IgG23 and IgG62 demonstrated cross-reactive binding to MERS- and SARS-CoV S with higher apparent affinity to the former (FIG. 9A). Intriguingly, IgG21, IgG22 and IgG72 were also MERS- and SARS-specific, but the association rates of these mAbs to SARS-CoV S were nearly 5-fold higher than to MERS-CoV S (FIG. 9B). In contrast, IgG12, IgG19 and IgG42 only bound to MERS-CoV S (FIG. 9C). Competitive binding experiments with G4, the only MERS S2-targeted antibody with a structurally defined epitope, were also performed (Pallesen et al., 2017). One third of selected mAbs (IgG20, IgG23 and IgG62) competed with G4 binding to MERS- CoV S (FIG. 10). By contrast, IgG12, IgG19, IgG21, IgG22, IgG42, and IgG72 appeared to bind to regions outside of the G4 epitope.

Example 5—IgG22 Binds to Multiple CoV Spikes and Neutralizes Authentic MERS-CoV IgG22 and the clonally related IgG72 are two of the cross-reactive antibodies that exhibited faster association to SARS-CoV S than MERS-CoV S (FIG. 9B). To determine the kinetics of their interactions, surface plasmon resonance experiments were performed where Fab was flowed over spike ectodomain immobilized to a sensor chip. The binding affinity of Fab22 to MERS-CoV S was comparable to those of SARS-CoV S and SARS-CoV-2 S, with KD values of 2.9 nM, 7.2 nM, and 6.7 nM, respectively (FIGS. 5A-C). However, Fab22 exhibited distinct binding kinetics to MERS-CoV S, featuring a much slower on-rate and off-rate than SARS-CoV or SARS-CoV-2 S. The neutralization activities of selected mAbs were examined against authentic MERS-CoV. IgG22 and IgG72 exhibited potent neutralizing activity, with $IC_{50}$ values of 0.12 µg/mL and 2.45 µg/mL, respectively (FIG. 5D). On the other hand, IgG20, IgG21 and IgG42 showed no neutralization activity against MERS-CoV. Interestingly, IgG22 and IgG72 failed to neutralize authentic SARS-CoV-2 (FIG. 5E), which may be due to the faster off-rate of IgG22 to SARS-CoV-2.

Example 6—Cryo-EM Structure of Fab22 Bound to the MERS-CoV Spike

To investigate Fab22 and Fab72 binding sites on the spikes, negative stain electron microscopy (nsEM) analysis were performed for the Fab-spike complexes. 2D classification showed three distinct densities for Fab22 attached to the S2 stalk region of MERS-CoV S-2P, a region that undergoes substantial conformation changes during the pre-to-postfusion transition (FIG. 11A). Interestingly, Fab72 also binds to a similar region of S2 in proximity to HR2 (FIG. 11B). Given that binding of HR2 could potentially prevent virus-cell membrane fusion, a cryo-EM structure of Fab22 bound to MERS S-2P was determined. Resembling the nsEM analysis, three distinct Fab9 densities were seen from multiple 2D classes (FIG. 5F). The initial 3D reconstruction exhibited a single conformation of the spike, with all three RBDs in the down conformation. A total of 183,556 particles led to a 3.3 Å reconstruction with well-defined side chain densities at the core of S2. Three Fab densities could be visualized at the bottom stalk of S2, although one of the Fabs displayed a broader than usual Fab density. It is possible that the highly flexible nature of the stalk-HR2 region could lead to broadened Fab density. Therefore, the initial set of particles was subjected to two additional rounds of heterogeneous refinement to sort out 3D classes with diverse Fab orientations. A 3D reconstruction (3.3 Å) from about half of the total particles (48.7%) was obtained, which demonstrated three distinct Fab densities bound to the spike. Interestingly, both reconstructions displayed three-RBD-down conformations. Focused refinement on the Fab22 densities was attempted, but the Fab-spike interface could not be resolved.

Example 7—CryoEM Structure of Fab22 Bound to the SARS-CoV-2 Spike

Resembling the Fab22—MERS-CoV S complex, nsEM analysis showed that Fab22 binds to the stalk region of SARS-CoV-2 S (FIG. 11C). To ascertain the discrepancy between the MERS-CoV and SARS-CoV-2 neutralization by IgG22, a high-resolution structure of Fab22 bound to SARS-CoV-2 S HexaPro, a prefusion-stabilized spike (Hsieh et al., 2020), was attempted to be determined. The initial 3D reconstruction exhibited a disc-shaped Fab density beneath the helical stalk of the globular ectodomain. After two additional rounds of heterogeneous refinement, two different conformations of the spikes were identified: one-RBD-up at 4.0 Å (53% of the total particles) and three-RBD-down at 4.4 Å (31% of the total particles) (FIGS. 6A-B). Although Fab22 density was not well defined, the Fab binding site on the spike could be located to the helical stalk, which is only resolved in the full-length spike model (PDB: 6XR8) (FIG. 6C). Sequence alignments of the helical stalk show that, among the β-CoVs, HCoV-HKU1 is the least conserved in this region. This could explain why IgG22 has the weakest affinity to the HCoV-HKU1 S. To further narrow down the binding site, two C-terminal truncations of the spike variants were constructed: ΔHR2 (1-1160) and Δstalk (1-1142). In line with the cryo-EM map, Fab22 retained the affinity to HexaPro-AHR2 but completely lost the binding to HexaPro-Δstalk (FIG. 6D). Collectively, these data demonstrate that the conserved helical stalk region between residues 1142 and 1160 is a novel epitope with the potential to elicit cross-reactive S2-targeted antibodies.

Example 8—Inter-Protomer Disulfide Bonds and Salt Bridges

Figure 13:
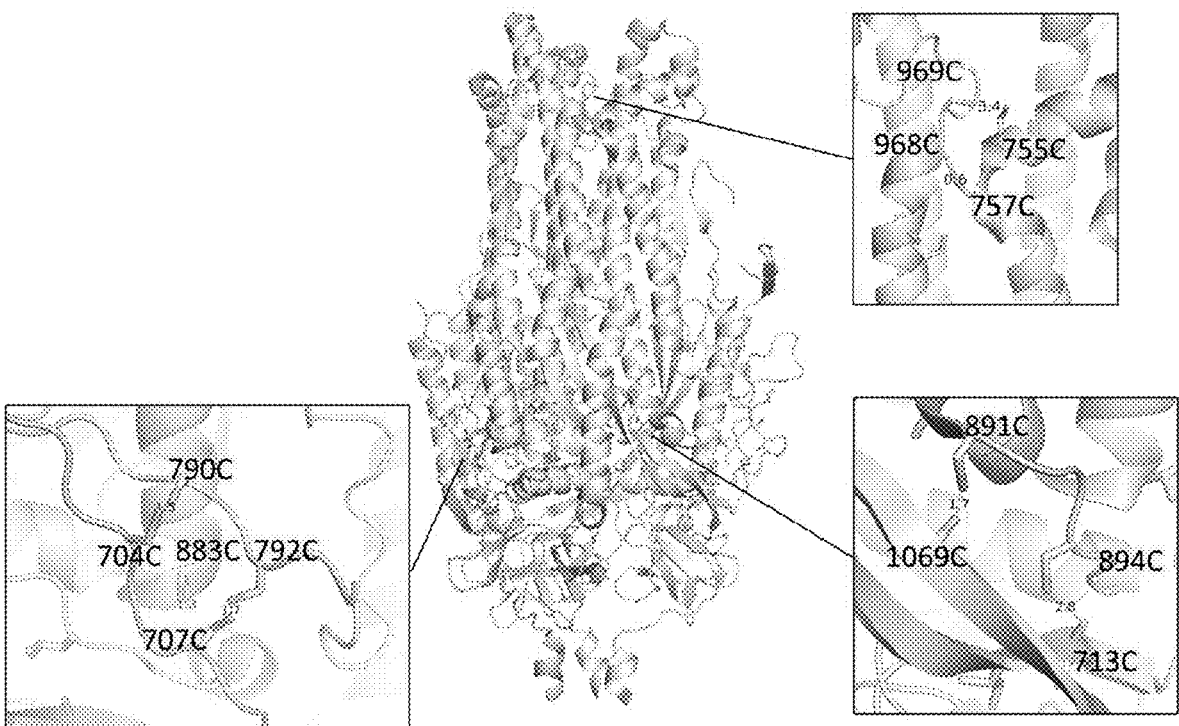
FIG. 13. Inter-protomer Disulfide Design for SARS-CoV-2 Stem-only Antigen.
Figure 14A:
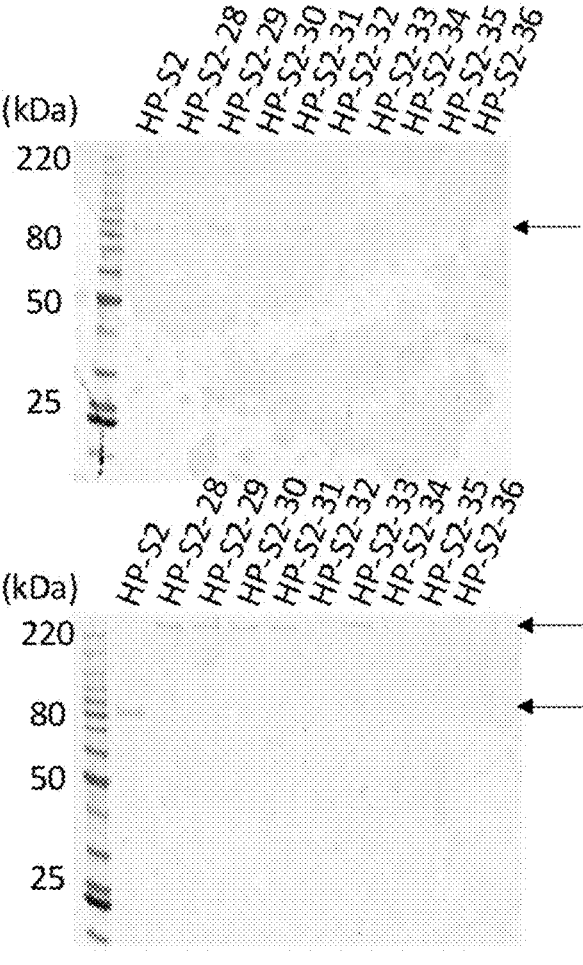
FIGS. 14A-C. Characterization of SARS-CoV-2 S2 inter-protomer disulfide designs.
Figure 14B:
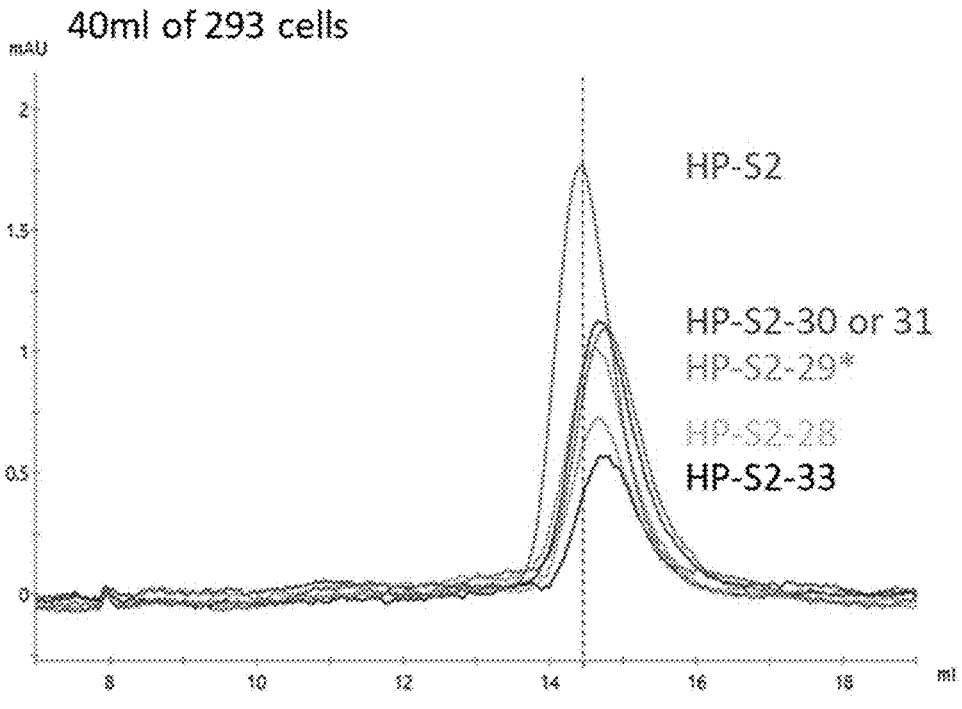
Figure 14C:
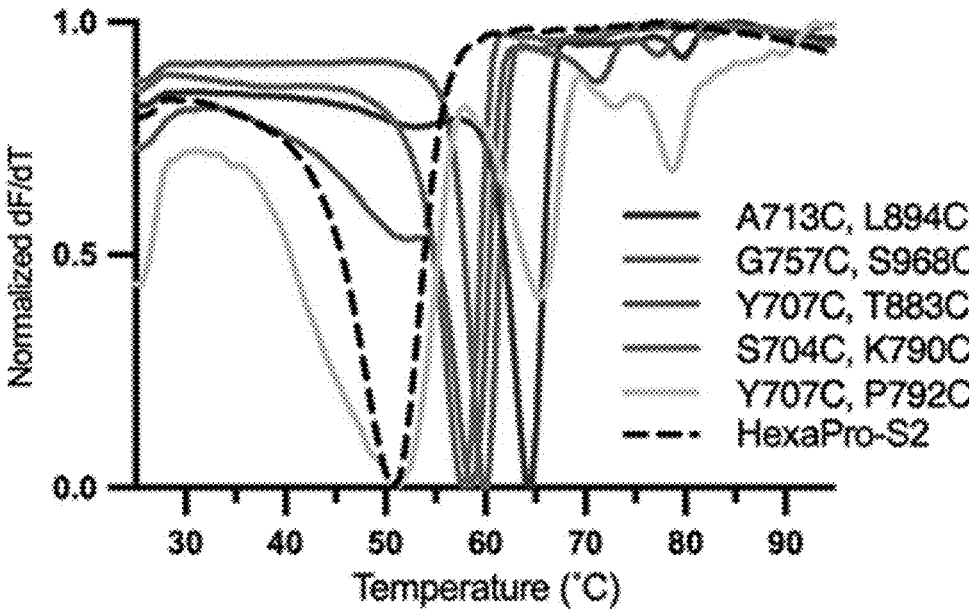

To increase the stability of S2 subunit trimers in the prefusion conformation, inter-protomer disulfide bonds were engineered into the SARS-CoV-2 S2 antigen having background substitutions of F817P, A892P, A899P, A942P, K986P, and V987P (with positions relative to SEQ ID NO: 4) as follows: S704C/K790C (named S2-30), Y707C/P792C (named S2-28), Y707C/T883C (named S2-29), Q755C/N969C (named S2-32), G757C/S968C (named S2-33), G891C/P1069C (named S2-34), A713C/L894C (named S2-31), S1030C/D1041C (named S2-35), and G1035C/V1040C (named S2-36) (FIG. 13). Five of the designs (S2-28, S2-29, S2-30, S2-31, and S2-33) enhanced thermostability of the trimer (FIGS. 14A-C; Table 4).

TABLE 4

| Inter-protomer Disulfide Designs | | | |
| --- | --- | --- | --- |
| Code | Substitutions | Trimer formation | Tm |
| S2-28 | Y707C, P792C | yes | triple peaks |
| S2-29 | Y707C, T883C* | yes, but has some dimers | increase 7.7C |
| S2-30 | S704C, K790C | yes | increase 7.1C |
| S2-31 | A713C, L894C* | yes, but has some dimers | increase 13.7C |
| S2-32 | Q755C, N969C | no | n.d. |
| S2-33 | G757C, S968C | yes | increase 8.8C |
| S2-34 | G891C, P1069C | no | n.d. |
| S2-35 | S1030C, D1041C | no | n.d. |
| S2-36 | G1035C, V1040C | no | n.d. |

Figure 15A:
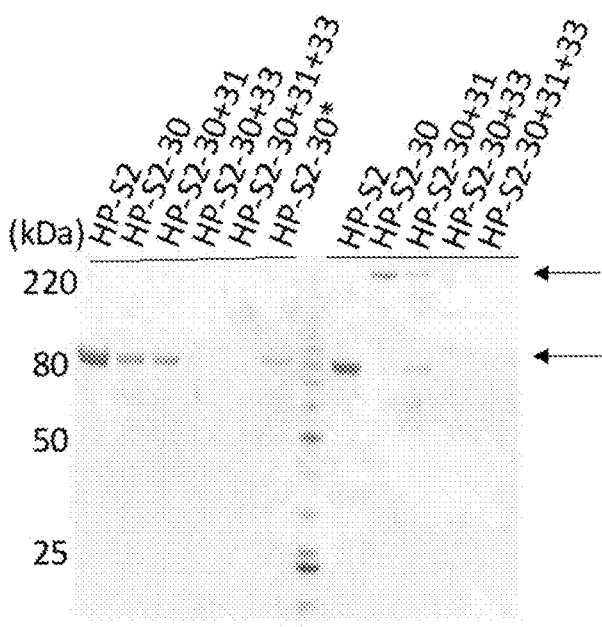
FIGS. 15A-C. Characterization of SARS-CoV-2 S2 combinatorial inter-protomer disulfide designs.
Figure 15B:
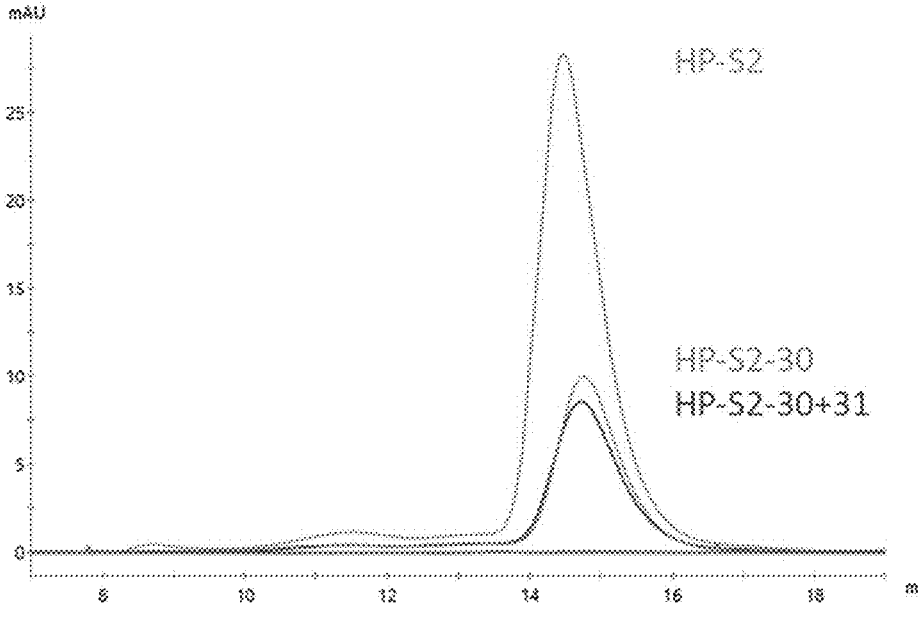
Figure 15C:
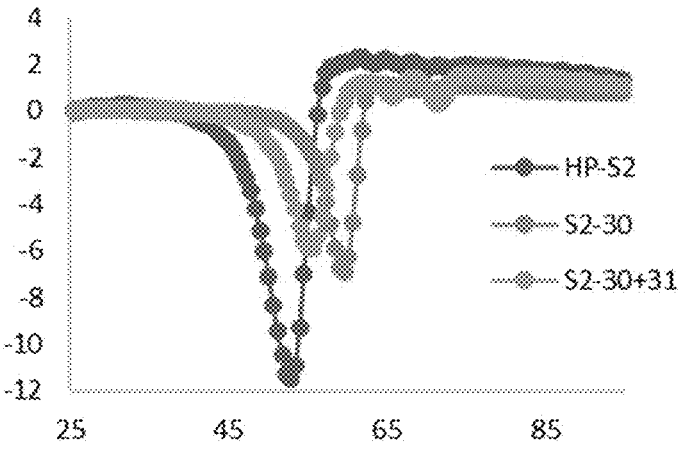

*forms mixtures of dimer and trimer on non-reducing SDS PAGE
n.d. = not determined S2-30 was selected as the lead for further engineering. In particular, S2-30 was combined with S2-31 and/or S2-33. S2-30+31 decreased both expression and Tm, as well as forming a mix of trimer and monomer fractions (FIGS. 15A-C). S2-30+33 and S2-30+31+33 both abolished expression.

Figure 16A:
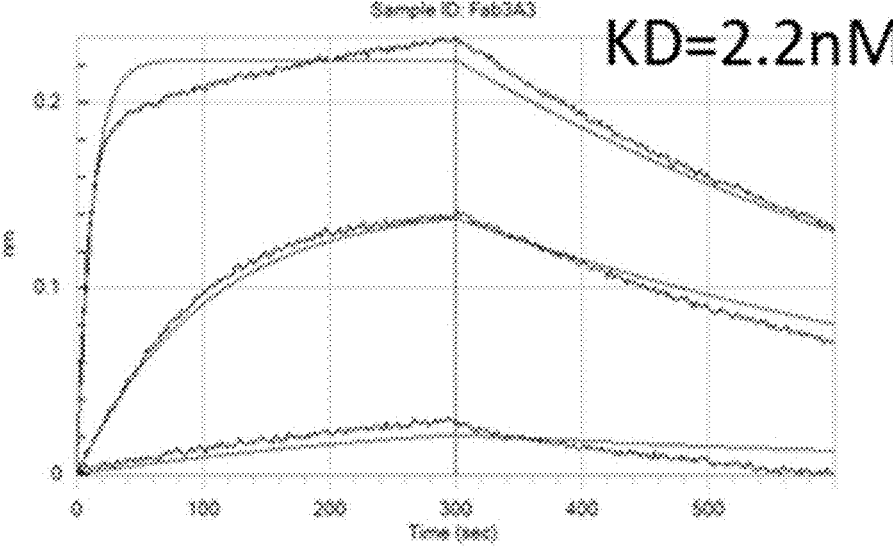
FIGS. 16A-C. Characterization of SARS-CoV-2 S2-30.
Figure 16B:
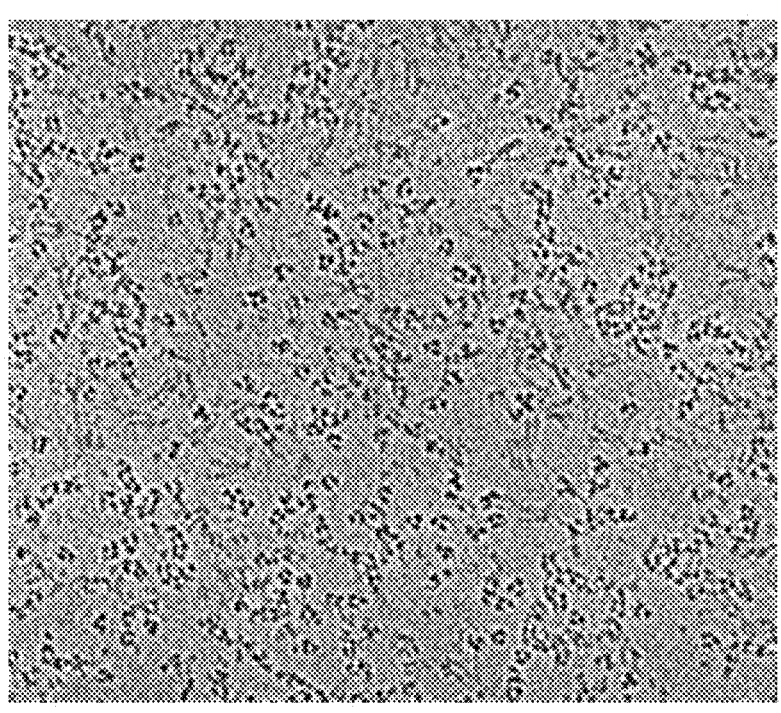
Figure 16C:
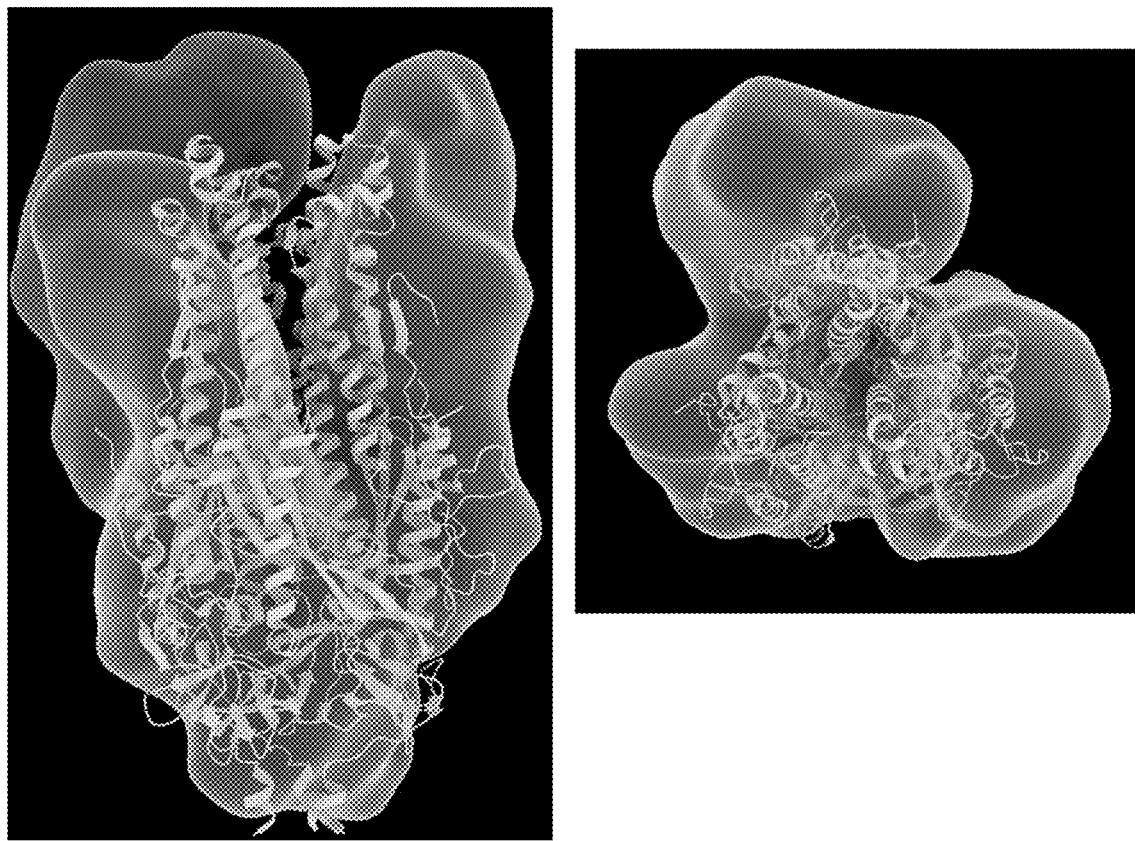

Fab3A3, which is a monoclonal antibody that binds a conformational epitope in the flexible hinge region at the S2 (Huang et al., "Identification of a conserved neutralizing epitope present on spike proteins from all highly pathogenic coronaviruses", bioRxiv, doi: https://doi.org/10.1101/ 2021.01.31.428824), was tested for its binding affinity to S2-30. Fab3A3 displayed a Kd value of 2.2 nM for binding to S2-30, indicating that S2-30 binds tightly to Fab3A3 (FIG. 16A). Negative stain electron microscopy (nsEM) analysis was performed on S2-30, indicating that S2-30 splays open at the apex (FIGS. 16B-C).

Figure 17A:
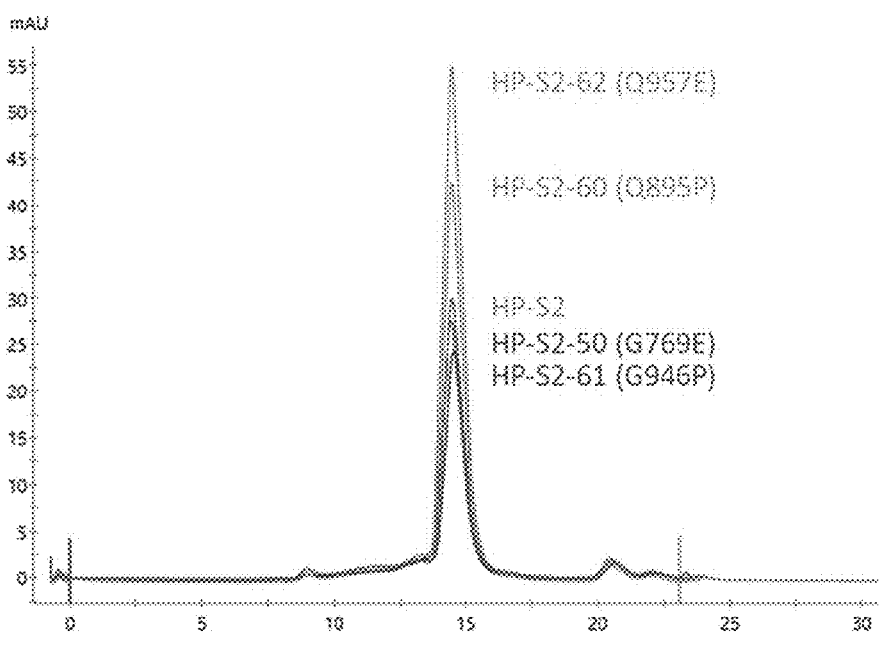
FIGS. 17A-D. Characterization of SARS-CoV-2 S2-30 in combination with interprotomer salt bridges and altered stalks.
Figure 17B:
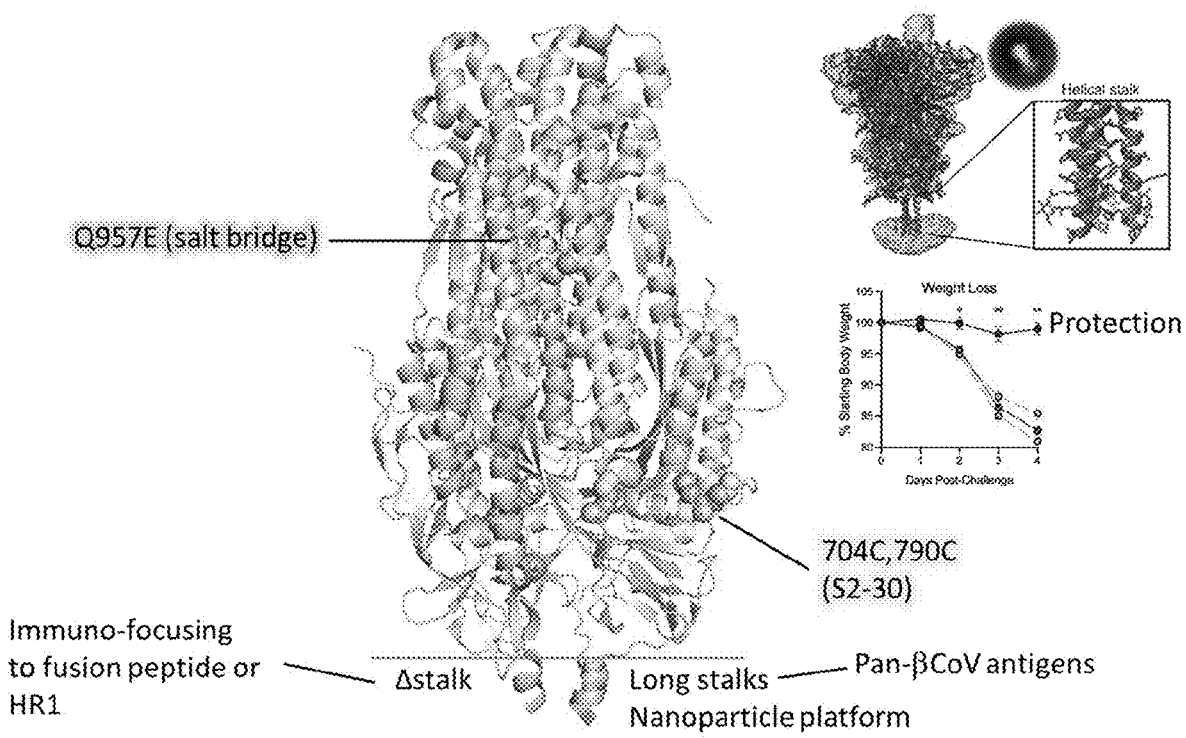
Figure 17C:
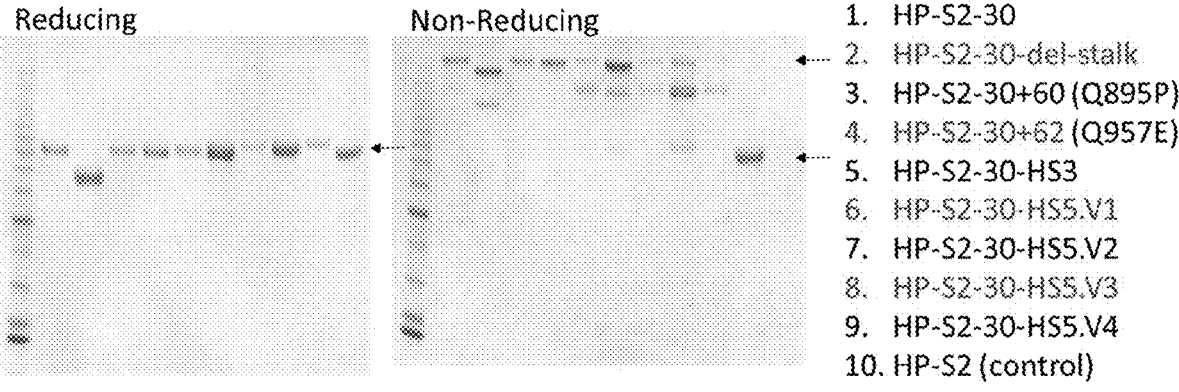
Figure 17D:
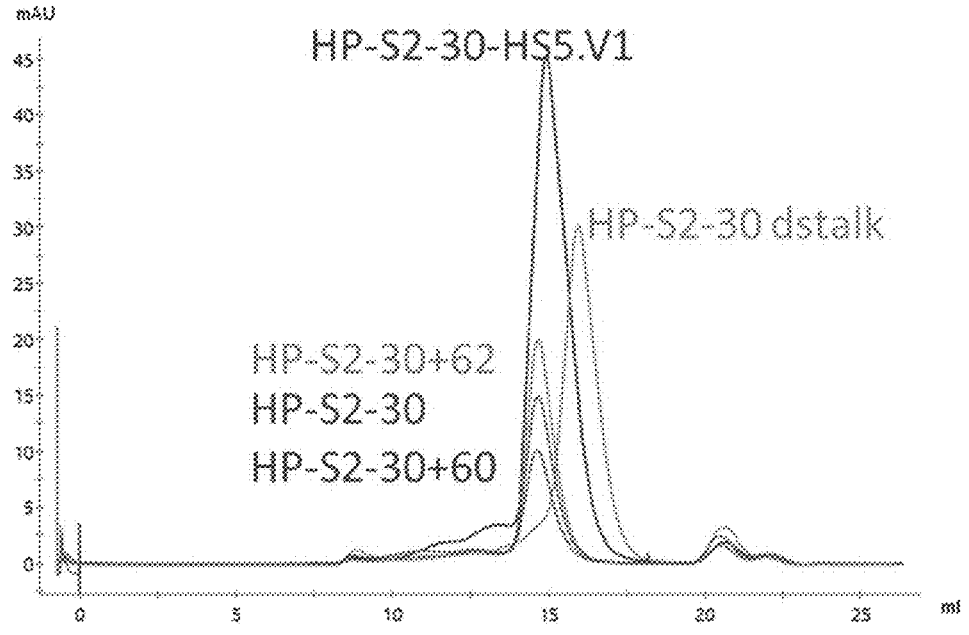
Figure 18A:
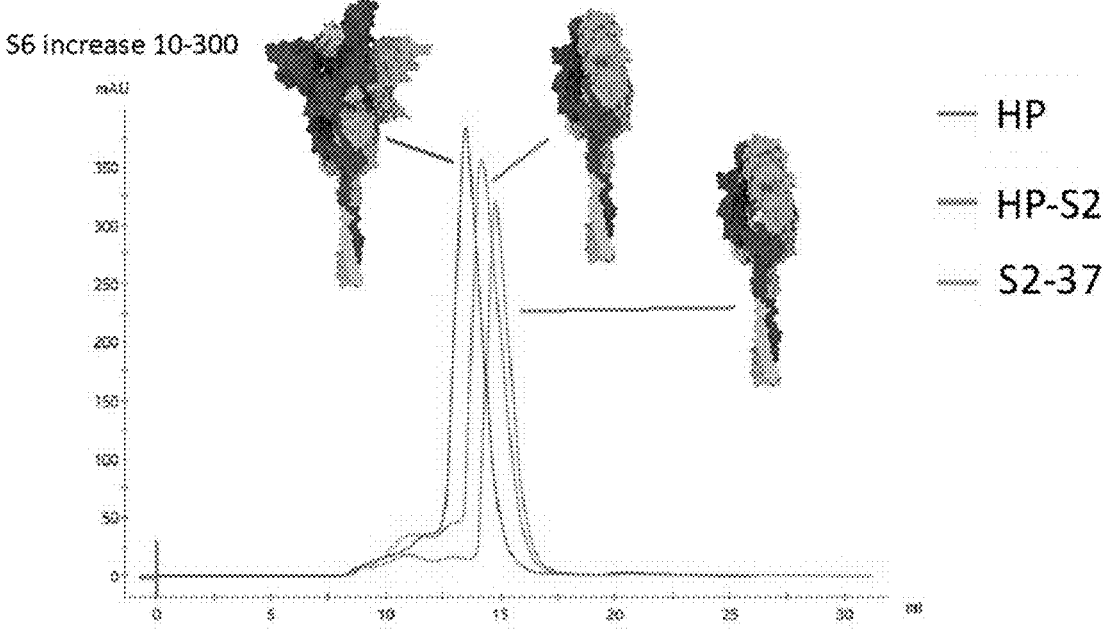
FIGS. 18A-C. Large scale expression.
Figure 18B:
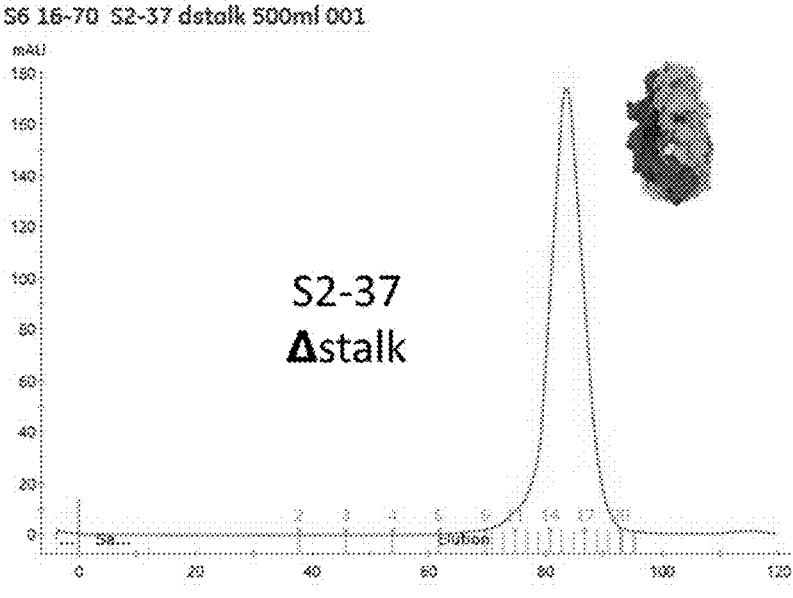
Figure 18C:
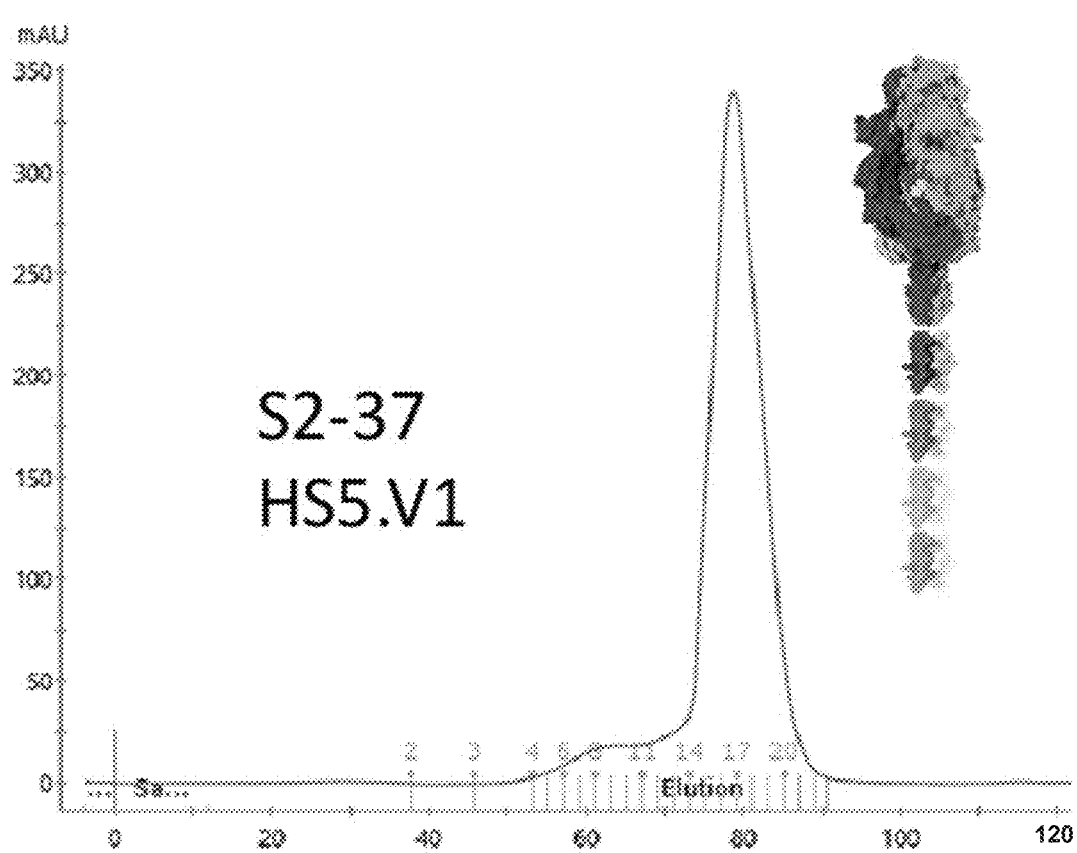

Next, an interprotomer salt bridge (Q957E) and an additional proline (Q895P) were, independently, added on top of S2-30 and found to increase protein expression (FIG. 17A). Further, S2-30 was modified to have an altered stalk or no stalk. The helical stalk region can serve as an epitope to elicit pan-beta-coronavirus-targeted antibodies. However, removing the stalk may be desired for generating an antigen that immuno-focuses on the fusion peptide or HR1 (FIG. 17B). Five long helical stalks were tested by replacing amino acids equivalent to positions 1162-1273 of SEQ ID NO: 2 with the following: HS3, which consists of the SARS, MERS, and HKU1 stalks linked directly together (SEQ ID NO: 7); HS5.V1, which consists of the SARS, OC43, HKU1, MERS, and HKU9 stalks linked directly together (SEQ ID NO: 8); HS5.V2, which consists of the SARS, OC43, HKU1, MERS, and HKU9 stalks linked directly together and with an Fd domain inserted between the HKU1 and MERS stalks (SEQ ID NO: 9); HS5.V3, which consists of the SARS, OC43, HKU1, MERS, and HKU9 stalks linked together with a short GS linker (SEQ ID NO: 10); and HS5.V4, which consists of the SARS, OC43, HKU1, MERS, and HKU9 stalks linked together with a short GS linker and with an Fd domain inserted between the HKU1 and MERS stalks (SEQ ID NO: 11). Both of the HS5.V1 stalks and Δstalk versions of S2-30 increased protein expression (FIGS. 17C-D). The S2-30 Δstalk variant yielded about 3 mg of protein from a 500 mL culture. Adding Q957E (S2-62) on the background of S2-30 also increased protein expression (FIGS. 17C-D), and we named this construct S2-37. Both of the HS5.V1 stalks and Δstalk versions of S2-37 variants yielded about 3 mg of protein from a 500 mL culture. The S2-37, S2-37 Δstalk, 52-37-HS5.V1 variants along with HexaPro (HP) and HP-S2 (FIGS. 18A-C) all generated a homogeneous monodisperse peak from a large scale culture, and will be used as immunogens for animal protection experiments.

To investigate whether the design effectively locked the S2-only antigen in the prefusion conformation, a crystal structure of S2-37 Δstalk (HexaPro-SS-Δstalk) was determined. The protein complex crystallized in space group R3 and a dataset was collected to a resolution of 3.2 Å (FIG. 19A). One protomer of HexaPro S (PDB ID: 6XKL) was used as a search model for molecular replacement, and twin law was applied during the Phenix refinement to overcome twinning issue. After model building and refinement, the structure had an Rwork and Rfree of 23.5% and 27.1%, respectively. Interestingly, two protomers in one asymmetric unit exhibited a head-to-head arrangement with one protomer orientated upside down, making upper half of the central helices pack against each other. Most importantly, HexaPro-SS-Δstalk presented as a prefusion conformation and formed a trimer when crystallographic symmetry was applied (FIG. 19A). The cysteine substitutions (Cys704/Cys790) from symmetry mates are in proximity to each other to form disulfide bonds, but Glu957 could not form a salt bridge with Arg765 from the neighboring protomer. In comparison with the S2 subunit from HexaPro S structure (PDB ID: 6XKL), HexaPro-SS-Δstalk is splayed apart at the trimer apex with central helices moving ~15° further away from 3-fold axis (FIGS. 19B-C). Given the open conformation of the structure could be attributed to crystal packing artifact, the inventors examined whether HexaPro-SS-Δstalk could sample multiple conformations in vitreous ice. The representative micrograph and 2D classification are shown in FIGS. 20A-B. After heterogenous refinement, at least three distinct volumes having the apex of S2 in a closed, semi-open and fully open conformations were reconstructed (FIG. 20C). While the low resolution of 3D reconstructions prevents the inventors from building an atomic model, all three conformations are evidently prefusion trimers, which is consistent with our crystallographic structure. Taken together, the interprotomer disulfide-stabilized S2-only antigen presents multiple prefusion conformations with the apex opening in a range of flexibility.

Figure 21B:
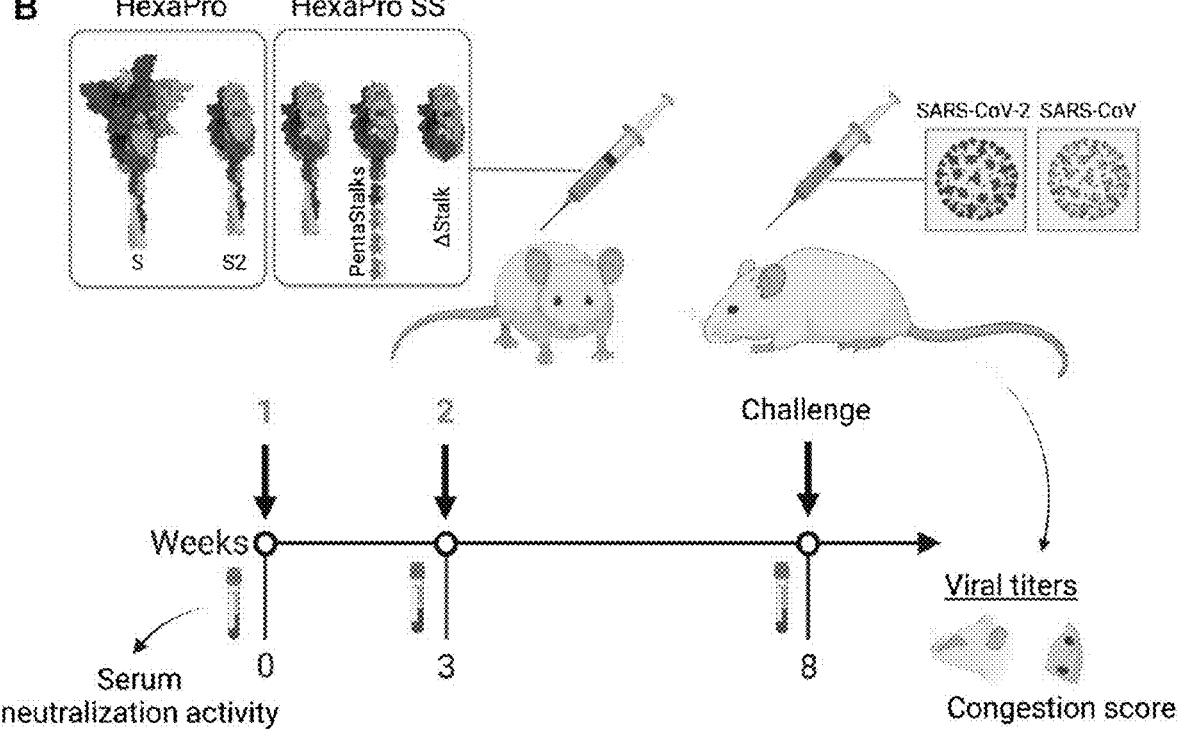

Next, the immunogenicity of the prefusion-stabilized S2 antigens will be investigated in a murine model. Ten micrograms of a variety of S2 antigens listed in FIG. 21A as well as HexaPro S will be used to prime and boost the BALB/cAnNHsd mice. The mouse serum will be taken before the prime, boost and challenge for assessing the neutralization activities against a variety of sarbecoviruses (FIG. 21B). At week 8, the immunized mice will be challenged with lethal dose of mouse adapted SARS-CoV and SARS-CoV-2 (FIG. 21B). Mock (PBS) immunization group and mock (PBS) challenge group will also be included as a control.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Baden, L. R., el Sahly, H. M., Essink, B., Kotloff, K., Frey, S., Novak, R., Diemert, D., Spector, S. A., Rouphael, N., Creech, C. B., et al. (2020). Efficacy and Safety of the mRNA-1273 SARS-CoV-2 Vaccine. The New England Journal of Medicine.

Boyoglu-Barnum, S., Hutchinson, G. B., Boyington, J. C., Moin, S. M., Gillespie, R. A., Tsybovsky, Y., Stephens, T., Vaile, J. R., Lederhofer, J., Corbett, K. S., et al. (2020). Glycan repositioning of influenza hemagglutinin stem facilitates the elicitation of protective cross-group antibody responses. Nature Communications 11, 791.

Chi, X., Yan, R., Zhang, J., Zhang, G., Zhang, Y., Hao, M., Zhang, Z., Fan, P., Dong, Y., Yang, Y., et al. (2020). A neutralizing human antibody binds to the N-terminal domain of the Spike protein of SARS CoV-2. Science (New York, N.Y.) 369, 650-655.

Choi, B., Choudhary, M. C., Regan, J., Sparks, J. A., Padera, R. F., Qiu, X., Solomon, I. H., Kuo, H.-H., Boucau, J., Bowman, K., et al. (2020). Persistence and Evolution of SARS-CoV-2 in an Immunocompromised Host. The New England Journal of Medicine 383, 2291-2293.

Cockrell, A. S., Yount, B. L., Scobey, T., Jensen, K., Douglas, M., Beall, A., Tang, X.-C., Marasco, W. A., Heise, M. T., and Baric, R. S. (2016). A mouse model for MERS coronavirus-induced acute respiratory distress syndrome. Nature Microbiology 2, 16226.

Corbett, K. S., Moin, S. M., Yassine, H. M., Cagigi, A., Kanekiyo, M., Boyoglu-Barnum, S., Myers, S. I., Tsybovsky, Y., Wheatley, A. K., Schramm, C. A., et al. (2019). Design of Nanoparticulate Group 2 Influenza Virus Hemagglutinin Stem Antigens That Activate Unmutated Ancestor B Cell Receptors of Broadly Neutralizing Antibody Lineages. MBio 10.

Corbett, K. S., Edwards, D. K., Leist, S. R., Abiona, O. M., Boyoglu-Barnum, S., Gillespie, R. A., Himansu, S., Schafer, A., Ziwawo, C. T., DiPiazza, A. T., et al. (2020a). SARS-CoV-2 mRNA vaccine design enabled by prototype pathogen preparedness. Nature 586, 567-571.

Corbett, K. S., Flynn, B., Foulds, K. E., Francica, J. R., Boyoglu-Barnum, S., Werner, A. P., Flach, B., O'Connell, S., Bock, K. W., Minai, M., et al. (2020b). Evaluation of the mRNA-1273 Vaccine against SARS-CoV-2 in Nonhuman Primates. The New England Journal of Medicine 383, 1544-1555.

Douglas, M. G., Kocher, J. F., Scobey, T., Baric, R. S., and Cockrell, A. S. (2018). Adaptive evolution influences the infectious dose of MERS-CoV necessary to achieve severe respiratory disease. Virology 517, 98-107.

Goldenzweig, A., Goldsmith, M., Hill, S. E., Gertman, O., Laurino, P., Ashani, Y., Dym, O., Unger, T., Albeck, S., Prilusky, J., et al. (2016). Automated Structure- and Sequence-Based Design of Proteins for High Bacterial Expression and Stability. Molecular Cell 63, 337-346.

Grant, T., Rohou, A., and Grigorieff, N. (2018). cisTEM, user-friendly software for single-particle image processing. ELife 7.

Grubaugh, N. D., Hodcroft, E. B., Fauver, J. R., Phelan, A. L., and Cevik, M. (2021). Public health actions to control new SARS-CoV-2 variants. Cell.

Gu, H., Chen, Q., Yang, G., He, L., Fan, H., Deng, Y.-Q., Wang, Y., Teng, Y., Zhao, Z., Cui, Y., et al. (2020). Adaptation of SARS-CoV-2 in BALB/c mice for testing vaccine efficacy. Science 369, 1603-1607.

Hsieh, C.-L., Goldsmith, J. A., Schaub, J. M., DiVenere, A. M., Kuo, H.-C., Javanmardi, K., Le, K. C., Wrapp, D., Lee, A. G., Liu, Y., et al. (2020). Structure-based design of prefusion-stabilized SARS-CoV-2 spikes. Science 369, 1501-1505.

Impagliazzo, A., Milder, F., Kuipers, H., Wagner, M. v, Zhu, X., Hoffman, R. M. B., van Meersbergen, R., Huizingh, J., Wanningen, P., Verspuij, J., et al. (2015). A stable trimeric influenza hemagglutinin stem as a broadly protective immunogen. Science (New York, N.Y.) 349, 1301-1306.

Jackson, L. A., Anderson, E. J., Rouphael, N. G., Roberts, P. C., Makhene, M., Coler, R. N., McCullough, M. P., Chappell, J. D., Denison, M. R., Stevens, L. J., et al. (2020). An mRNA Vaccine against SARS-CoV-2—Preliminary Report. The New England Journal of Medicine 383, 1920-1931.

Ke, Z., Oton, J., Qu, K., Cortese, M., Zila, V., McKeane, L., Nakane, T., Zivanov, J., Neufeldt, C. J., Cerikan, B., et al.

(2020). Structures and distributions of SARS-CoV-2 spike proteins on intact virions. Nature 588, 498-502.

Kirchdoerfer, R. N., Wang, N., Pallesen, J., Wrapp, D., Turner, H. L., Cottrell, C. A., Corbett, K. S., Graham, B. S., McLellan, J. S., and Ward, A. B. (2018). Stabilized coronavirus spikes are resistant to conformational changes induced by receptor recognition or proteolysis. Scientific Reports 8, 15701.

Krarup, A., Truan, D., Furmanova-Hollenstein, P., Bogaert, L., Bouchier, P., Bisschop, I. J. M., Widjojoatmodjo, M. N., Zahn, R., Schuitemaker, H., McLellan, J. S., et al. (2015). A highly stable prefusion RSV F vaccine derived from structural analysis of the fusion mechanism. Nature Communications 6, 8143.

Ku, Z., Xie, X., Davidson, E., Ye, X., Su, H., Menachery, V. D., Li, Y., Yuan, Z., Zhang, X., Muruato, A. E., et al. (2021). Molecular determinants and mechanism for antibody cocktail preventing SARS-CoV-2 escape. Nature Communications 12, 469.

Kupferschmidt, K. (2021). Fast-spreading U. K. virus variant raises alarms. Science 371, 9-10.

Li, F. (2016). Structure, Function, and Evolution of Coronavirus Spike Proteins. Annual Review of Virology 3, 237-261.

Liu, L., Wang, P., Nair, M. S., Yu, J., Rapp, M., Wang, Q., Luo, Y., Chan, J. F.-W., Sahi, V., Figueroa, A., et al. (2020). Potent neutralizing antibodies against multiple epitopes on SARS-CoV-2 spike. Nature 584, 450-456.

McLellan, J. S., Chen, M., Joyce, M. G., Sastry, M., Stewart-Jones, G. B. E., Yang, Y., Zhang, B., Chen, L., Srivatsan, S., Zheng, A., et al. (2013). Structure-based design of a fusion glycoprotein vaccine for respiratory syncytial virus. Science (New York, N.Y.) 342, 592-598.

Ng, K. W., Faulkner, N., Cornish, G. H., Rosa, A., Harvey, R., Hussain, S., Ulferts, R., Earl, C., Wrobel, A. G., Benton, D. J., et al. (2020). Preexisting and de novo humoral immunity to SARS-CoV-2 in humans. Science 370, 1339-1343.

Pallesen, J., Wang, N., Corbett, K. S., Wrapp, D., Kirchdoerfer, R. N., Turner, H. L., Cottrell, C. A., Becker, M. M., Wang, L., Shi, W., et al. (2017). Immunogenicity and structures of a rationally designed prefusion MERS-CoV spike antigen. Proceedings of the National Academy of Sciences of the United States of America 114, E7348—E7357.

Polack, F. P., Thomas, S. J., Kitchin, N., Absalon, J., Gurtman, A., Lockhart, S., Perez, J. L., Pérez Marc, G., Moreira, E. D., Zerbini, C., et al. (2020). Safety and Efficacy of the BNT162b2 mRNA Covid-19 Vaccine. The New England Journal of Medicine 383, 2603-2615.

Punjani, A., Rubinstein, J. L., Fleet, D. J., and Brubaker, M. A. (2017). cryoSPARC: algorithms for rapid unsupervised cryo-EM structure determination. Nature Methods 14, 290-296.

Rutten, L., Gilman, M. S. A., Blokland, S., Juraszek, J., McLellan, J. S., and Langedijk, J. P. M. (2020). Structure-Based Design of Prefusion-Stabilized Filovirus Glycoprotein Trimers. Cell Reports 30, 4540-4550.e3.

Sanders, R. W., Derking, R., Cupo, A., Julien, J.-P., Yasmeen, A., de Val, N., Kim, H. J., Blattner, C., de la Peña, A. T., Korzun, J., et al. (2013). A next-generation cleaved, soluble HIV-1 Env trimer, BG505 SOSIP.664 gp140, expresses multiple epitopes for broadly neutralizing but not non-neutralizing antibodies. PLoS Pathogens 9, e1003618.

Siebert, D. N., Bosch, B. J., van der Zee, R., de Haan, C. A. M., and Rottier, P. J. M. (2003). The Coronavirus Spike Protein Is a Class I Virus Fusion Protein: Structural and Functional Characterization of the Fusion Core Complex. Journal of Virology 77, 8801-8811.

Starr, T. N., Greaney, A. J., Hilton, S. K., Ellis, D., Crawford, K. H. D., Dingens, A. S., Navarro, M. J., Bowen, J. E., Tortorici, M. A., Walls, A. C., et al. (2020). Deep Mutational Scanning of SARS-CoV-2 Receptor Binding Domain Reveals Constraints on Folding and ACE2 Binding. Cell 182, 1295-1310.e20.

Stewart-Jones, G. B. E., Chuang, G.-Y., Xu, K., Zhou, T., Acharya, P., Tsybovsky, Y., Ou, L., Zhang, B., Fernandez-Rodriguez, B., Gilardi, V., et al. (2018). Structure-based design of a quadrivalent fusion glycoprotein vaccine for human parainfluenza virus types 1-4. Proceedings of the National Academy of Sciences of the United States of America 115, 12265-12270.

Tang, J. W., Toovey, O. T. R., Harvey, K. N., and Hui, D. D. S. (2021). Introduction of the South African SARS-CoV-2 variant 501Y. V2 into the UK. The Journal of Infection.

Tegunov, D., and Cramer, P. (2019). Real-time cryo-electron microscopy data preprocessing with Warp. Nature Methods 16, 1146-1152.

Turoňová, B., Sikora, M., Schürmann, C., Hagen, W. J. H., Welsch, S., Blanc, F. E. C., von Billow, S., Gecht, M., Bagola, K., Horner, C., et al. (2020). In situ structural analysis of SARS-CoV-2 spike reveals flexibility mediated by three hinges. Science 370, 203-208.

Walls, A. C., Park, Y. J., Tortorici, M. A., Wall, A., McGuire, A. T., and Veesler, D. (2020). Structure, Function, and Antigenicity of the SARS-CoV-2 Spike Glycoprotein. Cell 181, 281-292.e6.

Wang, L., Shi, W., Chappell, J. D., Joyce, M. G., Zhang, Y., Kanekiyo, M., Becker, M. M., van Doremalen, N., Fischer, R., Wang, N., et al. (2018). Importance of Neutralizing Monoclonal Antibodies Targeting Multiple Antigenic Sites on the Middle East Respiratory Syndrome Coronavirus Spike Glycoprotein To Avoid Neutralization Escape. Journal of Virology 92, e02002-17.

Wang, Z., Schmidt, F., Weisblum, Y., Muecksch, F., Barnes, C. O., Finkin, S., Schaefer-Babajew, D., Cipolla, M., Gaebler, C., Lieberman, J. A., et al. (2021). mRNA vaccine-elicited antibodies to SAR-CoV-2 and circulating variants. BioRxiv: The Preprint Server for Biology.

Weisblum, Y., Schmidt, F., Zhang, F., DaSilva, J., Poston, D., Lorenzi, J. C. C., Muecksch, F., Rutkowska, M., Hoffmann, H.-H., Michailidis, E., et al. (2020). Escape from neutralizing antibodies by SARS-CoV-2 spike protein variants. ELife 9, e61312.

Widjaja, I., Wang, C., van Haperen, R., Gutiérrez-Álvarez, J., van Dieren, B., Okba, N. M. A., Raj, V. S., Li, W., Fernandez-Delgado, R., Grosveld, F., et al. (2019). Towards a solution to MERS: protective human monoclonal antibodies targeting different domains and functions of the MERS-coronavirus spike glycoprotein. Emerging Microbes & Infections 8, 516-530.

Wrapp, D., Wang, N., Corbett, K. S., Goldsmith, J. A., Hsieh, C.-L., Abiona, O., Graham, B. S., and McLellan, J. S. (2020). Cryo-EM structure of the 2019-nCoV spike in the prefusion conformation. Science 367, 1260-1263.

Wu, K., Werner, A. P., Moliva, J. I., Koch, M., Choi, A., Stewart-Jones, G. B. E., Bennett, H., Boyoglu-Barnum, S., Shi, W., Graham, B. S., et al. (2021). mRNA-1273 vaccine induces neutralizing antibodies against spike mutants from global SARS-CoV-2 variants. BioRxiv: The Preprint Server for Biology.

Yassine, H. M., Boyington, J. C., McTamney, P. M., Wei, C.-J., Kanekiyo, M., Kong, W.-P., Gallagher, J. R., Wang, L., Zhang, Y., Joyce, M. G., et al. (2015). Hemagglutinin-stem nanoparticles generate heterosubtypic influenza protection. Nature Medicine 21, 1065-1070.

Zhang, J., Wu, Q., Liu, Z., Wang, Q., Wu, J., Hu, Y., Bai, T., Xie, T., Huang, M., Wu, T., et al. (2021). Spike-specific circulating T follicular helper cell and cross-neutralizing antibody responses in COVID-19-convalescent individuals. Nature Microbiology 6, 51-58.

Zhao, S., Lou, J., Cao, L., Zheng, H., Chong, M. K. C., Chen, Z., Chan, R. W. Y., Zee, B. C. Y., Chan, P. K. S., and Wang, M. H. (2021). Quantifying the transmission advantage associated with N501Y substitution of SARS-CoV-2 in the United Kingdom: An early data-driven analysis. Journal of Travel Medicine.

---

What is claimed is:

1. An engineered protein comprising an engineered coronavirus S protein ectodomain that comprises a sequence at least 90% identical to: (a) positions 14-1208 of SEQ ID NO: 4; (b) positions 14-1160 of SEQ ID NO: 4; (c) positions 319-1208 of SEQ ID NO: 4; or (d) position 684-1205 of SEQ ID NO: 4, wherein the engineered protein comprises at least one pair of substitutions relative to the sequence of SEQ ID NO: 4 or 5, said at least one pair of substitutions being: Y707C/P792C, S704C/K790C, Q755C/N969C, G757C/S968C, G891C/P1069C, or S1030C/D1041C.

2. The engineered protein of claim 1, wherein the engineered protein comprises at least one pair of substitutions, said at least one pair of substitutions being: Y707C/P792C, S704C/K790C, A713C/L894C, Q755C/N969C, G757C/S968C, G891C/P1069C, S1030C/D1041C, or G1035C/V1040C.

3. The engineered protein of claim 1, wherein the engineered protein further comprises:

(i) a substitution at a position corresponding to: T724, T752, T778, T961, I1013, H1058, S735, T859, I770, A1015, L727, S1021, Q901, S875, T912, H1088, L1141, V1040, L966, A766, T778, L938, V963, V911, N1108, V705, A893, N703, A672, A694, A1080, I1132, P862, T859, T547, N$_{978}$, T961, S758, Q762, D1118, S659, S698, R1039, V722, A930, A903, Q913, S974, D979, P728, V951, V736, L858, S884, A893, P807, S875, T791, A879, G799, A924, V826, A899, Q779, F817, L865, T866, A892, A899, T912, A570, V963; T874, S1055, V729, A1022, L894, A713, L828, H1058, L822, A1056, Q965, S1003, A972, Q992, I980, A1078, V1133, H1088, T1120, I870, S1055, T1117, D1139, T1116, Y1138, I896, G885, Q901, F1103, P1112, G889, L1034, E819, S1055, A972, I980, I1081, N1135, E819, Q1054, Q957, I1130, V1040, H1088, V1104, R1000, A944, T724, A944, S730, S730, G769, A893, Q895, K921, L922, N978, A942, G946, S975, A890, S1003; and/or (ii) a deletion corresponding to positions 829-851, 675-686, 673-684, 1161-1208, or 1142-1208; and/or (iii) a substitution of two amino acids for amino acid positions 673-686.

4. The engineered protein of claim 1, comprising an engineered disulfide bond comprising paired cysteine substitutions at positions corresponding to: S735C and T859C; I770C and A1015C; L727C and S1021C; V911C and N1108C; A672C and A694C; A1080C and I1132C; S659C and S698C; V722C and A930C; A903C and Q913C; S974C and D979C; P728C and V951C; V736C and L858C; S884C and A893C; P807C and S875C; T791C and A879C; G799C and A924C; A570C and V963C; T874C and S1055C; V729C and A1022C; L822C and A1056C; Q965C and S1003C; A972C and Q992C; I980C and Q992C; A1078C and V1133C; H1088C and T1120C; I870C and S1055C; T1117C and D1139C; T1116C and Y1138C; I896C and Q901C; G885C and Q901C; F1103C and P1112C; G889C and L1034C; E819C and S1055C; A972C and I980C; I1081C and N1135C; or E819C and Q1054C.

5. The engineered protein of claim 1, comprising a cavity filling substitution selected from: T724M, I1013F, H1058W, Q901M, S875F, H1088W, L1141F, V1040F, T778L, L938F, V963L, R1039F, V826L, A899F, Q779M, L894F, H1058F, H1058Y, V1040Y, H1088Y, V1104I, R1000Y, R1000W, A944F, T724I, A944Y, S730L, A890V, D1118F, or S1003V.

6. The engineered protein of claim 1, comprising a proline substitution selected from: F817P, L865P, T866P, A892P, A899P, T912P, A893P, Q895P, K921P, L922P, N978P, A942P, G946P, or S975P.

7. The engineered protein of claim 1, comprising an electrostatic interaction substitution selected from: T752K, T912R, L828K, L828R, S730R, T961D, A766E, P862E, T859K, Q957E, G769E, T778Q, A713S, or I1130Y.

8. The engineered protein of claim 1, comprising a combination of at least one engineered disulfide bond, at least one cavity filling substitution, at least one proline substitution, and at least one electrostatic interaction substitution.

9. The engineered protein of claim 1, comprising the following substitutions relative to the sequence of SEQ ID NO: 4 or 5: F817P, A892P, A899P, A942P, K986P, and V987P.

10. The engineered protein of claim 1, comprising the following substitutions relative to SEQ ID NO: 4: F817P, A892P, A899P, A942P, K986P, V987P, and S704C/K790C.

11. The engineered protein of claim 1, comprising the following substitutions relative to SEQ ID NO: 4: F817P, A892P, A899P, A942P, K986P, V987P, S704C/K790C, and Q957E.

12. The engineered protein of claim 1, wherein the engineered coronavirus S protein ectodomain comprises a mutation that eliminates the furin cleavage site.

13. The engineered protein of claim 1, wherein the engineered protein does not comprise an S1 domain.

14. The engineered protein of claim 1, further comprising a stalk region positioned C-terminally relative to the ectodomain, wherein the stalk region has a sequence comprising or consisting of a sequence at least 95% identical to the sequence of amino acid 1143-1208 of SEQ ID NO: 4.

15. The engineered protein of claim 1, wherein the protein is fused or conjugated to a trimerization domain and/or a transmembrane domain.

16. An engineered coronavirus trimer comprising at least one subunit comprising the engineered protein according to claim 1.

17. A pharmaceutical composition comprising a pharmaceutically acceptable carrier; and the engineered protein of claim 1.

18. A nucleic acid molecule comprising a nucleotide sequence that encodes an amino acid sequence of the engineered protein of claim 1.

19. A method of preventing coronavirus infection or a disease associated with coronavirus infection in a subject, comprising administering to the subject an effective amount of the pharmaceutical composition of claim 17.

20. A composition comprising the engineered protein of claim 1 bound to an antibody.

\* \* \* \* \*